(12) United States Patent
Swayze et al.

(10) Patent No.: US 8,796,437 B2
(45) Date of Patent: *Aug. 5, 2014

(54) TETRAHYDROPYRAN NUCLEIC ACID ANALOGS

(71) Applicant: Isis Pharmaceuticals, Inc., Carlsbad, CA (US)

(72) Inventors: Eric E. Swayze, Encinitas, CA (US); Andrew M. Siwkowski, Carlsbad, CA (US); Balkrishen Bhat, Carlsbad, CA (US); Thazha P. Prakash, Carlsbad, CA (US); Charles Allerson, San Diego, CA (US); Punit P. Seth, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/864,534

(22) Filed: Apr. 17, 2013

(65) Prior Publication Data

US 2013/0211064 A1 Aug. 15, 2013

Related U.S. Application Data

(60) Continuation of application No. 13/308,750, filed on Dec. 1, 2011, now Pat. No. 8,440,803, which is a division of application No. 12/192,847, filed on Aug. 15, 2008, now Pat. No. 8,088,904.

(60) Provisional application No. 60/956,100, filed on Aug. 15, 2007, provisional application No. 61/021,236, filed on Jan. 15, 2008, provisional application No. 61/031,226, filed on Feb. 25, 2008, provisional application No. 61/052,030, filed on May 9, 2008.

(51) Int. Cl.
*C07H 21/04* (2006.01)
*C12Q 1/68* (2006.01)
*C07G 3/00* (2006.01)

(52) U.S. Cl.
USPC ............................. 536/23.1; 536/4.1; 435/6.1

(58) Field of Classification Search
USPC .................................... 526/4.1, 23.1; 435/6.1
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,314,893 A | 5/1994 | Tino et al. |
| 5,319,080 A | 6/1994 | Leumann |
| 5,321,131 A | 6/1994 | Agrawal et al. |

(Continued)

FOREIGN PATENT DOCUMENTS

| | | |
|---|---|---|
| GB | 2366290 | 3/2002 |
| WO | WO 93/25565 | 12/1993 |

(Continued)

OTHER PUBLICATIONS

Abramov et al., "Synthesis of D-Altritol Nucleosides with a 3'-O-tert-butyldimethylsilyl protecting group" Nucleosides, Nucleotides, & Nucleic Acids (2004) 23(1-2):439-455.

(Continued)

*Primary Examiner* — Jezia Riley

(74) *Attorney, Agent, or Firm* — Isis Pharmaceuticals, Inc. Patent Dept.

(57) ABSTRACT

The present disclosure describes tetrahydropyran nucleoside analogs, oligomeric compounds prepared therefrom and methods of using the oligomeric compounds. More particularly, tetrahydropyran nucleoside analogs are provided, having one or more chiral substituents, that are useful for enhancing properties of oligomeric compounds including nuclease resistance and binding affinity. In some embodiments, the oligomeric compounds provided herein hybridize to a portion of a target RNA resulting in loss of normal function of the target RNA.

23 Claims, No Drawings

(56) References Cited

U.S. PATENT DOCUMENTS

| | | | |
|---|---|---|---|
| 5,359,044 A | 10/1994 | Cook et al. | |
| 5,366,878 A | 11/1994 | Pederson et al. | |
| 5,367,066 A | 11/1994 | Urdea et al. | |
| 5,378,825 A | 1/1995 | Cook et al. | |
| 5,386,023 A | 1/1995 | Sanghvi et al. | |
| 5,393,878 A | 2/1995 | Leumann | |
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,432,272 A | 7/1995 | Benner | |
| 5,434,257 A | 7/1995 | Matteucci et al. | |
| 5,446,137 A | 8/1995 | Maag et al. | |
| 5,453,496 A | 9/1995 | Caruthers et al. | |
| 5,455,233 A | 10/1995 | Spielvogel et al. | |
| 5,457,187 A | 10/1995 | Gmeiner et al. | |
| 5,459,255 A | 10/1995 | Cook et al. | |
| 5,466,677 A | 11/1995 | Baxter et al. | |
| 5,466,786 A | 11/1995 | Buhr et al. | |
| 5,470,967 A | 11/1995 | Huie et al. | |
| 5,476,925 A | 12/1995 | Letsinger et al. | |
| 5,484,908 A | 1/1996 | Froehler et al. | |
| 5,489,677 A | 2/1996 | Sanghvi et al. | |
| 5,491,133 A | 2/1996 | Walder et al. | |
| 5,502,177 A | 3/1996 | Matteucci et al. | |
| 5,508,270 A | 4/1996 | Baxter et al. | |
| 5,514,785 A | 5/1996 | Van Ness et al. | |
| 5,519,126 A | 5/1996 | Hecht | |
| 5,519,134 A | 5/1996 | Acevedo et al. | |
| 5,525,711 A | 6/1996 | Hawkins et al. | |
| 5,527,899 A | 6/1996 | Froehler | |
| 5,536,821 A | 7/1996 | Agrawal et al. | |
| 5,541,306 A | 7/1996 | Agrawal et al. | |
| 5,541,307 A | 7/1996 | Cook et al. | |
| 5,550,111 A | 8/1996 | Suhadolnik et al. | |
| 5,552,540 A | 9/1996 | Haralambidis | |
| 5,561,225 A | 10/1996 | Maddry et al. | |
| 5,563,253 A | 10/1996 | Agrawal et al. | |
| 5,565,350 A | 10/1996 | Kmiec | |
| 5,565,555 A | 10/1996 | Froehler et al. | |
| 5,567,811 A | 10/1996 | Misiura et al. | |
| 5,571,799 A | 11/1996 | Tkachuk et al. | |
| 5,576,427 A | 11/1996 | Cook et al. | |
| 5,587,361 A | 12/1996 | Cook et al. | |
| 5,587,469 A | 12/1996 | Cook et al. | |
| 5,591,722 A | 1/1997 | Montgomery et al. | |
| 5,594,121 A | 1/1997 | Froehler et al. | |
| 5,596,086 A | 1/1997 | Matteucci et al. | |
| 5,596,091 A | 1/1997 | Switzer | |
| 5,597,909 A | 1/1997 | Urdea et al. | |
| 5,602,240 A | 2/1997 | De Mesmaeker et al. | |
| 5,607,922 A | 3/1997 | De Clercq et al. | |
| 5,608,046 A | 3/1997 | Cook et al. | |
| 5,610,289 A | 3/1997 | Cook et al. | |
| 5,610,300 A | 3/1997 | Altmann et al. | |
| 5,614,617 A | 3/1997 | Cook et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,627,053 A | 5/1997 | Usman et al. | |
| 5,633,360 A | 5/1997 | Bischofberger et al. | |
| 5,639,873 A | 6/1997 | Barascut et al. | |
| 5,645,985 A | 7/1997 | Froehler et al. | |
| 5,646,265 A | 7/1997 | McGee | |
| 5,646,269 A | 7/1997 | Matteucci et al. | |
| 5,652,355 A | 7/1997 | Metelev et al. | |
| 5,652,356 A | 7/1997 | Agrawal | |
| 5,658,873 A | 8/1997 | Bertsch-Frank et al. | |
| 5,663,312 A | 9/1997 | Chaturvedula | |
| 5,670,633 A | 9/1997 | Cook et al. | |
| 5,672,697 A | 9/1997 | Buhr et al. | |
| 5,677,437 A | 10/1997 | Teng et al. | |
| 5,677,439 A | 10/1997 | Weis et al. | |
| 5,681,941 A | 10/1997 | Cook et al. | |
| 5,700,920 A | 12/1997 | Altmann et al. | |
| 5,700,922 A | 12/1997 | Cook | |
| 5,721,218 A | 2/1998 | Froehler | |
| 5,763,588 A | 6/1998 | Matteucci et al. | |
| 5,792,608 A | 8/1998 | Swaminathan et al. | |
| 5,792,747 A | 8/1998 | Schally et al. | |
| 5,792,847 A | 8/1998 | Buhr et al. | |
| 5,830,653 A | 11/1998 | Froehler et al. | |
| 6,005,096 A | 12/1999 | Matteucci et al. | |
| 6,426,220 B1 | 7/2002 | Bennett et al. | |
| 6,455,507 B1 | 9/2002 | Drach et al. | |
| 6,600,032 B1 | 7/2003 | Manoharan et al. | |
| 7,276,592 B2 | 10/2007 | Bergmann et al. | |
| 7,399,845 B2 | 7/2008 | Seth et al. | |
| 7,427,672 B2 | 9/2008 | Imanishi et al. | |
| 8,088,904 B2 | 1/2012 | Swayze et al. | |
| 2004/0033967 A1 | 2/2004 | Van Aerschot et al. | |
| 2004/0033973 A1 | 2/2004 | Manoharan et al. | |
| 2008/0038745 A1 | 2/2008 | Bergmann et al. | |

FOREIGN PATENT DOCUMENTS

| | | |
|---|---|---|
| WO | WO 94/02499 | 2/1994 |
| WO | WO 94/17093 | 8/1994 |
| WO | WO 99/14226 | 3/1999 |
| WO | WO 01/14400 | 3/2001 |
| WO | WO 02/18406 | 3/2002 |
| WO | WO 02/36743 | 5/2002 |
| WO | WO 2004/044245 | 5/2004 |
| WO | WO 2005/049582 | 6/2005 |
| WO | WO 2005/121371 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |

OTHER PUBLICATIONS

Allart et al., "Synthesis of Protected D-Altritol Nucleosides as Building Blocks for Oligonucleotide Synthesis" Tetrahedron (1999) 55:6527-6546.

Allart et al., "D-Altritol Nucleic Acids (ANA): Hybridisation Properties, Stability, and Initial Structural Analysis" Chem. Eur. J. (1999) 5(8):2424-2431.

Altmann et al., "Second Generation of Antisense Oligonucleotides: From Nuclease Resistance to Biological Efficacy in Animals" Chimia (1996) 50:168-176.

Altschul et al., "Basic Local Alignment Search Tool" J. Mol. Med. (1990) 215:403-410.

Andersen et al., "The synthesis of modified D- and L-Anhydrohexitol nucleosides" Tetrahedron Letters (1996) 37(45):8147-8150.

Atkins et al., "Evaluation of the cellular uptake of hexitol nucleic acids in HeLa cells" Parmazie (2000) 55(8):615-617.

Augustyns et al., "Hybridization specificity, enzymatic activity and biological (Ha-ras) activity of oligonucleotides containing 2,4-dideoxy-B-D-erythro-hexopyranosyl nucleosides" Nucleic Acids Res. (1993) 21(20):4670-4676.

Bass et al., "Double-Stranded RNA as a Template for Gene Silencing" Cell (2000) 101:235-238.

Beaucage, "Advances in the Synthesis of Oligonucleotides by the Phosphoramidite Approach" Tetrahedron (1992) 48(12):2223-2311.

Beaucage, "The Functionalization of Oligonucleotides via Phosphoramidite Derivatives" Tetrahedron (1993) 49(10):1925-1963.

Beaucage, "The Synthesis of Specific Ribonucleotides and Unrelated Phosphorylated Biomolecules by the Phosphoramidite Method" Tetrahedron (1993) 49(46):10441-10488.

Bihovsky, "Synthesis of C-glucosides by reactions of glucosyl halides with organocuprates" J. Org. Chem. (1988) 53:4026-4031.

Bisacchi et al., "Regioselective Coupling of Tetraalkylammonium Salts of 6-Iodo-2-aminopurine to a Cyclobutyl Triflate: Efficient Preparation of Homochiral BMS-180,194, a Potent Antiviral Carbocyclic Nucleoside" J. Org. Chem. (1995) 60:2902-2905.

(56) References Cited

OTHER PUBLICATIONS

Boudou et al., "Base pairing of anhydrohexitol nucleosides with 2,6-diaminopurine, 5-methylcytosine and uracil as base moiety" Nucleic Acids Res. (1999) 27(6):1450-1456.
Brazma et al., "Gene Expression Data Analysis" FEBS Lett. (2000) 480:17-24.
Brown et al., "Activity of Novel Adenine Nucleotide Derivatives as Agonists and Antagonists at Recombinant Rat P2X Receptors" Drug Development Res. (2000) 49:253-259.
Carulli et al., "High Throughput Analysis of Differential Gene Expression" J. Cell. Biochem. Suppl. (1998) 30/31:286-296.
Celis et al., "Gene expression profiling: monitoring transcription and translation products using DNA microarrays and proteomics" FEBS Lett. (2000) 480:2-16.
Chiang et al., "Antisense Oligonucleotides Inhibit Intercellular Adhesion Molecule 1 Expression by Two Distinct Mechanisms" J. Biol. Chem. (1991) 266:18162-18171.
De Bouvere et al., "Improved Synthesis of Anhydrohexitol Building Blocks for Oligonucleotide Synthesis" Liebigs Ann./Recueil (1997) 1453-1461;1513-1520.
Elbashir et al., "Duplexes of 21-nucleotide RNAs mediate RNA interference in cultured mammalian cells" Nature (2001) 411:494-498.
Elbashir et al., "RNA interference is mediated by 21- and 22-nucleotide RNAs" Genes Dev. (2001) 15:188-200.
Englisch et al., "Chemically Modified Oligonucleotides as Probes and Inhibitors" Angewandte Chemie, International Edition (1991) 30:613.
Fire et al., "Potent and specific genetic interference by double-stranded RNA in Caenorhabditis elegans" Nature (1998) 391:806-811.
Flores et al., "Antimalarial antisense activity of hexitol nucleic acids" Parasitol Res. (1999) 85:864-866.
Freier et al., "The ups and downs of nucleic acid duplex stability: structure-stability studies on chemically-modified DNA:RNA duplexes" Nucleic Acids Research (1997) 25(22):4429-4443.
Froeyen et al., "Molecular-Dynamics Studies of Single-Stranded Hexitol, Altritol, Mannitol, and Ribose Nucleic Acids (HNA, MNA, ANA, and RNA, Resp.) and of the Stability of HNA—RNA, ANA—RNA, and MNA—RNA Duplexes" Helvetica Chimica Acta (2000) 83:2153-2182.
Fuchs et al., "Identification of Differentially Expressed Genes by Mutually Subtracted RNA Fingerprinting" Anal. Biochem. (2000) 286:91-98.
Gait et al., Applications of Chemically Synthesized RNA in RNA:Protein Interactions, Ed. Smith (1998) 1-36.
Gallo et al., "2'-C-Methyluridine phosphoramidite: a new building block for the preparation of RNA analogues carrying the 2'-hydroxyl group" Tetrahedron (2001) 57:5707-5713.
Going et al., "Molecular Pathology and Future Developments" Eur. J. Cancer (1999) 35(14):1895-1904.
Greene and Wuts, "Protective Groups in Organic Synthesis" 3rd Edition, John Wiley & Sons, New York (1999).
Hendrix et al., "1',5'-Anhydrohexitol Oligonucleotides: Synthesis, Base Pairing and Recognition by Regular Oligodeoxyribonucleotides and Oligoribonucleotides" Chem. Eur. J. (1997) 3(1):110-120.
Hendrix et al., "1',5'-Anhydrohexitol Oligonucleotides: Hybridisation and Strand Displacement with Oligoribonucleotides, Interaction with Rnase H and HIV Reverse Transcriptase" Chem. Eur. J. (1997) 3(9):1513-1520.
Herdewijn et al., "Targeting RNA with Conformationally Restricted Oligonucleotides" Liebigs Ann. (1996) 1337-1348.
Hossain et al., "Oligonucleotides Composed of 2'-Deoxy-1',5'-anhydro-d-mannitol Nucleosides with a Purine Base Moiety" J. Org. Chem. (1998) 63:1574-1582.
Jungblut et al., "Proteomics in human disease: Cancer, heart and infectious diseases" Electrophoresis (1999) 20:2100-2110.
Jurecic et al., "Long-distance DD-PCR and cDNA microarrays" Curr. Opin. Microbiol. (2000) 3:316-321.
Kang et al., "Inhibition of MDRI gene expression by chimeric HNA antisense oligonucleotides" Nucleic Acids Research (2004) 32(14):4411-4419.
Kozlov et al., "A Highly Enatio-Selective Hexitol Nucleic Acid Template for Nonenzymatic Oligoguanylate Synthesis" J. Am. Chem. Soc. (1999) 121:1108-1109.
Kozlov et al., "Nonenzymatic Synthesis of RNA and DNA Oligomers on Hexitol Nucleic Acid Templates: The Importance of the A Structure" J. Am. Chem. Soc. (1999) 121(12):2653-2656.
Kozlov et al., "Efficienct Transfer of Information from Hexitol Nucleic Acids to RNA during Nonenzymatic Oligomerization" J. Am. Chem. Soc. (1999) 121:5856-5859.
Kozlov et al., "Nonenzymatic Template-Directed Reactions on Altritol Oligomers, Preorganized Analogues of Oligonucleotides" Chem. Eur. J. (2000) 6(1):151-155.
Kroschwitz, The Concise Encyclopedia of Polymer Science and Engineering, Kroschwitz ed., John Wiley & Sons (1990) pp. 858-859.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotechnol. (2000) 80:143-157.
Lescrinier et al., "Solution structure of a HNA-RNA hybrid" Chemistry & Biology (2000) 7:719-731.
Lescrinier et al., "Solution Structure of a Hexitol Nucleic Acid Duplex with Four Consecutive T-T Base Pairs" Helvetica Chimica Acta (2000) 83:1291-1310.
Leumann, "DNA Analogues: From Supramolecular Principles to Biological Properties" Bioorganic & Medicinal Chemistry (2002) 10:841-854.
Madden et al., "Serial analysis of gene expression: from gene discovery to target identification" Drug Discov. Today (2000) 5:415-425.
Tijsterman et al., "RNA Helicase MUT-14-Dependent Gene Silencing Triggered in C. elegans by Short Antisense RNAs" Science (2002) 295:694-697.
Timmons et al., "Specific interference by ingested dsRNA" Nature (1998) 395:854.
Timmons et al., "Ingestion of bacterially expressed dsRNAs can produce specific and potent genetic interference in Caenorhabditis elegans" Gene (2001) 263:103-112.
To, "Identification of Differential Gene Expression by High Throughput Analysis" Comb. Chem. High Throughput Screen. (2000) 3:235-241.
Tuschl et al., "Targeted mRNA degradation by double-stranded RNA in vitro" Genes Dev. (1999) 13:3191-3197.
Van Aerschot et al., "1,5-Anhydrohexitol Nucleic Acids, a New Promising Antisense Construct" Agnew. Chem. Int. Ed. Engl. (1995) 34(12):1338-1339.
Van Aerschot et al., "Increased RNA affinity of HNA analogues by introducing alkoxy substituents at the C-1 or C-3 position" Nucleosides, Nucleotides & Nucleic Acids (2001) 20(4-7):781-784.
Vandermeeren et al., "Biological Activity of Hexitol Nucleic Acids Targeted at Ha-ras and Intracellular Adhesion Molecule-1 mRNA" (2000) 59:655-663.
Vastmans et al., "Recognition of 1,5-Anhydrohexitol Adenine Triphosphate by a DNA Polymerase" Collection Symposium Series (1999) 2:156-160.
Verheggan et al., "Synthesis and Antiherpes Virus Activity of 1,5-Anhydrohexitol Nucleosides" J. Med. Chem. (1993) 36:2033-2040.
Verheggan et al., "Synthesis, Biological Evaluation, and Structure Analysis of a Series of New 1,5-Anhydrohexitol Nucleosides" J. Med. Chem. (1995) 38:826-835.
Verheggan et al., "Synthesis of 1,5-Anhydrohexitol Nucleosides as Mimics of AZT, D4T and DDC+" Nucleosides & Nucleotides (1996) 15(1-3):325-335.
Wang et al., "Cyclohexene Nucleic Acids (CeNA): Serum Stable Oligonucleotides that Activate Rnase H and Increase Duplex Stability with Complementary RNA" J. Am. Chem. (2000) 122:8595-8602.

(56) References Cited

OTHER PUBLICATIONS

Wouters et al., "5-Substituted Pyrimidine 1,5-Anhydrohexitols: Conformational Analysis and Interaction with Viral Thymidine Kinase" Bioorganic & Medicinal Chemistry Letters (1999) 9:1563-1566.

Zhang et al., "PowerBLAST: A New Network Blast Application for Interactive or Automated Sequence Analysis and Annotation" Genome Res. (1997) 7:649-656.

Zhou et al., "Fine Tuning of Electrostatics around the Internucleotide Phosphate through Incorporation of Modified 2',4'-Carbocyclic-LNAs and -ENAs Leads to Significant Modulation of Antisense Properties" J. Org. Chem. (2009) 74:118-134.

International Search Report for Application No. PCT/US2008/073379 dated Feb. 20, 2009.

International Search Report for Application No. PCT/US2010/022759 dayed Jun. 4, 2010.

Montgomery et al., "RNA as a target of double-stranded RNA-mediated genetic interference in Caenorhabditis elegans" PNAS (1998) 95:15502-15507.

Nishikura et al., "A Short Primer on RNAi: RNA-Directed RNA Polymerase Acts as a Key Catalyst" Cell (2001) 107:415-416.

Ostrowski et al., "5-Substituted Pyrimidines with a 1,5-Anhydro-2,3-dideoxy-D-arabino-hexitol Moiety at N-1: Synthesis, Antiviral Activity, Conformational Analysis, and Interaction with Viral Thymidine Kinase" J. Med. Chem. (1998) 41:4343-4353.

Perez-Perez et al., "Synthesis and antiviral activity of 2-deoxy-1,5-anhydro-D-mannitol nucleosides containing a pyrimidine base moiety" Bioorg. Med. Chem. Lett. (1996) 6(13):1457-1460.

Pochet et al., "Replicative Capability of Anhydrohexitol Analogues of Nucleotides" Nucleosides & Nucleotides (1999) 18(4&5):1015-1017.

Prashar et al., "READS A Method for Display of 3'-End Fragments of Restriction Enzyme-Digested cDNAs for Analysis of Differential Gene Expression" Methods Enzymol. (1999) 303:258-272.

Sanghvi and Cook, "Carboydrate Modifications in Antisense Research" ACS Symposium Series 580, Chapters 3 and 4, pp. 40-65, 1994.

Sanghvi, Antisense Research and Applications, Crooke and Lebleu ed., CRC Press (1993) Chapter 15, pp. 276-278.

Sanghvi, Antisense Research and Applications, Crooke and Lebleu ed., CRC Press (1993) Chapter 15, pp. 298-302.

Scaringe, "RNA Oligonucleotide Synthesis via 5'-Silyl-2'-Orthoester Chemistry" Methods (2001) 23:206-217.

Sonveaux, "Chapter 1: Protecting Groups in Oligonucleotide Synthesis" Protocols for Oligonucleotide Conjugates, Agrawals Eds, Humana Press, New Jersey (1994) vol. 26, pp. 1-72.

Sutcliffe et al., "TOGA: An automated parsing technology for analyzing expression of nearly all genes" PNAS (2000) 97(5):1976-1981.

Tabara et al., "RNAi in C. elegans: Soaking in the Genome Sequence" Science (1998) 282:430-431.

SEQUENCE LISTING

<160> NUMBER OF SEQ ID NOS: 8

<210> SEQ ID NO 1
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 13, 14
<223> OTHER INFORMATION: Bases at these potions are RNA

<400> SEQUENCE: 1
cutagcactg gccu                                                       14

<210> SEQ ID NO 2
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 2
cttagcactg gcct                                                       14

<210> SEQ ID NO 3
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 17, 18
<223> OTHER INFORMATION: Bases at these positions are RNA

<400> SEQUENCE: 3
cugctagcct ctggatuu                                                   18

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 4
ctgctagcct ctggattt                                                   18

<210> SEQ ID NO 5
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 5
tcttagcact ggcctt                                                     16

<210> SEQ ID NO 6
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 6

```
ctcttagcac tggcctt                                                  17

<210> SEQ ID NO 7
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 6, 7, 9, 10, 12, 13, 14
<223> OTHER INFORMATION: Bases at these positions are RNA

<400> SEQUENCE: 7
aggccagtgc taag                                                     14

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2, 3, 4, 5, 6, 7, 8, 9, 10, 12, 13, 15
      16, 17, 18, 19
<223> OTHER INFORMATION: Bases at these positions are RNA

<400> SEQUENCE: 8
tcaaggccag tgctaagagt                                               20
```

TETRAHYDROPYRAN NUCLEIC ACID ANALOGS

CROSS-REFERENCE TO RELATED APPLICATIONS

The present application is a continuation of U.S. application Ser. No. 13/308,750, filed Dec. 1, 2011; which is a divisional of U.S. application Ser. No. 12/192,847, filed Aug. 15, 2008, now U.S. Pat. No. 8,088,904; which claims benefit of priority to U.S. Provisional Application Ser. No. 60/956,100 filed Aug. 15, 2007, U.S. Provisional Application Ser. No. 61/021,236 filed Jan. 15, 2008, U.S. Provisional Application Ser. No. 61/031,226 filed Feb. 25, 2008, and U.S. Provisional Application Ser. No. 61/052,030 filed May 9, 2008, all of which are incorporated herein by reference in their entirety.

SEQUENCE LISTING

The present application is being filed along with a Sequence Listing in electronic format. The Sequence Listing is provided as a file entitled CHEM0041USC1SEQ.txt, created on Apr. 16, 2013 which is 4 Kb in size. The information in the electronic format of the sequence listing is incorporated herein by reference in its entirety.

FIELD OF THE INVENTION

Provided herein are tetrahydropyran nucleoside analogs, oligomeric compounds prepared therefrom and methods of using the oligomeric compounds. More particularly, the tetrahydropyran nucleoside analogs each have a substituted tetrahydropyran ring replacing the naturally occurring pentofuranose ring. In certain embodiments, the oligomeric compounds hybridize to a portion of a target RNA resulting in loss of normal function of the target RNA.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example affinity and nuclease resistance. One such group of chemically modified nucleosides includes tetrahydropyran nucleoside analogs wherein the furanose ring is replaced with a tetrahydropyran ring.

The synthesis of various tetrahydropyran nucleoside analogs has been reported in the literature, see for example: Verheggen et al., *J. Med. Chem.*, 1995, 38, 826-835; Altmann et al., *Chimia*, 1996, 50, 168-176; Herdewijn et al., *Bioorganic & Medicinal Chemistry Letters*, 1996, 6 (13), 1457-1460; Verheggen et al., *Nucleosides & Nucleotides*, 1996, 15(1-3), 325-335; Ostrowski et al., *J. Med. Chem.*, 1998, 41, 4343-4353; Allart et al., *Tetrahedron.*, 1999, 55, 6527-6546; Wouters et al., *Bioorganic & Medicinal Chemistry Letters*, 1999, 9, 1563-1566; Brown, et al., *Drug Development Res.*, 2000, 49, 253-259; published PCT application: WO 93/25565; WO 02/18406; and WO 05/049582; U.S. Pat. Nos. 5,314,893; 5,607,922; and 6,455,507.

Various tetrahydropyran nucleoside analogs have been described as monomers and have also been incorporated into oligomeric compounds (see for example: Published PCT application, WO 93/25565, published Dec. 23, 1993; Augustyns et al. *Nucleic Acids Res.*, 1993, 21(20), 4670-4676; Verheggen et al., *J. Med. Chem.*, 1993, 36, 2033-2040; Van Aerschol et al., *Angew. Chem. Int. Ed. Engl.*, 1995, 34(12), 1338-1339; Anderson et al., *Tetrahedron Letters*, 1996, 37(45), 8147-8150; Herdewijn et al., *Liebigs Ann.*, 1996, 1337-1348; De Bouvere et al., *Liebigs Ann./Recueil*, 1997, 1453-1461; 1513-1520; Hendrix et al., *Chem. Eur.* 1, 1997, 3(1), 110-120; Hendrix et al., *Chem. Eur.* 1, 1997, 3(9), 1513-1520; Hossain et al, *J. Org. Chem.*, 1998, 63, 1574-1582; Allart et al., *Chem. Eur.* 1, 1999, 5(8), 2424-2431; Boudou et al., *Nucleic Acids Res.*, 1999, 27(6), 1450-1456; Kozlov et al., *J. Am. Chem. Soc.*, 1999, 121, 1108-1109; Kozlov et al., *J. Am. Chem. Soc.*, 1999, 121, 2653-2656; Kozlov et al., *J. Am. Chem. Soc.*, 1999, 121, 5856-5859; Pochet et al., *Nucleosides & Nucleotides*, 1999, 18 (4&5), 1015-1017; Vastmans et al., *Collection Symposium Series*, 1999, 2, 156-160; Froeyen et al., *Helvetica Chimica Acta*, 2000, 83, 2153-2182; Kozlov et al., *Chem. Eur. J.*, 2000, 6(1), 151-155; Atkins et al., *Parmazie*, 2000, 55(8), 615-617; Lescrinier et al., *Chemistry & Biology*, 2000, 7, 719-731; Lescrinier et al., *Helvetica Chimica Acta*, 2000, 83, 1291-1310; Wang et al., *J. Am. Chem.*, 2000, 122, 8595-8602; US Patent Application US 2004/0033967; Published US Patent Application US 2008/0038745; Published and Issued U.S. Pat. No. 7,276,592). DNA analogs have also been reviewed in an article (see: Leumann, J. C, *Bioorganic & Medicinal Chemistry*, 2002, 10, 841-854) which included a general discussion of tetrahydropyran nucleoside analogs (under the name: hexitol nucleic acid family).

Oligomeric compounds having phosphodiester linked 3'-H tetrahydropyran nucleoside analogs (also referred to in the art as HNA—hexitol nucleic acids or 1,5-anhydrohexitol nucleic acids) have been prepared for evaluation in cell assays. The different motifs that have been evaluated are fully modified wherein each monomer is a phosphodiester linked 3'-H tetrahydropyran nucleoside analog and gapped wherein each monomer in the 3' and 5' external regions of the oligomeric compound are each phosphodiester linked 3'-H tetrahydropyran nucleoside analogs and each monomer in the internal region is a phosphorothioate linked deoxyribonucleoside (see: Kang et al., *Nucleic Acids Research*, 2004, 32(14), 4411-4419; Vandermeeren et al., 2000, 55, 655-663; Flores et al., *Parasitol Res.*, 1999, 85, 864-866; and Hendrix et al., *Chem. Eur.* 1997, 3(9), 1513-1520).

Oligomeric compounds having phosphodiester linked 3'-OH tetrahydropyran nucleoside analogs (also referred to in the art as ANA or D-altritol nucleic acids) have been prepared and evaluated both structurally and in vitro (Allart et al., *Chem. Eur.* 1, 1999, 5(8), 2424-2431).

Chemically modified siRNA's having incorporated hexitol nucleotides (also referred to in the art as HNA nucleic acids) have been prepared and tested for silencing capacity (see: Published PCT application, WO 06/047842, published May 11, 2006.

Consequently, there remains a long-felt need for agents that specifically regulate gene expression via antisense mechanisms. Disclosed herein are 4-substituted-5-hydroxy-6-hydroxymethyl-tetrahydropyran nucleoside analogs that are useful in the preparation of antisense compounds for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Tetrahydropyran nucleoside analogs, oligomeric compounds comprising the tetrahydropyran analogs and methods of using the oligomeric compounds are provided herein. The tetrahydropyran nucleoside analogs impart enhanced properties to oligomeric compounds they are incorporated into.

The variables are defined individually in further detail herein. It is to be understood that the tetrahydropyran nucleoside analogs, oligomer compounds, and methods of use thereof provided herein include all combinations of the embodiments disclosed and variables defined herein.

In certain embodiments, tetrahydropyran nucleoside analogs are provided having Formula XVI:

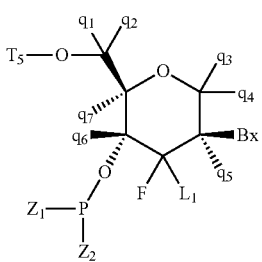

XVI wherein:

Bx is a heterocyclic base moiety;
$T_5$ is a hydroxyl protecting group;
$L_1$ is H, halogen, $C_1$-$C_6$ alkyl or substituted $C_1$-$C_6$ alkyl;
$Z_1$ is $O^-$ or $OE_1$;
$Z_2$ is OH, $OE_1$ or $N(E_1)(E_2)$;
each $E_1$ and $E_2$ is, independently, alkyl or substituted alkyl;
$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
wherein each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, tetrahydropyran nucleoside analogs having Formula XVI are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl.

In certain embodiments, tetrahydropyran nucleoside analogs having Formula XVI are provided wherein Bx is uracil, 5-methyluracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4]benzoxazin-2(3H)-one, 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',': 4,5]pyrrolo[2,3-d]pyrimidin-2-one. In certain embodiments, Bx is uracil, 5-methyluracil, thymine, cytosine, 5-methylcytosine, 2,6-diaminopurine, adenine or guanine.

In certain embodiments, tetrahydropyran nucleoside analogs having Formula XVI are provided wherein $T_5$ is acetyl, t-butyl, t-butoxymethyl, methoxymethyl, tetrahydropyranyl, 1-ethoxyethyl, 1-(2-chloroethoxy)ethyl, 2-trimethylsilyl-ethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4-methoxytrityl, 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl or substituted pixyl. In certain embodiments, $T_5$ is acetyl, benzyl, t-butyldimethylsilyl, t-butyldiphenylsilyl or dimethoxytrityl.

In certain embodiments, tetrahydropyran nucleoside analogs having Formula XVI are provided wherein $L_1$ is F. In certain embodiments, $L_1$ is H.

In certain embodiments, tetrahydropyran nucleoside analogs having Formula XVI are provided wherein $Z_1$ is $O^-$ and $Z_2$ is OH. In certain embodiments, $Z_1$ is $O(CH_2)_2CN$, $Z_2$ is $N[CH_2(CH_3)_2]_2$ and $T_5$ is 4,4'-dimethoxytrityl. In certain embodiments, $Z_1$ is $O^-$ and $Z_2$ is OH which provides an H phosphonate group at the 4' position of the tetrahydropyran nucleoside analog which can also be written as 3'-O—P(=O)(H)(OH or $O^-$amine$^+$). In certain embodiments, $Z_1$ is $O(CH_2)_2CN$, $Z_2$ is $N[CH_2(CH_3)_2]_2$ and $T_5$ is 4,4'-dimethoxytrityl which provides a phosphoramidite at the 3'-position.

In certain embodiments, tetrahydropyran nucleoside analogs having Formula XVI are provided and have the configuration as illustrated in Formula XVII:

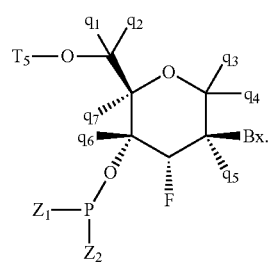

XVII

In certain embodiments, tetrahydropyran nucleoside analogs having Formula XVII are provided wherein $q_1$, $q_2$, $q_3$, $q_4$, $q_5$, $q_6$ and $q_7$ are each H; Bx is uracil, 5-methyluracil, thymine, cytosine, 5-methyl-cytosine, 2,6-diaminopurine, adenine or guanine; $T_5$ is 4,4'-dimethoxytrityl; $Z_1$ is $O(CH_2)_2CN$; and $Z_2$ is $N[CH_2(CH_3)_2]_2$.

In certain embodiments, oligomeric compounds are provided comprising at least one tetrahydropyran nucleoside analog of Formula X:

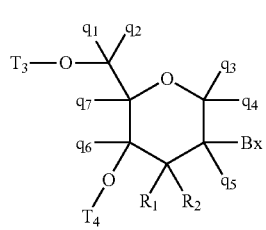

X wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1, q_2, q_3, q_4, q_5, q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $R_1$ and $R_2$ is fluoro and the other of $R_1$ and $R_2$ is H, halogen, $C_1$-$C_6$ alkyl or substituted $C_1$-$C_6$ alkyl;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl; and wherein said oligomeric compound comprises from about 8 to about 40 monomer subunits linked by internucleoside linking groups and at least one internucleoside linking group is a phosphorothioate internucleoside linking group.

In certain embodiments, the oligomeric compounds comprise at least two tetrahydropyran nucleoside analogs of Formula X. In certain embodiments, the oligomeric compounds comprise at least two contiguous tetrahydropyran nucleoside analogs of Formula X that are linked by a phosphorothioate internucleoside linking group.

In certain embodiments, the oligomeric compounds comprise at least one tetrahydropyran nucleoside analog of Formula X and at least one β-D-2'-deoxyribonucleoside. In certain embodiments, the oligomeric compounds comprise at least one tetrahydropyran nucleoside analog of Formula X that is linked to a β-D-2'-deoxyribonucleoside by a phosphorothioate internucleoside linking group.

In certain embodiments, the oligomeric compounds comprise at least one region of from 2 to about 5 contiguous tetrahydropyran nucleoside analogs of Formula X. In certain embodiments, the oligomeric compounds comprise at least one region of from 2 to about 5 contiguous tetrahydropyran nucleoside analogs of Formula X and at least one additional region of from 1 to about 5 contiguous monomer subunits other than β-D-ribonucleosides and β-D-2'-deoxyribonucleosides wherein the additional region is separated from the at least one region by at least one β-D-2'-deoxyribonucleoside. In certain embodiments, oligomeric compounds are provided comprising at least two regions, each region having from 1 to about 5 contiguous tetrahydropyran nucleoside analogs of Formula X and wherein the two regions are separated by at least one monomer subunit wherein each monomer subunit is, independently, a nucleoside or a modified nucleoside.

In certain embodiments, oligomeric compounds are provided comprising a gapped oligomeric compounds comprising at least two regions, each region having from 1 to about 5 contiguous tetrahydropyran nucleoside analogs of Formula X wherein one of said at least two regions of contiguous tetrahydropyran nucleoside analogs of Formula X is located at the 5'-end and the other of said at least two regions of contiguous tetrahydropyran nucleoside analogs of Formula X is located at the 3'-end and wherein the two regions are separated by an internal region comprising from about 6 to about 18 monomer subunits wherein each monomer subunit is, independently, a nucleoside or a modified nucleoside.

In certain embodiments, the oligomeric compounds comprise at least one phosphodiester internucleoside linking group. In certain embodiments, each internucleoside linking group is a phosphorothioate internucleoside linking group.

In certain embodiments, oligomeric compounds are provided wherein each $q_1, q_2, q_3, q_4, q_5, q_6$ and $q_7$ is H. In certain embodiments, at least one of $q_1, q_2, q_3, q_4, q_5, q_6$ or $q_7$ is other than H. In certain embodiments, at least one of $q_1, q_2, q_3, q_4, q_5, q_6$ or $q_7$ is methyl.

In certain embodiments, oligomeric compounds are provided wherein each tetrahydropyran nucleoside analog has the configuration of Formula XI:

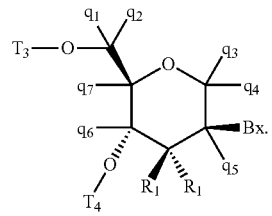

XI

In certain embodiments, oligomeric compounds are provided wherein each tetrahydropyran nucleoside analog has Formula XII:

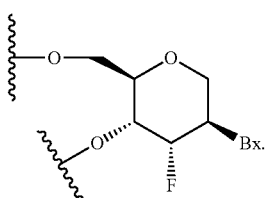

XII

In certain embodiments, oligomeric compounds are provided comprising from about 10 to about 21 monomer subunits in length. In certain embodiments, oligomeric compounds are provided comprising from about 10 to about 16 monomer subunits in length. In certain embodiments, oligomeric compounds are provided comprising from about 10 to about 14 monomer subunits in length. In certain embodiments, the comprising term is included solely to provide for additional substituent groups routinely added to oligomeric compounds such as but not limited to protecting groups such as hydroxyl protecting groups, optionally linked conjugate groups, 5' and/or 3'-terminal groups and/or other substituent groups.

In certain embodiments, oligomeric compounds are provided comprising at least two tetrahydropyran nucleoside analogs of Formula XIII:

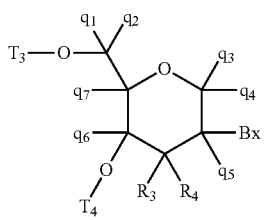

XIII wherein independently for each of said tetrahydropyran nucleoside analogs of Formula XIII:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1, q_2, q_3, q_4, q_5, q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, halogen, $C_1$-$C_6$ alkyl, substituted $C_1$-$C_6$ alkyl, $C_1$-$C_6$ alkoxy or substituted $C_1$-$C_6$ alkoxy;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl;

wherein said oligomeric compound comprises from about 8 to about 40 monomer subunits; and at least two of the tetrahydropyran nucleoside analogs of Formula XIII are linked by a phosphorothioate internucleoside linking group.

In certain embodiments, oligomeric compounds are provided wherein one of $R_3$ and $R_4$ is H and the other of $R_3$ and $R_4$ is H, $OCH_3$ or F for at least one tetrahydropyran nucleoside analog of Formula XIII.

In certain embodiments, oligomeric compounds are provided comprising at least one β-D-2'-deoxyribonucleoside. In certain embodiments, oligomeric compounds are provided comprising at least one β-D-2'-deoxyribonucleoside wherein at least one β-D-2'-deoxyribonucleoside is linked to a tetrahydropyran nucleoside analog of Formula XIII by a phosphorothioate internucleoside linking group.

In certain embodiments, oligomeric compounds are provided comprising at least one region of from 2 to about 5 contiguous tetrahydropyran nucleoside analogs of Formula XIII. In certain embodiments, oligomeric compounds are provided comprising at least one region of from 2 to about 5 contiguous tetrahydropyran nucleoside analogs of Formula XIII and at least one additional region of from 1 to about 5 contiguous monomer subunits other than β-D-ribonucleosides or β-D-2'-deoxyribonucleosides wherein the additional region is separated from the at least one region by at least one β-D-2'-deoxyribonucleoside. In certain embodiments, oligomeric compounds are provided comprising at least one region of from 2 to about 5 contiguous tetrahydropyran nucleoside analogs of Formula XIII and at least one additional region of from 1 to about 5 contiguous tetrahydropyran nucleoside analogs of Formula XIII wherein the at least one region of from 2 to about 5 contiguous tetrahydropyran nucleoside analogs of Formula XIII is separated from the additional region of from 1 to about 5 contiguous tetrahydropyran nucleoside analogs of Formula XIII by at least one nucleoside or modified nucleoside.

In certain embodiments, oligomeric compounds are provided comprising at least two regions of from 1 to about 5 contiguous tetrahydropyran nucleoside analogs of Formula XIII comprising a gapped oligomeric compound wherein one of said at least two regions of contiguous tetrahydropyran nucleoside analogs of Formula XIII is located at the 5'-end and the other of said at least two regions of contiguous tetrahydropyran nucleoside analogs of Formula XIII is located at the 3'-end and wherein the two regions are separated by an internal region comprising from about 6 to about 14 monomer subunits wherein each monomer subunit is, independently, a nucleoside or a modified nucleoside.

In certain embodiments, oligomeric compound are provided comprising at least one phosphodiester internucleoside linking group. In certain embodiments, oligomeric compound are provided wherein each internucleoside linking group is a phosphorothioate internucleoside linking group.

In certain embodiments, oligomeric compounds are provided wherein each $q_1, q_2, q_3, q_4, q_5, q_6$ and $q_7$ is H. In certain embodiments, wherein at least one of $q_1, q_2, q_3, q_4, q_5, q_6$ or $q_7$ is other than H. In certain embodiments, wherein at least one of $q_1, q_2, q_3, q_4, q_5, q_6$ or $q_7$ is methyl.

In certain embodiments, oligomeric compounds are provided wherein each tetrahydropyran nucleoside analog of Formula XIII has the configuration of Formula XIV:

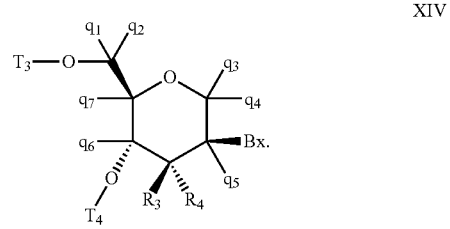

XIV

In certain embodiments, oligomeric compounds are provided wherein at least one tetrahydropyran nucleoside analog has Formula XV:

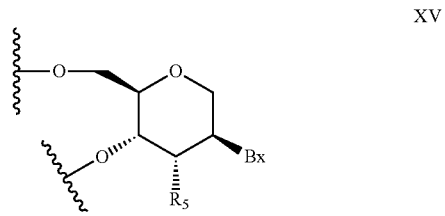

XV wherein:
Bx is a heterocyclic base moiety; and
$R_5$ is H, $OCH_3$ or F.

In certain embodiments, oligomeric compounds are provided each tetrahydropyran nucleoside analog has Formula XV. In certain embodiments, oligomeric compounds are provided wherein each tetrahydropyran nucleoside analog has Formula XV and each $R_5$ is H. In certain embodiments, oligomeric compounds are provided wherein each tetrahydropyran nucleoside analog has Formula XV and each $R_5$ is $OCH_3$. In certain embodiments, oligomeric compounds are provided wherein each tetrahydropyran nucleoside analog has Formula XV and each $R_5$ is F.

In certain embodiments, oligomeric compounds are provided comprising from about 10 to about 21 monomer subunits in length. In certain embodiments, oligomeric compounds are provided comprising from about 10 to about 16 monomer subunits in length. In certain embodiments, oligomeric compounds are provided comprising from about 10 to about 14 monomer subunits in length. In certain embodiments, the comprising term is included solely to provide for additional substituent groups routinely added to oligomeric compounds such as but not limited to protecting groups such as hydroxyl protecting groups, optionally linked conjugate groups, 5' and/or 3'-terminal groups and/or other substituent groups.

In certain embodiments, methods are provided comprising contacting a cell in an animal with one or more oligomeric compounds provided herein. In certain embodiments, the cell is in a human. In certain embodiments, the methods are performed with an oligomeric compound provided herein that is complementary to a target RNA. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function.

In certain embodiments, the methods provided herein further comprise evaluating the activity of the oligomeric compound on the cell. In certain embodiments, the step of evaluating comprises detecting the levels of target RNA. In certain embodiments, the step of evaluating comprises detecting the levels of a protein. In certain embodiments, the step of evaluating comprises detection of one or more phenotypic effects.

In certain embodiments, tetrahydropyran nucleoside analogs of Formula I are provided:

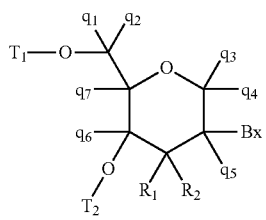

I wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
each $q_1$, $q_2$, $q_3$, $q_4$, $q_5$, $q_6$ and $q_7$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
one of $R_1$ and $R_2$ is fluoro and the other of $R_1$ and $R_2$ is H, halogen, $C_1$-$C_6$ alkyl or substituted $C_1$-$C_6$ alkyl; and
wherein each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, the other of $R_1$ and $R_2$ is H. In certain embodiments, $R_1$ and $R_2$ are each fluoro. In certain embodiments, the other of $R_1$ and $R_2$ is $C_1$-$C_6$ alkyl or substituted $C_1$-$C_6$ alkyl. In certain embodiments, the other of $R_1$ and $R_2$ is methyl, ethyl, substituted methyl or substituted ethyl. the other of $R_1$ and $R_2$ is methyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is $C_1$-$C_6$ alkyl or substituted $C_1$-$C_6$ alkyl. In certain embodiments, at least one of $q_1$, $q_2$, $q_3$, $q_4$, $q_5$, $q_6$ and $q_7$ is methyl. In certain embodiments, at least one of $q_1$ and $q_2$ is methyl. In certain embodiments, at least one of $q_3$ and $q_4$ is methyl. In certain embodiments, at least one of $q_5$, $q_6$ and $q_7$ is methyl.

In certain embodiments, $T_1$ and $T_2$ are each H. In certain embodiments, at least one of $T_1$ and $T_2$ is a hydroxyl protecting group. In certain embodiments, each hydroxyl protecting group is, independently, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4-methoxytrityl, 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl or substituted pixyl.

In certain embodiments, $T_1$ is acetyl, benzyl, t-butyldimethylsilyl, t-butyldiphenylsilyl, 4-methoxytrityl or 4,4'-dimethoxytrityl. In certain embodiments, one of $T_1$ and $T_2$ is a hydroxyl protecting group and the other of $T_1$ and $T_2$ is diisopropylcyanoethoxy phosphoramidite or H-phosphonate. In certain embodiments, $T_1$ is 4,4'-dimethoxytrityl and $T_2$ is diisopropylcyanoethoxy phosphoramidite.

In certain embodiments, Bx is uracil, thymine, cytosine, adenine or guanine. In certain embodiments, Bx is a pyrimidine, substituted pyrimidine, purine or substituted purine wherein said substitution is other than an intercalator or a linked group that does not interact with a nucleic acid target when the tetrahydropyran nucleoside analog is located in an oligomeric compound. In certain embodiments, Bx is uracil, 5-methyluracil, 5-thiazolo-uracil, 2-thio-uracil, 5-propynyl-uracil, thymine, 2'-thio-thymine, cytosine, 5-methyl-cytosine, 5-thiazolo-cytosine, 5-propynyl-cytosine, adenine, guanine, 2,6-diaminopurine, 1H-pyrimido[5,4-b][1,4]benzoxazin-2(3H)-one, 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',':4,5]-pyrrolo[2,3-d]pyrimidin-2-one. Bx is uracil, 5-methyluracil, 5-propynyl-uracil, thymine, cytosine, 5-methyl-cytosine, 5-propynyl-cytosine, adenine or guanine.

In certain embodiments, the tetrahydropyran nucleoside analogs have the configuration shown in Formula Ia:

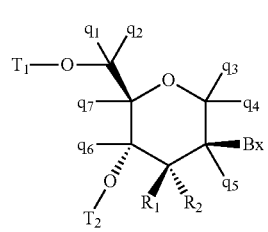

Ia wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
one of $R_1$ and $R_2$ is fluoro and the other of $R_1$ and $R_2$ is H, halogen, $C_1$-$C_6$ alkyl or substituted $C_1$-$C_6$ alkyl; and
wherein each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, tetrahydropyran nucleoside analogs are provided having the configuration shown in formula Ia wherein $R_2$ is fluoro. In certain embodiments, tetrahydropyran nucleoside analogs are provided having the configuration shown in formula Ia wherein $R_1$ is H and $R_2$ is fluoro. In certain embodiments, tetrahydropyran nucleoside analogs are provided having the configuration shown in formula Ia wherein $R_1$ is H, $R_2$ is fluoro and $q_1$, $q_2$, $q_3$, $q_4$, $q_5$, $q_6$ and $q_7$ are each H.

In certain embodiments, tetrahydropyran nucleoside analogs are provided having the configuration shown in formula Ia wherein $R_1$ is $C_1$-$C_6$ alkyl or substituted $C_1$-$C_6$ alkyl. In certain embodiments, tetrahydropyran nucleoside analogs are provided having the configuration shown in formula Ia wherein $R_1$ is methyl, ethyl, substituted methyl or substituted ethyl. In certain embodiments, tetrahydropyran nucleoside analogs are provided having the configuration shown in formula Ia wherein $R_1$ and $R_2$ are each fluoro.

In certain embodiments, tetrahydropyran nucleoside analogs are provided having Formula II:

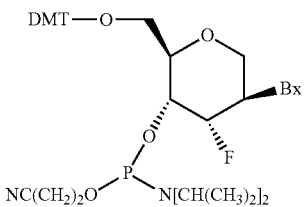

wherein:

Bx is a heterocyclic base moiety.

In certain embodiments, oligomeric compounds comprising at least one tetrahydropyran nucleoside analog of Formula III are provided:

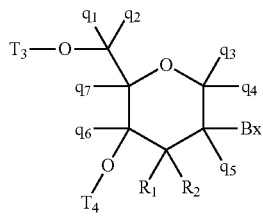

wherein independently for each of said at least one tetrahydropyran nucleoside analog of Formula III:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $R_1$ and $R_2$ is fluoro and the other of $R_1$ and $R_2$ is H, halogen, $C_1$-$C_6$ alkyl or substituted $C_1$-$C_6$ alkyl;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein said oligomeric compound comprises from about 8 to about 40 monomeric subunits.

In certain embodiments, the other of $R_1$ and $R_2$ is H. In certain embodiments, $R_1$ and $R_2$ are each fluoro. In certain embodiments, the other of $R_1$ and $R_2$ is $C_1$-$C_6$ alkyl or substituted $C_1$-$C_6$ alkyl. In certain embodiments, the other of $R_1$ and $R_2$ is methyl, ethyl, substituted methyl or substituted ethyl. In certain embodiments, the other of $R_1$ and $R_2$ is methyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is $C_1$-$C_6$ alkyl or substituted $C_1$-$C_6$ alkyl. In certain embodiments, at least one of $q_1$, $q_2$, $q_3$, $q_4$, $q_5$, $q_6$ and $q_7$ is methyl. In certain embodiments, at least one of $q_1$ and $q_2$ is methyl. In certain embodiments, at least one of $q_3$ and $q_4$ is methyl. In certain embodiments, at least one of $q_5$, $q_6$ and $q_7$ is methyl.

In certain embodiments, at least one of $T_3$ and $T_4$ is a linked conjugate group.

In certain embodiments, each internucleoside linking group is, independently, a phosphodiester or a phosphorothioate internucleoside linking group. In certain embodiments, each internucleoside linking group is a phosphorothioate internucleoside linking group.

In certain embodiments, each Bx is, independently, uracil, thymine, cytosine, adenine or guanine. In certain embodiments, each Bx is, independently, a pyrimidine, substituted pyrimidine, purine or substituted purine wherein said substitution is other than an intercalator or a linked group that does not interact with a nucleic acid target. In certain embodiments, Bx is, independently, uracil, 5-methyluracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4]benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',':4,5]pyrrolo[2,3-d]pyrimidin-2-one. In certain embodiments, each Bx is, independently, uracil, 5-methyluracil, 5-propynyl-uracil, thymine, cytosine, 5-methylcytosine, 5-propynyl-cytosine, adenine or guanine.

In certain embodiments, each tetrahydropyran nucleoside analog of Formula III has the configuration shown in Formula IIIa:

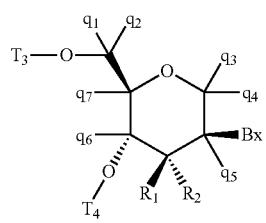

wherein

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $R_1$ and $R_2$ is fluoro and the other of $R_1$ and $R_2$ is H, halogen, $C_1$-$C_6$ alkyl or substituted $C_1$-$C_6$ alkyl;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein the oligomeric compound comprises from about 8 to about 40 nucleosides, modified nucleosides and or tetrahydropyran nucleoside analogs.

In certain embodiments, tetrahydropyran nucleoside analogs are provided having Formula IIIa wherein $R_2$ is fluoro. In certain embodiments, tetrahydropyran nucleoside analogs are provided having Formula IIIa wherein $R_2$ is fluoro and $R_1$ is H. In certain embodiments, tetrahydropyran nucleoside analogs are provided having Formula IIIa wherein $R_2$ is fluoro, $R_1$ is H and $q_1$, $q_2$, $q_3$, $q_4$, $q_5$, $q_6$ and $q_7$ are each H.

In certain embodiments, oligomeric compounds are provided wherein each tetrahydropyran nucleoside analog has Formula IV:

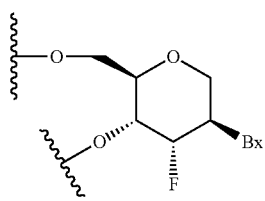

IV wherein:

Bx is a heterocyclic base moiety.

In certain embodiments, oligomeric compounds are provided having at least one contiguous region of from 1 to about 5 tetrahydropyran nucleoside analogs wherein each tetrahydropyran nucleoside analog has Formula IIIa. In certain embodiments, oligomeric compounds are provided having at least one contiguous region of from 1 to about 5 tetrahydropyran nucleoside analogs wherein each tetrahydropyran nucleoside analog has Formula IIIa and the oligomeric compound comprises a blockmer. In certain embodiments, oligomeric compounds are provided having at least one contiguous region of from 1 to about 5 tetrahydropyran nucleoside analogs wherein each tetrahydropyran nucleoside analog has Formula IIIa and the oligomeric compound comprises a 3' or 5'-hemimer.

In certain embodiments, oligomeric compounds are provided having at least one contiguous region of from 1 to about 5 tetrahydropyran nucleoside analogs wherein each tetrahydropyran nucleoside analog has Formula IV:

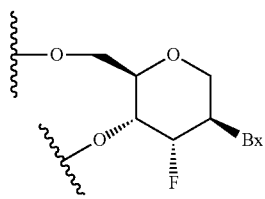

IV wherein:

Bx is a heterocyclic base moiety.

In certain embodiments, oligomeric compounds are provided having at least two regions of from 1 to about 5 contiguous tetrahydropyran nucleoside analogs having Formula IIIa that are separated by at least one nucleoside or modified nucleoside. In certain embodiments, oligomeric compounds are provided having at least two regions of from 1 to about 5 contiguous tetrahydropyran nucleoside analogs having Formula IIIa comprising a gapped oligomeric compound wherein one of said at least two regions of tetrahydropyran nucleoside analogs is located at the 5'-end and the other region of said at least two regions of tetrahydropyran nucleoside analogs is located at the 3'-end and wherein the two regions of tetrahydropyran nucleoside analogs are separated by an internal region comprising from about 6 to about 14 monomeric subunits independently selected from nucleosides, modified nucleosides and tetrahydropyran nucleoside analogs. In certain embodiments, essentially each monomeric subunit in the internal region is a β-D-2'-deoxyribonucleoside. In certain embodiments, the internal region comprises from about 6 to about 14 β-D-2'-deoxyribonucleosides. In certain embodiments, the internal region comprises from about 10 to about 12 β-D-2'-deoxyribonucleosides. In certain embodiments, the internal region comprises from about 10 to about 14 β-D-2'-deoxyribonucleosides.

In certain embodiments, oligomeric compounds are provided having at least two regions of from about 2 to about 3 contiguous tetrahydropyran nucleoside analogs having Formula IIIa comprising a gapped oligomeric compound wherein one of said at least two regions of tetrahydropyran nucleoside analogs is located at the 5'-end and the other region of said at least two regions of tetrahydropyran nucleoside analogs is located at the 3'-end and wherein the two regions of tetrahydropyran nucleoside analogs are separated by an internal region comprising from about 6 to about 14 monomeric subunits independently selected from nucleosides, modified nucleosides and tetrahydropyran nucleoside analogs. In certain embodiments, each region of tetrahydropyran nucleoside analogs independently comprises 2 tetrahydropyran nucleoside analogs. In certain embodiments, each region of tetrahydropyran nucleoside analogs independently comprises 2 tetrahydropyran nucleoside analogs and the internal region comprises 10 β-D-2'-deoxyribonucleosides.

In certain embodiments, gapped oligomeric compounds are provided wherein each region of tetrahydropyran nucleoside analogs independently comprises 2 tetrahydropyran nucleoside analogs and the internal region comprises 10 β-D-2'-deoxyribonucleosides and each tetrahydropyran nucleoside analog has Formula IV:

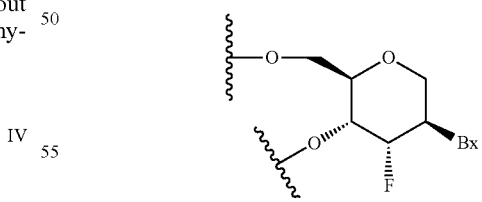

IV wherein:

Bx is a heterocyclic base moiety.

In certain embodiments, oligomeric compounds are provided having at least two regions of from about 2 to about 3 contiguous tetrahydropyran nucleoside analogs having Formula IIIa comprising a gapped oligomeric compound wherein one of said at least two regions of tetrahydropyran nucleoside analogs is located at the 5'-end and the other region of said at least two regions of tetrahydropyran nucleoside analogs is located at the 3'-end and wherein the two regions of tetrahydropyran nucleoside analogs are separated by an internal region comprising 14 β-D-2'-deoxyribonucleosides. In certain embodiments, each region of tetrahydropyran nucleoside analogs independently comprises 2 tetrahydropyran nucleoside analogs. In certain embodiments, each tetrahydropyran nucleoside analog has Formula IV:

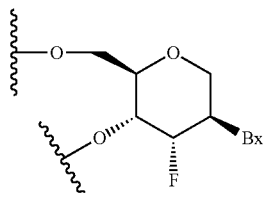

IV wherein:

Bx is a heterocyclic base moiety.

In certain embodiments, gapped oligomeric compounds are provided further comprising a 3'-terminal group. In certain embodiments, the 3'-terminal group comprises from 1 to about 4 modified or unmodified nucleosides.

In certain embodiments, oligomeric compounds are provided comprising from about 10 to about 21 monomer subunits in length. In certain embodiments, oligomeric compounds are provided comprising from about 10 to about 16 monomer subunits in length. In certain embodiments, oligomeric compounds are provided comprising from about 10 to about 14 monomer subunits in length.

In certain embodiments, oligomeric compounds comprising at least two contiguous tetrahydropyran nucleoside analogs of Formula V are provided:

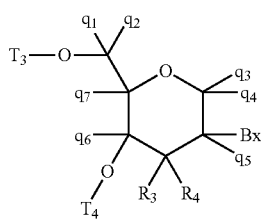

V wherein independently for each of said tetrahydropyran nucleoside analogs of Formula V:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$;

said oligomeric compound comprises from about 8 to about 40 monomeric subunits; and wherein at least two of said at least two contiguous tetrahydropyran nucleoside analogs are linked by an internucleoside linking group that is other than a phosphodiester internucleoside linking group.

In certain embodiments, at least one of $q_1$, $q_2$, $q_3$, $q_4$, $q_5$, $q_6$ and $q_7$ is $C_1$-$C_6$ alkyl or substituted $C_1$-$C_6$ alkyl. In certain embodiments, at least one of $q_1$, $q_2$, $q_3$, $q_4$, $q_5$, $q_6$ and $q_7$ is methyl. In certain embodiments, at least one of $q_1$ and $q_2$ is methyl. In certain embodiments, at least one of $q_3$ and $q_4$ is methyl. In certain embodiments, at least one of $q_5$, $q_6$ and $q_7$ is methyl.

In certain embodiments, $q_1$, $q_2$, $q_3$, $q_4$, $q_5$, $q_6$ and $q_7$ are each H. In certain embodiments, $q_1$, $q_2$, $q_3$, $q_4$, $q_5$, $q_6$ and $q_7$ are each H and $R_3$ is H. In certain embodiments, $q_1$, $q_2$, $q_3$, $q_4$, $q_5$, $q_6$ and $q_7$ are each H, $R_3$ is H and $R_4$ is H. In certain embodiments, $q_1$, $q_2$, $q_3$, $q_4$, $q_5$, $q_6$ and $q_7$ are each H, $R_3$ is H and $R_4$ is $OCH_3$. In certain embodiments, $q_1$, $q_2$, $q_3$, $q_4$, $q_5$, $q_6$ and $q_7$ are each H, $R_3$ is H and $R_4$ is fluoro. In certain embodiments, $q_1$, $q_2$, $q_3$, $q_4$, $q_5$, $q_6$ and $q_7$ are each H, $R_3$ is H and $R_4$ is hydroxyl. In certain embodiments, $q_1$, $q_2$, $q_3$, $q_4$, $q_5$, $q_6$ and $q_7$ are each H, $R_3$ is H and each $R_4$ is H, $OCH_3$, fluoro or hydroxyl.

In certain embodiments, oligomeric compounds are provided comprising at least two contiguous tetrahydropyran nucleoside analogs of Formula V wherein at least one of $T_3$ and $T_4$ is a linked conjugate group and wherein at least two of said at least two contiguous tetrahydropyran nucleoside analogs are linked by an internucleoside linking group that is other than a phosphodiester internucleoside linking group. In certain embodiments, at least two of said at least two contiguous tetrahydropyran nucleoside analogs are linked by a phosphorothioate internucleoside linking group. In certain embodiments, at least two of said at least two contiguous tetrahydropyran nucleoside analogs are linked by a phosphorus containing internucleoside linking group. In certain embodiments, at least two of said at least two contiguous tetrahydropyran nucleoside analogs are linked by a non phosphorus containing internucleoside linking group. In certain embodiments, at least two of said at least two contiguous tetrahydropyran nucleoside analogs are linked by a neutral internucleoside linking group. In certain embodiments, each internucleoside linking group is independently a phosphodiester or a phosphorothioate internucleoside linking group. In certain embodiments, each internucleoside linking group is a phosphorothioate internucleoside linking group.

In certain embodiments, oligomeric compounds are provided comprising at least two contiguous tetrahydropyran nucleoside analogs of Formula V wherein at least two of said at least two contiguous tetrahydropyran nucleoside analogs are linked by an internucleoside linking group that is other than a phosphodiester internucleoside linking group and wherein each Bx is, independently, uracil, thymine, cytosine, adenine or guanine. In certain embodiments, each Bx is, independently, a pyrimidine, substituted pyrimidine, purine or substituted purine wherein said substitution is other than an intercalator or a linked group that does not interact with a nucleic acid target. In certain embodiments, each Bx is, independently, uracil, 5-methyluracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4]benzoxazin-2(3H)-one, 1H-pyrimido[5,4-b][1,4]benzothiazin-2(3H)-one, 9-(2-aminoethoxy)-H-pyrimido[5,4-b]

[1,4]benzoxazin-2(3H)-one, 2H-pyrimido[4,5-b]indol-2-one or H-pyrido[3',:4,5]pyrrolo[2,3-d]pyrimidin-2-one. In certain embodiments, each Bx is, independently, uracil, 5-methyluracil, 5-propynyl-uracil, thymine, cytosine, 5-methylcytosine, 5-propynyl-cytosine, adenine or guanine.

In certain embodiments, oligomeric compounds are provided comprising at least two contiguous tetrahydropyran nucleoside analogs of Formula V wherein at least two of said at least two contiguous tetrahydropyran nucleoside analogs are linked by an internucleoside linking group that is other than a phosphodiester internucleoside linking group and wherein each tetrahydropyran nucleoside analog of Formula V has the configuration shown in formula Va:

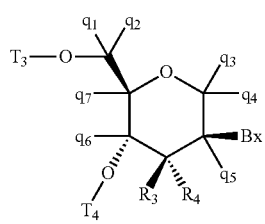

Va

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy; and each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, oligomeric compounds are provided comprising at least two contiguous tetrahydropyran nucleoside analogs of Formula Va wherein at least two of said at least two contiguous tetrahydropyran nucleoside analogs are linked by an internucleoside linking group that is other than a phosphodiester internucleoside linking group and wherein the oligomeric compound comprises at least one contiguous region of from 1 to about 5 tetrahydropyran nucleoside analogs. In certain embodiments, the oligomeric compound comprises a blockmer. In certain embodiments, the oligomeric compound comprises a 3' or 5'-hemimer.

In certain embodiments, oligomeric compounds are provided comprising at least two contiguous tetrahydropyran nucleoside analogs of Formula Va wherein at least two of said at least two contiguous tetrahydropyran nucleoside analogs are linked by an internucleoside linking group that is other than a phosphodiester internucleoside linking group and wherein the oligomeric compound comprises at least two regions of from 1 to about 5 contiguous tetrahydropyran nucleoside analogs that are separated by at least one nucleoside or modified nucleoside. In certain embodiments, the oligomeric compound comprises a gapped oligomeric compound wherein one external region of tetrahydropyran nucleoside analogs is located at the 5'-end and a second external region of tetrahydropyran nucleoside analogs is located at the 3'-end wherein the two external regions are separated by an internal region comprising from about 6 to about 14 monomeric subunits independently selected from nucleosides, modified nucleosides and tetrahydropyran nucleoside analogs. In certain embodiments, essentially each monomeric subunit in the internal region is a β-D-2'-deoxyribonucleoside. In certain embodiments, the internal region comprises from about 6 to about 14 β-D-2'-deoxyribonucleosides. In certain embodiments, the internal region comprises from about 10 to about 12 β-D-2'-deoxyribonucleosides. In certain embodiments, the internal region comprises from about 10 to about 14 β-D-2'-deoxyribonucleosides. In certain embodiments, each external region independently comprises from 2 to about 3 tetrahydropyran nucleoside analogs. In certain embodiments, each external region independently comprises 2 tetrahydropyran nucleoside analogs. In certain embodiments, each external region independently comprises 2 tetrahydropyran nucleoside analogs and the internal region comprises 10 β-D-2'-deoxyribonucleosides.

In certain embodiments, oligomeric compounds are provided comprising at least two contiguous tetrahydropyran nucleoside analogs of Formula V wherein at least two of said at least two contiguous tetrahydropyran nucleoside analogs are linked by an internucleoside linking group that is other than a phosphodiester internucleoside linking group and wherein each tetrahydropyran nucleoside analog has the Formula and configuration shown in Formula Vb:

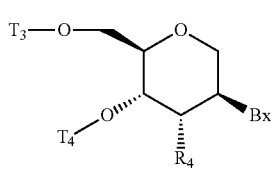

Vb wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group; and $R_4$ is H, hydroxyl, fluoro or $OCH_3$.

In certain embodiments, oligomeric compounds are provided comprising at least two contiguous tetrahydropyran nucleoside analogs of Formula V wherein at least two of said at least two contiguous tetrahydropyran nucleoside analogs are linked by an internucleoside linking group that is other than a phosphodiester internucleoside linking group and wherein each tetrahydropyran nucleoside analog has Formula Vb and $R_4$ H. In certain embodiments, $R_4$ is hydroxyl. In certain embodiments, $R_4$ is $OCH_3$. In certain embodiments, $R_4$ is fluoro.

In certain embodiments, oligomeric compounds are provided comprising at least two contiguous tetrahydropyran nucleoside analogs of Formula V wherein at least two of said at least two contiguous tetrahydropyran nucleoside analogs are linked by an internucleoside linking group that is other than a phosphodiester internucleoside linking group and wherein each oligomeric compound comprises from about 10 to about 21 monomer subunits in length. In certain embodiments, each oligomeric compound comprises from about 10 to about 16 monomer subunits in length. In certain embodiments, each oligomeric compound comprises from about 10 to about 14 monomer subunits in length.

In certain embodiments, methods are provided comprising contacting a cell in an animal with an oligomeric compound, said oligomeric compound comprising at least one tetrahydropyran nucleoside analog of Formula V:

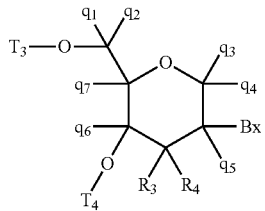

V wherein independently for each of said at least one tetrahydropyran nucleoside analog of Formula V:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein said oligomeric compound comprises from about 8 to about 40 monomeric subunits and is complementary to a target RNA.

In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function.

In certain embodiments, the method further comprises evaluating the antisense activity of the oligomeric compound on said cell. In certain embodiments, the evaluating comprises detecting the levels of target RNA. In certain embodiments, the evaluating comprises detecting the levels of a protein. In certain embodiments, the evaluating comprises detection of one or more phenotypic effects.

In certain embodiments, methods are provided comprising contacting a cell in an animal with an oligomeric compound, said oligomeric compound comprising at least one tetrahydropyran nucleoside analog of Formula V wherein $q_1$, $q_2$, $q_3$, $q_4$, $q_5$, $q_6$ and $q_7$ are each H. In certain embodiments, $q_1$, $q_2$, $q_3$, $q_4$, $q_5$, $q_6$ and $q_7$ are each H and $R_3$ is H. In certain embodiments, $q_1$, $q_2$, $q_3$, $q_4$, $q_5$, $q_6$ and $q_7$ are each H, $R_3$ is H and $R_4$ is $OCH_3$. In certain embodiments, $q_1$, $q_2$, $q_3$, $q_4$, $q_5$, $q_6$ and $q_7$ are each H, $R_3$ is H and $R_4$ is fluoro. In certain embodiments, $q_1$, $q_2$, $q_3$, $q_4$, $q_5$, $q_6$ and $q_7$ are each H, $R_3$ is H and $R_4$ is hydroxyl. In certain embodiments, $q_1$, $q_2$, $q_3$, $q_4$, $q_5$, $q_6$ and $q_7$ are each H, $R_3$ is H and each $R_4$ is H, $OCH_3$, fluoro or hydroxyl.

In certain embodiments, methods are provided comprising contacting a cell in an animal with an oligomeric compound, said oligomeric compound comprising at least one tetrahydropyran nucleoside analog of Formula V wherein each internucleoside linking group is independently a phosphodiester or a phosphorothioate internucleoside linking group. In certain embodiments, each internucleoside linking group is a phosphorothioate internucleoside linking group.

In certain embodiments, methods are provided comprising contacting a cell in an animal with an oligomeric compound, said oligomeric compound comprising at least one tetrahydropyran nucleoside analog of Formula V wherein each tetrahydropyran nucleoside analog of Formula V has the configuration shown in Formula Vb:

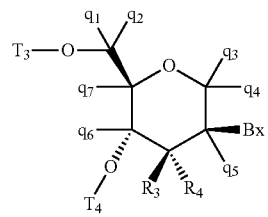

V wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy; and each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, methods are provided comprising contacting a cell in an animal with an oligomeric compound, said oligomeric compound comprising at least one tetrahydropyran nucleoside analog wherein the oligomeric compound comprises at least one contiguous region of from 1 to about 5 tetrahydropyran nucleoside analogs having Formula Va. In certain embodiments, the oligomeric compound is a blockmer. In certain embodiments, the oligomeric compound is a 3' or 5'-hemimer.

In certain embodiments, methods are provided comprising contacting a cell in an animal with an oligomeric compound, said oligomeric compound comprising at least two regions of from 1 to about 5 contiguous tetrahydropyran nucleoside analogs that are separated by at least one nucleoside or modified nucleoside. In certain embodiments, the oligomeric compound comprises a gapped oligomeric compound wherein one external region of tetrahydropyran nucleoside analogs is located at the 5'-end and a second external region of tetrahydropyran nucleoside analogs is located at the 3'-end wherein the two external regions are separated by an internal region comprising from about 6 to about 14 monomeric subunits independently selected from nucleosides, modified nucleosides and tetrahydropyran nucleoside analogs. In certain embodiments, each monomeric subunit in the internal region is a β-D-2'-deoxyribonucleoside. In certain embodiments, the internal region comprises from about 6 to about 14 β-D-2'-deoxyribonucleosides. In certain embodiments, the internal region comprises from about 10 to about 12 β-D-2'-deoxyribonucleosides. In certain embodiments, the internal region comprises from about 10 to about 14 β-D-2'-deoxyribonucleosides. In certain embodiments, each external region independently comprises from 2 to about 3 tetrahydropyran nucleoside analogs. In certain embodiments, each external region independently comprises 2 tetrahydropyran nucleoside analogs. In certain embodiments, each external region independently comprises 2 tetrahydropyran nucleoside analogs and the internal region comprises 10 β-D-2'-deoxyribonucleosides.

In certain embodiments, methods are provided comprising contacting a cell in an animal with an oligomeric compound, said oligomeric compound comprising at least one tetrahydropyran nucleoside analog of Formula V wherein each tetrahydropyran nucleoside analog has the Formula and configuration shown in FIG. Vb:

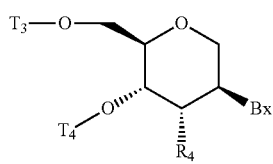

Vb wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group; and $R_4$ is H, hydroxyl, fluoro or $OCH_3$. In certain embodiments, $R_4$ is H. In certain embodiments, $R_4$ is hydroxyl. In certain embodiments, $R_4$ is $OCH_3$. In certain embodiments, $R_4$ is fluoro.

In certain embodiments, methods are provided comprising contacting a cell with an oligomeric compound, said oligomeric compound comprising at least two contiguous tetrahydropyran nucleoside analogs of Formula V:

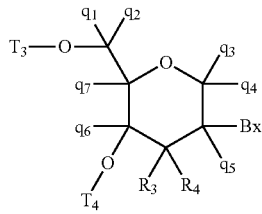

V wherein independently for each of said tetrahydropyran nucleoside analogs of Formula V:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1, q_2, q_3, q_4, q_5, q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$;

said oligomeric compound comprises from about 8 to about 40 monomeric subunits and is complementary to a target RNA; and wherein at least two of said two contiguous tetrahydropyran nucleoside analogs are linked by an internucleoside linking group that is other than a phosphodiester internucleoside linking group. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function.

In certain embodiments, the method further comprises evaluating the antisense activity of said oligomeric compound on said cell. In certain embodiments, the evaluating comprises detecting the levels of target RNA. In certain embodiments, the evaluating comprises detecting the levels of a protein. In certain embodiments, the evaluating comprises detection of one or more phenotypic effects.

In certain embodiments, methods are provided comprising contacting a cell with an oligomeric compound comprising at least two contiguous tetrahydropyran nucleoside analogs of Formula V wherein at least two of the tetrahydropyran nucleoside analogs are linked by an internucleoside linking group that is other than a phosphodiester internucleoside linking group and wherein $q_1, q_2, q_3, q_4, q_5, q_6$ and $q_7$ are each H. In certain embodiments, $R_3$ is H. In certain embodiments, $R_4$ is $OCH_3$. In certain embodiments, $R_4$ is fluoro. In certain embodiments, $R_4$ is hydroxyl. In certain embodiments, each $R_4$ is $OCH_3$, fluoro or hydroxyl.

In certain embodiments, methods are provided comprising contacting a cell with an oligomeric compound comprising at least two contiguous tetrahydropyran nucleoside analogs of Formula V wherein at least two of the tetrahydropyran nucleoside analogs are linked by an internucleoside linking group that is other than a phosphodiester internucleoside linking group and wherein at least two of the tetrahydropyran nucleoside analogs are linked by a phosphorothioate internucleoside linkage. In certain embodiments, at least two of said at least two contiguous tetrahydropyran nucleoside analogs are linked by a phosphorus containing internucleoside linkage other than a phosphodiester internucleoside linkage. In certain embodiments, at least two of said at least two contiguous tetrahydropyran nucleoside analogs are linked by a non phosphorus containing internucleoside linkage. In certain embodiments, at least two of said at least two contiguous tetrahydropyran nucleoside analogs are linked by a neutral internucleoside linkage. In certain embodiments, each internucleoside linking group is independently a phosphodiester or a phosphorothioate internucleoside linking group. In certain embodiments, each internucleoside linking group is a phosphorothioate internucleoside linking group.

In certain embodiments, methods are provided comprising contacting a cell with an oligomeric compound comprising at least two contiguous tetrahydropyran nucleoside analogs wherein at least two of the tetrahydropyran nucleoside analogs are linked by an internucleoside linking group that is other than a phosphodiester internucleoside linking group and wherein each tetrahydropyran nucleoside analog of Formula V has the configuration shown in Formula Vb:

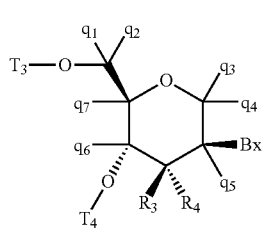

Vb wherein:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy; and
each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, methods are provided comprising contacting a cell with an oligomeric compound comprising at least two contiguous tetrahydropyran nucleoside analogs wherein at least two of the tetrahydropyran nucleoside analogs are linked by an internucleoside linking group that is other than a phosphodiester internucleoside linking group and wherein the oligomeric compound of claim comprises at least one contiguous region of from 1 to about 5 tetrahydropyran nucleoside analogs having Formula Vb. In certain embodiments, the oligomeric compound comprises a blockmer. In certain embodiments, the oligomeric compound comprises a 3' or 5'-hemimer.

In certain embodiments, methods are provided comprising contacting a cell with an oligomeric compound comprising at least two contiguous tetrahydropyran nucleoside analogs wherein at least two of the tetrahydropyran nucleoside analogs are linked by an internucleoside linking group that is other than a phosphodiester internucleoside linking group and wherein the oligomeric compound of claim comprises at least two contiguous regions of from 1 to about 5 tetrahydropyran nucleoside analogs having Formula Vb wherein the regions are separated by at least one nucleoside or modified nucleoside. In certain embodiments, the oligomeric compound comprises a gapped oligomeric compound wherein one external region of tetrahydropyran nucleoside analogs is located at the 5'-end and a second external region of tetrahydropyran nucleoside analogs is located at the 3'-end wherein the two external regions are separated by an internal region comprising from about 6 to about 14 monomeric subunits independently selected from nucleosides, modified nucleosides and tetrahydropyran nucleoside analogs. In certain embodiments, each monomeric subunit in the internal region is a β-D-2'-deoxyribonucleoside. In certain embodiments, the internal region comprises from about 6 to about 14 β-D-2'-deoxyribonucleosides. In certain embodiments, the internal region comprises from about 10 to about 12 β-D-2'-deoxyribonucleosides. In certain embodiments, the internal region comprises from about 10 to about 14 β-D-2'-deoxyribonucleosides. In certain embodiments, each external region independently comprises from 2 to about 3 tetrahydropyran nucleoside analogs. In certain embodiments, each external region independently comprises 2 tetrahydropyran nucleoside analogs. In certain embodiments, each external region independently comprises 2 tetrahydropyran nucleoside analogs and the internal region comprises 10 β-D-2'-deoxyribonucleosides.

In certain embodiments, methods are provided comprising contacting a cell with an oligomeric compound comprising at least two contiguous tetrahydropyran nucleoside analogs wherein at least two of the tetrahydropyran nucleoside analogs are linked by an internucleoside linking group that is other than a phosphodiester internucleoside linking group and wherein each tetrahydropyran nucleoside analog has Formula V and configuration shown in Formula Vb shown below:

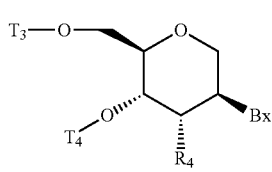

Vb wherein
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group; and $R_4$ is H, hydroxyl, fluoro or $OCH_3$. In certain embodiments, $R_4$ is H. In certain embodiments, $R_4$ is hydroxyl. In certain embodiments, $R_4$ is $OCH_3$. In certain embodiments, $R_4$ is fluoro.

In certain embodiments, methods of reducing target messenger RNA are provided comprising contacting one or more cells, a tissue or an animal with an oligomeric compound comprising at least one tetrahydropyran nucleoside analog of Formula V:

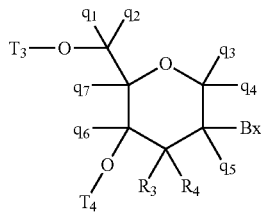

V

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1, q_2, q_3, q_4, q_5, q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein the oligomeric compound comprises from about 8 to about 40 nucleosides, modified nucleosides and or tetrahydropyran nucleoside analogs. In certain embodiments, $q_1, q_2, q_3, q_4, q_5, q_6$ and are each H. In certain embodiments, $q_1, q_2, q_3, q_4, q_5, q_6$ and $q_7$ are each H and $R_3$ is H In certain embodiments, $q_1, q_2, q_3, q_4, q_5, q_6$ and $q_7$ are each H. In certain embodiments, $q_1, q_2, q_3, q_4, q_5, q_6$ and $q_7$ are each H, $R_3$ is H and $R_4$ is $OCH_3$. In certain embodiments, $q_1, q_2, q_3, q_4, q_5, q_6$ and $q_7$ are each H, $R_3$ is H and $R_4$ is fluoro. In certain embodiments, $q_1, q_2, q_3, q_4, q_5, q_6$ and $q_7$ are each H, $R_3$ is H and $R_4$ is hydroxyl. In certain embodiments, $q_1, q_2, q_3, q_4, q_5, q_6$ and $q_7$ are each H, $R_3$ is H and each $R_4$ is H, $OCH_3$, fluoro or hydroxyl.

In certain embodiments, methods of reducing target messenger RNA are provided comprising contacting one or more cells, a tissue or an animal with an oligomeric compound comprising at least one tetrahydropyran nucleoside analog of Formula V wherein each internucleoside linking group is, independently, a phosphodiester or a phosphorothioate internucleoside linking group. In certain embodiments, each internucleoside linking group is a phosphorothioate internucleoside linking group.

In certain embodiments, methods of reducing target messenger RNA are provided comprising contacting one or more cells, a tissue or an animal with an oligomeric compound comprising at least one tetrahydropyran nucleoside analog wherein each tetrahydropyran nucleoside analog has the Formula Vb:

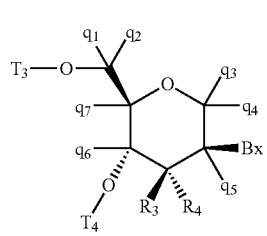

Vb

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1, q_2, q_3, q_4, q_5, q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy; and each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, methods of reducing target messenger RNA are provided comprising contacting one or more cells, a tissue or an animal with an oligomeric compound comprising at least one tetrahydropyran nucleoside comprising at least one contiguous region of from 1 to about 5 tetrahydropyran nucleoside analogs and wherein each tetrahydropyran nucleoside analog has Formula Vb. In certain embodiments, the oligomeric compound comprises a blockmer. In certain embodiments, the oligomeric compound comprises a 3' or 5'-hemimer.

In certain embodiments, methods of reducing target messenger RNA are provided comprising contacting one or more cells, a tissue or an animal with an oligomeric compound comprising at least two regions of from 1 to about 5 contiguous tetrahydropyran nucleoside analogs that are separated by at least one nucleoside or modified nucleoside and wherein each tetrahydropyran nucleoside analog has Formula Vb. In certain embodiments, the oligomeric compound comprises a gapped oligomeric compound wherein one external region of tetrahydropyran nucleoside analogs is located at the 5'-end and a second external region of tetrahydropyran nucleoside analogs is located at the 3'-end wherein the two external regions are separated by an internal region comprising from about 6 to about 14 monomeric subunits independently selected from nucleosides, modified nucleosides and tetrahydropyran nucleoside analogs. In certain embodiments, essentially each monomeric subunit in the internal region is a β-D-2'-deoxyribonucleoside. In certain embodiments, the internal region comprises from about 6 to about 14 β-D-2'-deoxyribonucleosides. In certain embodiments, the internal region comprises from about 10 to about 12 β-D-2'-deoxyribonucleosides. In certain embodiments, the external region independently comprises from 2 to about 3 tetrahydropyran nucleoside analogs. In certain embodiments, each external region independently comprises 2 tetrahydropyran nucleoside analogs. In certain embodiments, each external region independently comprises 2 tetrahydropyran nucleoside analogs and the internal region comprises 10 β-D-2'-deoxyribonucleosides.

In certain embodiments, methods of reducing target messenger RNA are provided comprising contacting one or more cells, a tissue or an animal with an oligomeric compound comprising at least one tetrahydropyran nucleoside analog wherein each tetrahydropyran nucleoside analog has Formula Vb:

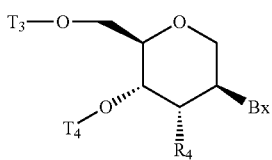

wherein

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group; and $R_4$ is hydroxyl, fluoro or $OCH_3$. In certain embodiments, $R_4$ is hydroxyl. In certain embodiments, $R_4$ is $OCH_3$. In certain embodiments, $R_4$ is fluoro.

In certain embodiments, tetrahydropyran nucleoside analogs are provided having Formula I:

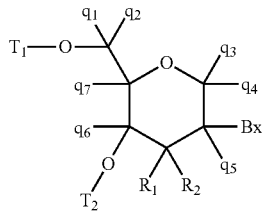

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

each $q_1$, $q_2$, $q_3$, $q_4$, $q_5$, $q_6$ and $q_7$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $R_1$ and $R_2$ is fluoro and the other of $R_1$ and $R_2$ is H, halogen, $C_1$-$C_6$ alkyl or substituted $C_1$-$C_6$ alkyl; and wherein each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, one of $R_1$ and $R_2$ is fluoro and the other of $R_1$ and $R_2$ is H. In certain embodiments, $R_1$ and $R_2$ are each fluoro. In certain embodiments, one of $R_1$ and $R_2$ is fluoro and the other of $R_1$ and $R_2$ is $C_1$-$C_6$ alkyl or substituted $C_1$-$C_6$ alkyl. In certain embodiments, one of $R_1$ and $R_2$ is fluoro and the other of $R_1$ and $R_2$ is methyl, ethyl, substituted methyl or substituted ethyl. In certain embodiments, one of $R_1$ and $R_2$ is fluoro and the other of $R_1$ and $R_2$ is methyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is $C_1$-$C_6$ alkyl or substituted $C_1$-$C_6$ alkyl. In certain embodiments, at least one of $q_1$, $q_2$, $q_3$, $q_4$, $q_5$, $q_6$ and $q_7$ is methyl. In certain embodiments, at least one of $q_1$ and $q_2$ is methyl. In certain embodiments, at least one of $q_3$ and $q_4$ is methyl. In certain embodiments, at least one of $q_5$, $q_6$ and $q_7$ is methyl.

In certain embodiments, $T_1$ and $T_2$ are each H. In certain embodiments, at least one of $T_1$ and $T_2$ is a hydroxyl protecting group. In certain embodiments, each hydroxyl protecting group is, independently, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4-methoxytrityl, 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl, dimethoxytrityl, trimethoxytrityl or substituted pixyl. In certain embodiments, $T_1$ is acetyl, benzyl, t-butyldimethylsilyl, t-butyldiphenylsilyl, 4-methoxytrityl or 4,4'-dimethoxytrityl. In certain embodiments, one of $T_1$ and $T_2$ is a hydroxyl protecting group and the other of $T_1$ and $T_2$ is diisopropylcyanoethoxy phosphoramidite or H-phosphonate. In certain embodiments, $T_1$ is 4,4'-dimethoxytrityl and $T_2$ is diisopropylcyanoethoxy phosphoramidite.

In certain embodiments, Bx is uracil, thymine, cytosine, adenine or guanine. In certain embodiments, Bx is a pyrimidine, substituted pyrimidine, purine or substituted purine wherein said substitution is other than an intercalator or a linked group that does not interact with a nucleic acid target when the tetrahydropyran nucleoside analog is located in an oligomeric compound. In certain embodiments, Bx is uracil, 5-methyluracil, 5-thiazolo-uracil, 2-thio-uracil, 5-propynyl-uracil, thymine, 2'-thio-thymine, cytosine, 5-methyl-cytosine, 5-thiazolo-cytosine, 5-propynyl-cytosine, adenine, guanine, 2,6-diaminopurine, 1H-pyrimido[5,4-b][1,4]benzoxazin-2(3H)-one, 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',':4,5]-pyrrolo[2,3-d]pyrimidin-2-one. In certain embodiments, Bx is uracil, 5-methyluracil, 5-propynyl-uracil, thymine, cytosine, 5-methylcytosine, 5-propynyl-cytosine, adenine or guanine.

In certain embodiments, tetrahydropyran nucleoside analogs are provided having the configuration shown in Formula Ia:

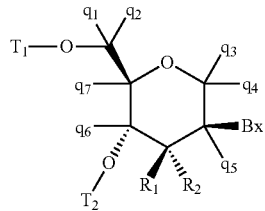

wherein:

Bx is a heterocyclic base moiety;

one of $T_1$ and $T_2$ is H or a hydroxyl protecting group and the other of $T_1$ and $T_2$ is H, a hydroxyl protecting group or a reactive phosphorus group;

each $q_1$, $q_2$, $q_3$, $q_4$, $q_5$, $q_6$ and $q_7$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $R_1$ and $R_2$ is fluoro and the other of $R_1$ and $R_2$ is H, halogen, $C_1$-$C_6$ alkyl or substituted $C_1$-$C_6$ alkyl; and wherein each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, a tetrahydropyran nucleoside analog is provided having the configuration shown in Formula Ia wherein $R_2$ is fluoro. In certain embodiments, a tetrahydropyran nucleoside analog is provided having the configuration shown in Formula Ia wherein $R_1$ is H and $R_2$ is fluoro. In certain embodiments, a tetrahydropyran nucleoside analog is provided having the configuration shown in Formula Ia wherein $R_1$ is H, $R_2$ is fluoro and $q_1$, $q_2$, $q_3$, $q_4$, $q_5$, $q_6$ and $q_7$ are each H.

In certain embodiments, a tetrahydropyran nucleoside analog is provided having the configuration shown in Formula Ia wherein $R_1$ is $C_1$-$C_6$ alkyl or substituted $C_1$-$C_6$ alkyl and $R_2$ is fluoro. In certain embodiments, a tetrahydropyran nucleoside analog is provided having the configuration shown in Formula Ia wherein $R_1$ is methyl, ethyl, substituted methyl or substituted ethyl and $R_2$ is fluoro.

In certain embodiments, a tetrahydropyran nucleoside analog is provided having the configuration shown in Formula Ia wherein $R_1$ and $R_2$ are each fluoro.

In certain embodiments, oligomeric compounds each comprising at least one tetrahydropyran nucleoside analog of Formula II are provided:

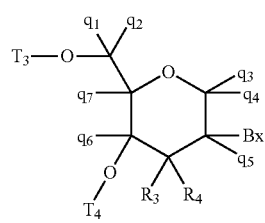

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a protecting group, a linked conjugate group or a 5' or 3'-terminal group;

each $q_1$, $q_2$, $q_3$, $q_4$, $q_5$, $q_6$ and $q_7$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $R_1$ and $R_2$ is fluoro and the other of $R_1$ and $R_2$ is H, halogen, $C_1$-$C_6$ alkyl or substituted $C_1$-$C_6$ alkyl;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein the oligomeric compound comprises from about 8 to about 40 nucleosides, modified nucleosides and or tetrahydropyran nucleoside analogs.

In certain embodiments, one of $R_1$ and $R_2$ is fluoro and the other of $R_1$ and $R_2$ is H. In certain embodiments, $R_1$ and $R_2$ are each fluoro. In certain embodiments, one of $R_1$ and $R_2$ is fluoro and the other of $R_1$ and $R_2$ is $C_1$-$C_6$ alkyl or substituted $C_1$-$C_6$ alkyl. In certain embodiments, one of $R_1$ and $R_2$ is fluoro and the other of $R_1$ and $R_2$ is methyl, ethyl, substituted methyl or substituted ethyl. In certain embodiments, one of $R_1$ and $R_2$ is fluoro and the other of $R_1$ and $R_2$ is methyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is $C_1$-$C_6$ alkyl or substituted $C_1$-$C_6$ alkyl. In certain embodiments, at least one of $q_1$, $q_2$, $q_3$, $q_4$, $q_5$, $q_6$ and $q_7$ is methyl. In certain embodiments, at least one of $q_1$ and $q_2$ is methyl. In certain embodiments, at least one of $q_3$ and $q_4$ is methyl. In certain embodiments, at least one of $q_5$, $q_6$ and $q_7$ is methyl.

In certain embodiments, at least one of $T_3$ and $T_4$ is a linked conjugate group.

In certain embodiments, each internucleoside linking group is, independently, a phosphodiester or a phosphorothioate. In certain embodiments, each internucleoside linking group is a phosphorothioate.

In certain embodiments, Bx is uracil, thymine, cytosine, adenine or guanine. In certain embodiments, Bx is a pyrimidine, substituted pyrimidine, purine or substituted purine wherein said substitution is other than an intercalator or a linked group that does not interact with a nucleic acid target when the tetrahydropyran nucleoside analog is located in an oligomeric compound. In certain embodiments, Bx is uracil, 5-methyluracil, 5-thiazolo-uracil, 2-thio-uracil, 5-propynyl-uracil, thymine, 2'-thio-thymine, cytosine, 5-methyl-cytosine, 5-thiazolo-cytosine, 5-propynyl-cytosine, adenine, guanine, 2,6-diaminopurine, 1H-pyrimido[5,4-b][1,4]benzoxazin-2(3H)-one, 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',':4,5]-pyrrolo[2,3-d]pyrimidin-2-one. In certain embodiments, Bx is uracil, 5-methyluracil, 5-propynyl-uracil, thymine, cytosine, 5-methylcytosine, 5-propynyl-cytosine, adenine or guanine.

In certain embodiments, oligomeric compounds are provided comprising at least one tetrahydropyran nucleoside analog having the configuration shown in Formula IIa:

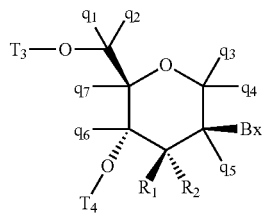

wherein

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a protecting group, a linked conjugate group or a 5' or 3'-terminal group;

each $q_1$, $q_2$, $q_3$, $q_4$, $q_5$, $q_6$ and $q_7$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

one of $R_1$ and $R_2$ is fluoro and the other of $R_1$ and $R_2$ is H, halogen, $C_1$-$C_6$ alkyl or substituted $C_1$-$C_6$ alkyl;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein the oligomeric compound comprises from about 8 to about 40 nucleosides, modified nucleosides and or tetrahydropyran nucleoside analogs.

In certain embodiments, oligomeric compounds are provided comprising at least one tetrahydropyran nucleoside analog having the configuration shown in Formula IIa wherein $R_2$ is fluoro. In certain embodiments, oligomeric compounds are provided comprising at least one tetrahydropyran nucleoside analog having the configuration shown in Formula IIa wherein $R_1$ is H and $R_2$ is fluoro. In certain embodiments, oligomeric compounds are provided comprising at least one tetrahydropyran nucleoside analog having the configuration shown in Formula IIa wherein $R_1$ is H, $R_2$ is fluoro and $q_1$, $q_2$, $q_3$, $q_4$, $q_5$, $q_6$ and $q_7$ are each H.

In certain embodiments, oligomeric compounds are provided comprising at least one contiguous region of from 1 to about 5 tetrahydropyran nucleoside analogs, each having the configuration shown in Formula IIa. In certain embodiments, oligomeric compounds are provided comprising a blockmer motif having at least one contiguous region of from 1 to about 5 tetrahydropyran nucleoside analogs, each having the configuration shown in Formula IIa. In certain embodiments, oligomeric compounds are provided comprising a 3' or 5'-hemimer motif having at least one contiguous region of from 1 to about 5 tetrahydropyran nucleoside analogs, each having the configuration shown in Formula IIa.

In certain embodiments, oligomeric compounds are provided comprising at least one contiguous region of from 1 to about 5 tetrahydropyran nucleoside analogs, each having the Formula and configuration:

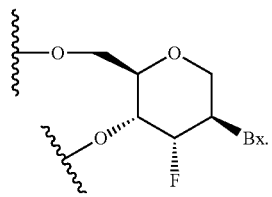

In certain embodiments, oligomeric compounds are provided comprising at least two regions of from 1 to about 5 contiguous tetrahydropyran nucleoside analogs, each having Formula II, that are separated by at least one nucleoside or modified nucleoside. In certain embodiments, oligomeric compounds are provided comprising a gapped motif having at least two regions of from 1 to about 5 contiguous tetrahydropyran nucleoside analogs, each having Formula II, wherein one region of tetrahydropyran nucleoside analogs is located at the 5'-end and the other region of tetrahydropyran nucleoside analogs is located at the 3'-end and wherein the two regions of tetrahydropyran nucleoside analogs are separated by an internal region comprising from about 6 to about 14 monomeric subunits independently selected from nucleosides, modified nucleosides and tetrahydropyran nucleoside analogs. In certain embodiments, each monomeric subunit in the internal region is a β-D-2'-deoxyribonucleoside. In certain embodiments, the internal region comprises from about 6 to about 14 β-D-2'-deoxyribonucleosides. In certain embodiments, the internal region comprises from about 10 to about 12 β-D-2'-deoxyribonucleosides. In certain embodiments, each region of tetrahydropyran nucleoside analogs independently comprises from 2 to about 3 tetrahydropyran nucleoside analogs. In certain embodiments, each region of tetrahydropyran nucleoside analogs independently comprises 2 tetrahydropyran nucleoside analogs. In certain embodiments, the internal region comprises 10 β-D-2'-deoxyribonucleosides. In certain embodiments, the internal region comprises 10 β-D-2'-deoxyribonucleosides and each tetrahydropyran nucleoside analog has the Formula and configuration:

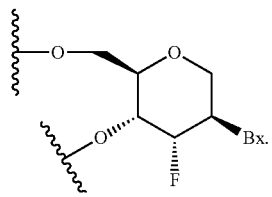

In certain embodiments, oligomeric compounds are provided comprising a gapped motif having at least two regions of from 1 to about 5 contiguous tetrahydropyran nucleoside analogs, each having Formula II, wherein one region of tetrahydropyran nucleoside analogs is located at the 5'-end and the other region of tetrahydropyran nucleoside analogs is located at the 3'-end, the two regions of tetrahydropyran nucleoside analogs are separated by an internal region comprising from about 6 to about 14 monomeric subunits independently selected from nucleosides, modified nucleosides and tetrahydropyran nucleoside analogs and the oligomeric compounds further comprise a 3'-terminal group. In certain embodiments, the 3'-terminal group comprises from 1 to about 4 modified or unmodified nucleosides.

In certain embodiments oligomeric compounds are provided wherein each oligomeric compound includes at least one tetrahydropyran nucleoside analog of Formula II comprising from about 10 to about 21 nucleosides and or nucleoside analogs in length. In certain embodiments, each oligomeric compound including at least one tetrahydropyran nucleoside analog of Formula II comprises from about 10 to about 16 nucleosides and or nucleoside analogs in length. In certain embodiments, each oligomeric compound including at least one tetrahydropyran nucleoside analog of Formula II comprises from about 10 to about 14 nucleosides and or nucleoside analogs in length.

In certain embodiments, methods for reducing target messenger RNA are provided comprising contacting one or more cells, a tissue or an animal with an oligomeric compound oligomeric compound including at least one tetrahydropyran nucleoside analog of Formula II.

In certain embodiments, methods for reducing target messenger RNA are provided comprising contacting one or more cells, a tissue or an animal with an oligomeric compound comprising at least one tetrahydropyran nucleoside analog of Formula III:

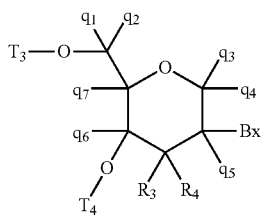

III

Wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a protecting group, a linked conjugate group or a 5' or 3'-terminal group;

each $q_1, q_2, q_3, q_4, q_5, q_6$ and $q_7$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $R_3$ and $R_4$ is, independently, H, hydroxyl, fluoro, $C_1$-$C_6$ alkoxy, $C_1$-$C_6$ alkyl or substituted $C_1$-$C_6$ alkyl;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein the oligomeric compound comprises from about 8 to about 40 nucleosides, modified nucleosides and or tetrahydropyran nucleoside analogs.

In certain embodiments, $q_1, q_2, q_3, q_4, q_5, q_6$ and $q_7$ are each H. In certain embodiments, $q_1, q_2, q_3, q_4, q_5, q_6$ and $q_7$ are each H and $R_3$ is H. In certain embodiments, $q_1, q_2, q_3, q_4, q_5, q_6$ and $q_7$ are each H, $R_3$ is H and $R_4$ is $OCH_3$. In certain embodiments, $q_1, q_2, q_3, q_4, q_5, q_6$ and $q_7$ are each H, $R_3$ is H and $R_4$ is fluoro. In certain embodiments, $q_1, q_2, q_3, q_4, q_5, q_6$ and $q_7$ are each H, $R_3$ is H and $R_4$ is hydroxyl.

In certain embodiments, each tetrahydropyran nucleoside analog in each of the oligomeric compounds used in the methods has the Formula and configuration:

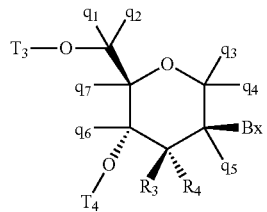

Wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a protecting group, a linked conjugate group or a 5' or 3'-terminal group;

each $q_1, q_2, q_3, q_4, q_5, q_6$ and $q_7$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $R_3$ and $R_4$ is, independently, H, hydroxyl, fluoro, $C_1$-$C_6$ alkoxy, $C_1$-$C_6$ alkyl or substituted $C_1$-$C_6$ alkyl; and each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, the oligomeric compounds used in the methods comprise a gapped motif wherein one external region of tetrahydropyran nucleoside analogs is located at the 5'-end and a second external region of tetrahydropyran nucleoside analogs is located at the 3'-end wherein the two external regions are separated by an internal region comprising from about 6 to about 14 monomeric subunits independently selected from nucleosides, modified nucleosides and tetrahydropyran nucleoside analogs.

In certain embodiments, essentially each monomeric subunit in the internal region is a β-D-2'-deoxyribonucleoside. In certain embodiments, the internal region comprises from about 6 to about 14 β-D-2'-deoxyribonucleosides. In certain embodiments, the internal region comprises from about 10 to about 12 β-D-2'-deoxyribonucleosides. In certain embodiments, each external region independently comprises from 2 to about 3 tetrahydropyran nucleoside analogs. In certain embodiments, each external region independently comprises 2 tetrahydropyran nucleoside analogs. In certain embodiments, the internal region comprises 10 β-D-2'-deoxyribonucleosides.

In certain embodiments, each tetrahydropyran nucleoside analog used in the present methods has the Formula and configuration:

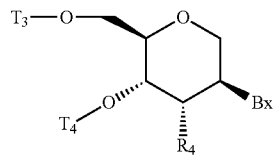

Wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a protecting group, a linked conjugate group or a 5' or 3'-terminal group; and $R_4$ is hydroxyl, fluoro or $OCH_3$.

In certain embodiments, $R_4$ is hydroxyl. In certain embodiments, $R_4$ is $OCH_3$. In certain embodiments, $R_4$ is fluoro.

DETAILED DESCRIPTION OF THE INVENTION

Provided herein are tetrahydropyran nucleoside analogs, oligomeric compounds that include such analogs and methods of using the oligomeric compounds. Also included are intermediates and methods for preparing the tetrahydropyran nucleoside analogs and the oligomeric compounds. The tetrahydropyran nucleoside analogs each have a core structure comprising a tetrahydropyran ring. Attached to one of the two carbon atoms flanking the oxygen atom is a first group capable of forming an internucleoside linkage and attached to the carbon atom next to the other flanking carbon atom (one carbon removed from the oxygen atom) is a heterocyclic base moiety. The heterocyclic base moiety can be optionally substituted with groups to enhance the affinity for a complementary base in a second strand such as a nucleic acid target. In certain embodiments, the tetrahydropyran nucleoside analogs further comprise at least one fluorine atom adjacent to the heterocyclic base on the carbon furthest from the ring oxygen atom. The carbon atom having the fluorine atom can be further substituted or not.

In certain embodiments, the tetrahydropyran nucleoside analogs have Formula XVI:

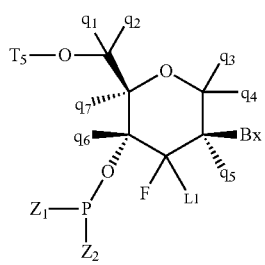

XVI wherein: Bx is a heterocyclic base moiety; $T_5$ is a hydroxyl protecting group; $L_1$ is H, halogen, $C_1$-$C_6$ alkyl or substituted $C_1$-$C_6$ alkyl; $Z_1$ is $O^-$ or $OE_1$; $Z_2$ is OH, $OE_1$ or $N(E_1)(E_2)$; each $E_1$ and $E_2$ is, independently, alkyl or substituted alkyl; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; wherein each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, the tetrahydropyran nucleoside analogs have the configuration of Formula XVII:

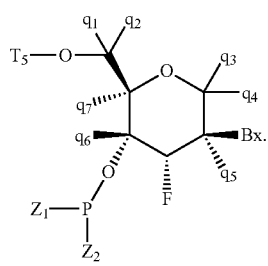

XVII

In certain embodiments, the tetrahydropyran nucleoside analog of Formula XVII is further defined wherein: $q_1$, $q_2$, $q_3$, $q_4$, $q_5$, $q_6$ and $q_7$ are each H; Bx is uracil, 5-methyluracil, thymine, cytosine, 5-methyl-cytosine, 2,6-diaminopurine, adenine or guanine; $T_5$ is 4,4'-dimethoxytrityl; $Z_1$ is $O(CH_2)_2CN$; and $Z_2$ is $N[CH_2(CH_3)_2]_2$.

In certain embodiments, the oligomeric compounds provided herein comprise at least one tetrahydropyran nucleoside analog of Formula X:

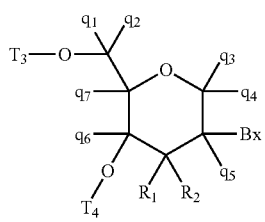

X wherein independently for each of said at least one tetrahydropyran nucleoside analog of Formula X: Bx is a heterocyclic base moiety; $T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group; $q_1$, $q_2$, $q_3$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; one of $R_1$ and $R_2$ is fluoro and the other of $R_1$ and $R_2$ is H, halogen, $C_1$-$C_6$ alkyl or substituted $C_1$-$C_6$ alkyl; each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl; and wherein said oligomeric compound comprises from about 8 to about 40 monomer subunits linked by internucleoside linking groups and at least one internucleoside linking group is a phosphorothioate internucleoside linking group.

In certain embodiments, each of the oligomeric compounds provided herein comprise at least one tetrahydropyran nucleoside analog of Formula XI:

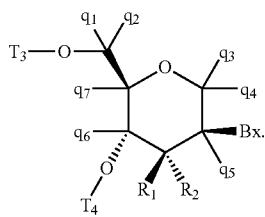

In certain embodiments, each of the tetrahydropyran nucleoside analogs in each of the oligomeric compounds provided herein has Formula XII:

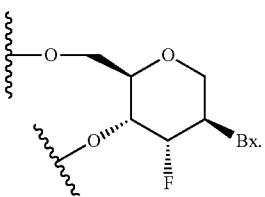

In certain embodiments, the oligomeric compound provided herein comprise at least two tetrahydropyran nucleoside analogs of Formula XIII:

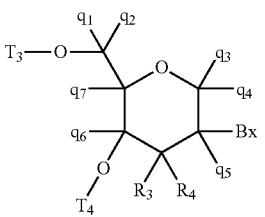

wherein independently for each of said tetrahydropyran nucleoside analogs of Formula XIII: Bx is a heterocyclic base moiety; $T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5′ or 3′-terminal group; $q_1$, $q_2$, $q_3$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; $R_3$ and $R_4$ are each independently, H, hydroxyl, halogen, $C_1$-$C_6$ alkyl, substituted $C_1$-$C_6$ alkyl, $C_1$-$C_6$ alkoxy or substituted $C_1$-$C_6$ alkoxy; each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl; wherein said oligomeric compound comprises from about 8 to about 40 monomer subunits; and at least two of the tetrahydropyran nucleoside analogs of Formula XIII are linked by a phosphorothioate internucleoside linking group.

In certain embodiments, the oligomeric compounds provided herein comprise at least two tetrahydropyran nucleoside analogs of Formula XIII wherein each tetrahydropyran nucleoside analog also has the configuration of Formula XIV:

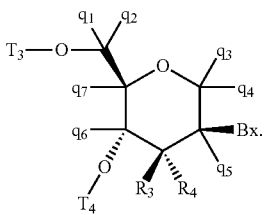

In certain embodiments, the oligomeric compounds provided herein comprise at least two tetrahydropyran nucleoside analogs of Formula XIII wherein at least one tetrahydropyran nucleoside analog has Formula XV:

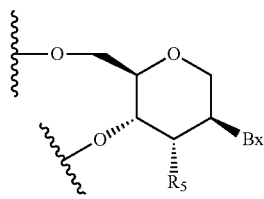

wherein: Bx is a heterocyclic base moiety; and $R_5$ is H, $OCH_3$ or F.

In certain embodiments, methods comprising contacting a cell in an animal with one or more of the oligomeric compounds disclosed herein are provided. In certain embodiments, the cell is in a human.

In certain embodiments, tetrahydropyran nucleoside analogs are provided having Formula I:

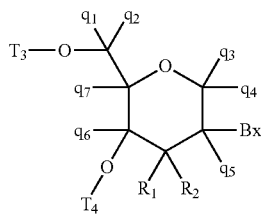

wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
each $q_1$, $q_2$, $q_3$, $q_4$, $q_5$, $q_6$ and $q_7$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
one of $R_1$ and $R_2$ is fluoro and the other of $R_1$ and $R_2$ is H, halogen, $C_1$-$C_6$ alkyl or substituted $C_1$-$C_6$ alkyl; and
wherein each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$.

In certain embodiments, tetrahydropyran nucleosides are provided having the configuration shown in Formula Ia:

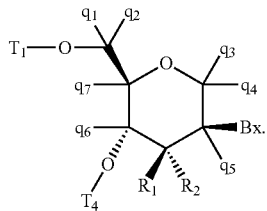

Ia

Wherein the configuration has been defined but the variables are defined the same as for Formula I above.

In certain embodiments, tetrahydropyran nucleosides are provided having Formula II:

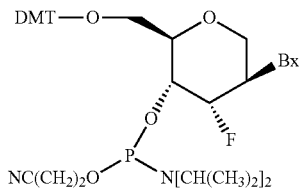

II

Wherein:
Bx is a heterocyclic base moiety.

In certain embodiments, oligomeric compounds are provided comprising at least one tetrahydropyran nucleoside analog of Formula III:

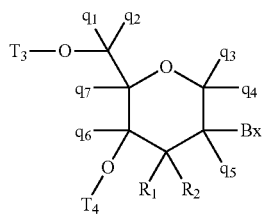

III wherein independently for each of said at least one tetrahydropyran nucleoside analog of Formula III:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
one of $R_1$ and $R_2$ is fluoro and the other of $R_1$ and $R_2$ is H, halogen, $C_1$-$C_6$ alkyl or substituted $C_1$-$C_6$ alkyl;
each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein said oligomeric compound comprises from about 8 to about 40 monomeric subunits.

In certain embodiments, oligomeric compounds are provided wherein each tetrahydropyran nucleoside analog of Formula III has the configuration shown below in Formula IIIa:

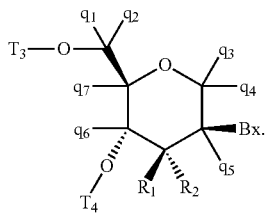

IIIa

Wherein the configuration has been defined but the variables are defined the same as for Formula III above.

In certain embodiments, oligomeric compounds are provided wherein each tetrahydropyran nucleoside analog has Formula IV:

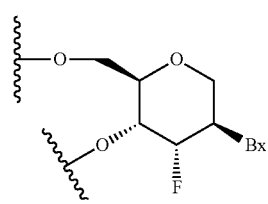

IV

Wherein:
Bx is a heterocyclic base moiety.

In certain embodiments, oligomeric compounds are provided having at least two contiguous tetrahydropyran nucleoside analogs of Formula V:

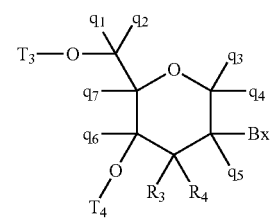

V wherein independently for each of said tetrahydropyran nucleoside analogs of Formula V:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$;

said oligomeric compound comprises from about 8 to about 40 monomeric subunits; and wherein at least two of said at least two contiguous tetrahydropyran nucleoside analogs are linked by an internucleoside linking group that is other than a phosphodiester internucleoside linking group.

In certain embodiments, oligomeric compounds are provided having at least two contiguous tetrahydropyran nucleoside analogs of Formula Va:

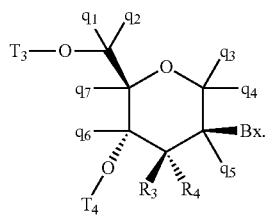

Va

Wherein the configuration has been defined but the variables are defined the same as for Formula V above and wherein each oligomeric compound comprises from about 8 to about 40 monomeric subunits; and wherein for each oligomeric compound at least two of the tetrahydropyran nucleoside analogs are linked by an internucleoside linking group that is other than a phosphodiester internucleoside linking group.

In certain embodiments, oligomeric compounds are provided having at least two contiguous tetrahydropyran nucleoside analogs of Formula Vb:

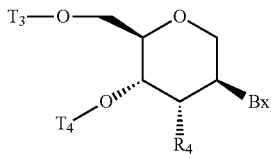

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group; and $R_4$ is H, hydroxyl, fluoro or $OCH_3$.

In certain embodiments, methods of using the oligomeric compounds are provided comprising contacting a cell in an animal with an oligomeric compound, said oligomeric compound comprising at least one tetrahydropyran nucleoside analog of Formula V:

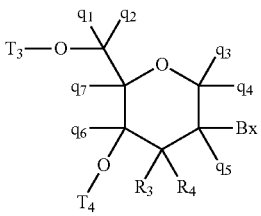

V wherein independently for each of said at least one tetrahydropyran nucleoside analog of Formula V:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein said oligomeric compound comprises from about 8 to about 40 monomeric subunits and is complementary to a target RNA.

In one aspect, methods are provided comprising contacting a cell with an oligomeric compound, said oligomeric compound comprising at least two contiguous tetrahydropyran nucleoside analogs of Formula V:

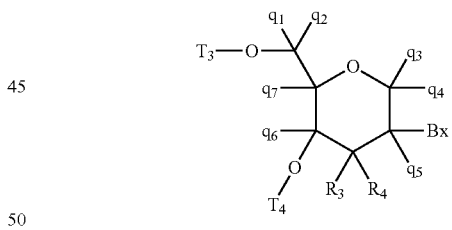

V wherein independently for each of said tetrahydropyran nucleoside analogs of Formula V:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$;

said oligomeric compound comprises from about 8 to about 40 monomeric subunits and is complementary to a target RNA; and wherein at least two of said at least two contiguous tetrahydropyran nucleoside analogs are linked by an internucleoside linking group that is other than a phosphodiester internucleoside linking group.

In certain embodiments, methods are provided comprising contacting one or more cells, a tissue or an animal with an oligomeric compound comprising at least one tetrahydropyran nucleoside analog of Formula V:

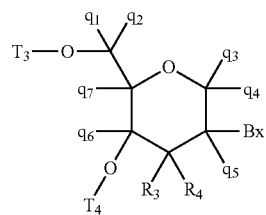

V

Wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to the oligomeric compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$R_3$ and $R_4$ are each independently, H, hydroxyl, fluoro, $C_1$-$C_6$ alkyl, substituted $C_1$-$C_6$ alkyl, $C_1$-$C_6$ alkoxy or substituted $C_1$-$C_6$ alkoxy;

each substituted group comprises one or more optionally protected substituent groups independently selected from halogen, $OJ_1$, $NJ_1J_2$, $SJ_1$, $N_3$, $OC(=X)J_1$, $OC(=X)NJ_1J_2$, $NJ_3C(=X)NJ_1J_2$ and CN, wherein each $J_1$, $J_2$ and $J_3$ is, independently, H or $C_1$-$C_6$ alkyl, and X is O, S or $NJ_1$; and wherein the oligomeric compound comprises from about 8 to about 40 nucleosides, modified nucleosides and or tetrahydropyran nucleoside analogs.

In certain embodiments, the methods are performed when the cell is in a human and the target RNA is a mRNA.

The groups capable of forming internucleoside linkages can be variable. In certain embodiments, groups capable of forming internucleoside linkages include optionally protected primary and secondary alcohols and reactive phosphorus groups. In certain embodiments, one of the groups capable of forming an internucleoside linkage is an optionally protected hydroxymethylene and the other group is an optionally protected hydroxyl or reactive phosphorus group.

Two different tetrahydropyran nucleoside analogs were incorporated into the wings of 2/10/2 gapped oligomeric compounds and compared to a 2/10/2 gapped oligomeric compound having 2'-O-MOE modified nucleosides in the wings. In each of the oligomeric compounds the 10 nucleosides in the gap are each a β-D-2'-deoxyribonucleoside, the wings are uniformly modified and each internucleoside linkage is a phosphorothioate. The gapped oligomeric compounds were evaluated for their ability to inhibit PTEN both in vitro and in vivo. The Formula and configuration of the tetrahydropyran nucleoside analogs and the 2'-O-MOE modified nucleoside is shown below:

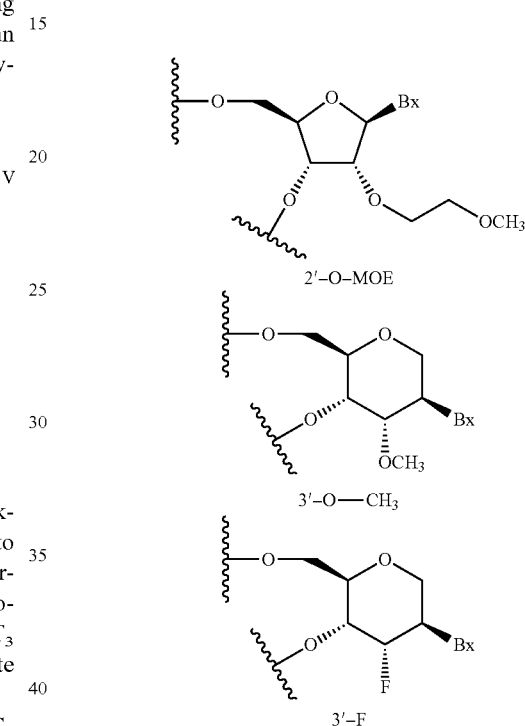

The oligomeric compounds having 3'-O—$CH_3$ and 3'-F tetrahydropyran nucleoside analogs demonstrated enhanced in vitro and in vivo activity compared to 2'-O-MOE modified nucleosides with the 3'-F demonstrating the highest level of reduction compared to the untreated control (see examples 31 and 33). The enhanced in vitro activity of oligomeric compounds incorporating either the 3'-O—$CH_3$ or the 3'-F tetrahydropyran nucleoside analogs was not predicted by the binding affinities of the modifications (Tm: 2'-O-MOE>3'-F>3'-O—$CH_3$). Oligomeric compounds having the 3'-O—$CH_3$ or 3'-F tetrahydropyran nucleoside analogs each have a lower Tm than that for the oligomeric compound having 2'-O-MOE modified nucleosides.

This level of activity is also unexpected based on previous published in vitro data. According to Published US Patent Application US 2004/0033967 the Tm of an oligomeric compound having uniform 3'-H tetrahydropyran nucleoside analogs was determined against RNA. Each 3'-O—$CH_3$ tetrahydropyran nucleoside analog incorporated into the uniform 3'-H oligomeric compound increased the Tm for RNA by only 0.4° C. per modification.

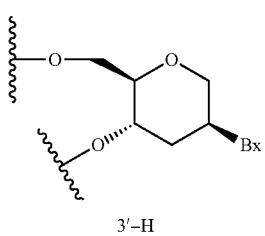

3'-H

It has been previously reported (Kang et al., *Nucleic Acids Research*, 2004, 32(14), 4411-4419) that the activity of a gapped oligomeric compound having phosphodiester linked 3'-H tetrahydropyran nucleoside analogs in the wings and phosphorothioate linked β-D-2'-deoxyribonucleosides in the gap was compared to that of a similar gapped oligomeric compound having full phosphorothioate internucleoside linkages and 2'-O-MOE modified nucleosides in the wings. It was reported that the gapmer having 3'-H tetrahydropyran nucleoside analogs showed in vitro activity that was similar to the MOE gapmer. It was further reported that the gapmer having 3'-H tetrahydropyran nucleoside analogs showed toxicity at higher concentrations (Kang, ibid). Kang et al., suggested that removing the phosphorothioate internucleoside linkages from the deoxyribonucleotide gap segment might reduce the observed cytotoxicity while maintaining the required nuclease resistance and target binding.

The in vitro data reported herein for gapped oligomeric compounds (full phosphorothioate linked gapmers) having β-D-2'-deoxyribonucleosides in the gap and either 3'-OCH$_3$ or 3'-F tetrahydropyran nucleoside analogs in the wings showed a modest increase in activity over the gapmers having 2'-O-MOE nucleosides in the wings. The 2'-O-MOE gapmer had an IC$_{50}$ of 37 compared to IC$_{50}$'s of 23 and 16 for the gapmers having 3'-O—CH and 3'-F tetrahydropyran nucleoside analogs respectively. The lower IC$_{50}$ for each of the tetrahydropyran nucleoside analogs relative to the 2'-O-MOE oligomer is unexpected because the structures and the Tm data for each of these tetrahydropyran nucleoside analogs are similar to the 3-H nucleoside analog reported in Kang.

In addition to possessing increased in vitro activity as compared to the 2'-O-MOE gapmer, the gapmers having either 3'-F or 3'-OCH$_3$ tetrahydropyran nucleoside analogs in the wings and β-D-2'-deoxyribonucleosides in the gap exhibited in vivo potency that was, for the higher dose in the study, not predicted by the Tm or the in vitro activity of the compounds. Compared to the 2'-O-MOE gapmer the 3'-β-CH$_3$ gapmer showed a two fold increase in potency and the 3'-F gapmer showed an eight fold increase in potency.

Also unexpected was the level of in vitro and in vivo activity of gapped oligomeric compounds having 3'-F tetrahydropyran nucleoside analogs compared to gapped oligomeric compounds having locked nucleosides having a 4'-CH$_2$—O-2' bridged sugars. The gapped oligomeric compounds having these motifs (examples 32 and 35) exhibit very high levels of in vitro and in vivo activity and in each study the levels between the two chemistries is essentially equal. The Tm to complementary RNA as shown herein is 60.5° C. for the gapped oligomeric compound having the locked nucleosides and 52.6 (50.7 w/out 5'-CH$_3$ groups on the monomers in the wings 2/10/2 motif) for the gapped oligomeric compound having the 3'-F tetrahydropyran modified nucleoside analogs. This is an 8-10° C. difference for the oligomeric compound with the locked nucleosides having 4'-CH$_2$—O-2' bridged sugars. The level of in vitro and in vivo activity of oligomeric compounds having 3'-F tetrahydropyran nucleoside analogs and locked nucleosides having 4'-CH$_2$—O-2' bridged sugars in the wings is unexpected based on the 8-10° C. difference in Tm.

In addition to enhanced activity the tetrahydropyran nucleoside analogs also exhibit lower toxicity when compared to a locked nucleoside as evidenced in the in vivo examples. The ALT and AST levels are extremely elevated in the high dose group for the locked nucleosides having the 4'-CH$_2$—O-2' bridge (Example 35). The ALT and ASTs for the different gapped oligomeric compounds (2/10/2 and 2/14/2 motifs) having the selected tetrahydropyran nucleoside analog do not show a significant increase.

In addition to having enhanced activity the tetrahydropyran nucleoside analogs are also expected to be useful for enhancing desired properties of oligomeric compounds in which they are incorporated such as nuclease resistance. Oligomeric compounds comprising such tetrahydropyran nucleoside analogs are also expected to be useful as primers and probes in various diagnostic applications.

In certain embodiments, tetrahydropyran nucleoside analogs are useful for modifying oligomeric compounds at one or more positions. Such modified oligomeric compounds can be described as having a particular motif. In certain embodiments, the motifs include without limitation, a gapped motif, a hemimer motif, a blockmer motif, a fully modified motif, a positionally modified motif and an alternating motif. In conjunction with these motifs a wide variety of linkages can also be used including but not limited to phosphodiester and phosphorothioate linkages used uniformly or in combinations. The positioning of tetrahydropyran nucleoside analogs and the use of linkage strategies can be easily optimized to enhance activity for a selected target. Such motifs can be further modified by the inclusion of a 5' or 3'-terminal group such as a conjugate group.

The term "motif" refers to the pattern of nucleosides in an oligomeric compound. The pattern is dictated by the positioning of nucleosides having unmodified β3-D-ribonucleosides and/or β-D-2'-deoxyribonucleosides) and/or modified sugar groups within an oligomeric compound. The type of heterocyclic base and internucleoside linkages used at each position is variable and is not a factor in determining the motif of an oligomeric compound. The presence of one or more other groups including but not limited to capping groups and conjugate groups is also not a factor in determining the motif.

Representative U.S. patents that teach the preparation of representative motifs include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" is meant to include a contiguous sequence of nucleosides comprising two different monomer subunits that alternate for essentially the entire sequence of the oligomeric compound. The pattern of alternation can be described by the formula: 5'-A(-L-B-L-A)$_n$(-L-B)$_{nn}$-3' where one of each A or each B is a tetrahydropyran nucleoside analog and the other of each A or B is a monomer subunit that is other than a tetrahydropyran nucleoside, each L is an internucleoside linking group, nn is 0 or 1 and n is from about 4 to about 12. This permits alternating oligomeric compounds from about 9 to about 26 monomer subunits in length. This length range is not meant to be limiting as longer and shorter oligomeric compounds are also amenable to the present invention. This formula also allows for even and odd lengths for alternating oligomeric compounds.

In certain embodiments, the other of each A or B is selected from β-D-ribonucleosides, 2'-modified nucleosides, 4'-thio modified nucleosides, 4'-thio-2'-modified nucleosides, bicyclic sugar modified nucleosides and other modified nucleosides. The alternating motif is not defined by the nucleobase sequence or the internucleoside linkages.

As used herein the term "fully modified motif" is meant to include a contiguous sequence of monomer subunits that have the same sugar or sugar surrogate group. In certain embodiments, the fully modified motif includes a contiguous sequence of tetrahydropyran nucleoside analogs. In certain embodiments, the 3' and 5'-terminal ends comprise unmodified nucleosides.

As used herein the term "hemimer motif" is meant to include an oligomeric compound having contiguous sequence of monomer subunits of one type with a contiguous sequence of monomer subunits of a second type located at one of the termini. The two types of monomer subunits are differentiated by the type of sugar or sugar surrogate group comprising the nucleosides and is independent of the type of base and linkage used. Sugar surrogate groups includes other than ribose type sugars such as the presently described tetrahydropyran nucleoside analogs wherein a tetrahydropyran ring is used in place of the ribose ring. In certain embodiments, the sugar surrogate group is a tetrahydropyran moiety comprising a tetrahydropyran nucleoside analog. In certain embodiments, the hemimer motif comprises a contiguous sequence of from about 10 to about 28 monomer subunits of one type with from 1 to 5 or from 2 to 5 monomer subunits of a second type located at one of the termini. In certain embodiments the hemimer is a contiguous sequence of from about 8 to about 20 β-D-2'-deoxyribonucleosides having from 1-12 contiguous tetrahydropyran nucleoside analogs located at one of the termini. In certain embodiments, In certain embodiments the hemimer is a contiguous sequence of from about 8 to about 20 β-D-2'-deoxyribonucleosides having from 1-5 contiguous tetrahydropyran nucleoside analogs located at one of the termini. In certain embodiments the hemimer is a contiguous sequence of from about 12 to about 18 β-D-2'-deoxyribonucleosides having from 1-3 contiguous tetrahydropyran nucleoside analogs located at one of the termini.

As used herein the term "blockmer motif" is meant to include an oligomeric compound having a contiguous sequence of monomer subunits of one type with a contiguous sequence of monomer subunits of a second type located at internally. The two types of monomer subunits are differentiated by the type of sugar or sugar surrogate group comprising the nucleosides and is independent of the type of base and linkage used. A blockmer overlaps somewhat with a gapmer in the definition but typically only the monomer subunits in the block are modified in a blockmer and only the monomer subunits in the external regions are modified in a gapmer. In certain embodiments, blockmers can have other types of modified monomer subunits throughout the oligomeric compound at positions not occupied by the block.

As used herein the term "positionally modified motif" is meant to include a sequence of monomer subunits of one type that is interrupted with two or more regions of from 1 to about 5 modified monomer subunits monomer subunits of one type. In certain embodiments, a positionally modified oligomeric compound is a sequence of from 8 to 20 β-D-2'-deoxyribonucleosides that further includes two or three regions of from 2 to about 5 contiguous tetrahydropyran nucleoside each. Positionally modified oligomeric compounds are distinguished from gapped motifs, hemimer motifs, blockmer motifs and alternating motifs because the pattern of regional substitution defined by any positional motif is not defined by these other motifs. Positionally modified motifs are not determined by the nucleobase sequence or the location or types of internucleoside linkages. The term positionally modified oligomeric compound includes many different specific substitution patterns.

As used herein the term "gapmer" or "gapped oligomeric compound" is meant to include a contiguous sequence of nucleosides that is divided into 3 regions, an internal region having an external region on each of the 5' and 3' ends. The regions are differentiated from each other at least by having different sugar or sugar surrogate groups that comprise the nucleosides. In certain embodiments, the external regions are each, independently, from 1 to about 5 modified nucleosides and the internal region is from 6 to 18 nucleosides. The types of nucleosides that are generally used to differentiate the regions of a gapped oligomeric compound include, but are not limited to, β-D-ribonucleosides, β-D-2'-deoxyribonucleosides, 2'-modified nucleosides, 4'-thio modified nucleosides, 4'-thio-2'-modified nucleosides, bicyclic sugar modified nucleosides and sugar surrogate containing nucleosides such as tetrahydropyran nucleoside analogs. Each of the regions of a gapped oligomeric compound is essentially uniformly modified e.g. the sugar or sugar surrogate groups are identical with at least the internal region having different sugar groups than each of the external regions. The internal region or the gap generally comprises β-D-2'-deoxyribonucleosides but can be a sequence of sugar modified nucleosides.

In certain embodiments, the gapped oligomeric compounds comprise an internal region of β-D-2'-deoxyribonucleosides with one of the external regions comprising tetrahydropyran nucleoside analogs as disclosed herein. In certain embodiments, the gapped oligomeric compounds comprise an internal region of β-D-2'-deoxyribonucleosides with both of the external regions comprising tetrahydropyran nucleoside analogs as disclosed herein. In certain embodiments, the gapped oligomeric compounds comprise an internal region of β-D-2'-deoxyribonucleosides with both of the external regions comprising tetrahydropyran nucleoside analogs having Formula II. A further example of a gapped motif is shown in Example 32 and 35 where an oligomeric compound comprising 14 nucleosides has 2 bicyclic nucleosides positioned at each of the 3' and 5' ends and further includes 10 unmodified β-D-2'-deoxyribonucleosides in the internal region. This oligomeric compound has a gapped motif wherein the terminal externa regions of bicyclic nucleosides are considered the wings and the β-D-2'-deoxyribonucleoside internal region is considered the gap.

In certain embodiments, gapped oligomeric compounds are provided comprising one or two tetrahydropyran nucleoside analogs at the 5'-end, two or three tetrahydropyran nucleoside analogs at the 3'-end and an internal region of from 10 to 16 nucleosides. In certain embodiments, gapped oligomeric compounds are provided comprising one tetrahydropyran nucleoside analog at the 5'-end, two tetrahydropyran nucleoside analogs at the 3'-end and an internal region of from 10 to 16 nucleosides. In certain embodiments, gapped oligomeric compounds are provided comprising one tetrahydropyran nucleoside analog at the 5'-end, two tetrahydropyran nucleoside analogs at the 3'-end and an internal region of from 10 to 14 nucleosides. In certain embodiments, the internal region is essentially a contiguous sequence of β-D-2'-deoxyribonucleosides. In another embodiment, oligomeric compounds are provided that further include, but are not limited to, one or more 5' or 3'-terminal groups such as further modified or unmodified nucleosides, linked conjugate groups and other groups known to the art skilled.

In certain embodiments, gapped oligomeric compounds are provided that are from about 10 to about 21 nucleosides in length. In another embodiment, gapped oligomeric compounds are provided that are from about 12 to about 16 nucleosides in length. In a further embodiment, gapped oligomeric compounds are provided that are from about 12 to about 14 nucleosides in length.

In one aspect, oligomeric compounds are provided comprising tetrahydropyran nucleoside analogs having formula III. In another aspect, oligomeric compounds are provided comprising tetrahydropyran nucleoside analogs having formula IIIa. In another aspect, oligomeric compounds are provided comprising tetrahydropyran nucleoside analogs having formula IV. In another aspect, oligomeric compounds are provided comprising tetrahydropyran nucleoside analogs having formula V. In another aspect, oligomeric compounds are provided comprising tetrahydropyran nucleoside analogs having formula Va. In another aspect, oligomeric compounds are provided comprising tetrahydropyran nucleoside analogs having formula Vb.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic, heteroaryl, heteroarylalkyl, amino (—N$R_{bb}R_{cc}$), imino(=N$R_{bb}$), amido (—C(O)N—$R_{bb}R_{cc}$ or —N($R_{bb}$)C(O)$R_{aa}$), azido (—$N_3$), nitro (—$NO_2$), cyano (—CN), carbamido (—OC(O)N$R_{bb}R_{cc}$ or —N($R_{bb}$)C(O)O$R_{aa}$), ureido (—N($R_{bb}$)C(O)N$R_{bb}R_{cc}$), thioureido (—N($R_{bb}$)C(S)N$R_{bb}R_{cc}$), guanidinyl (—N($R_{bb}$)C(=N$R_{bb}$)N$R_{bb}R_{cc}$), amidinyl (—C(=N$R_{bb}$)N$R_{bb}R_{cc}$ or —N($R_{bb}$)C(N$R_{bb}$)$R_{aa}$), thiol (—S$R_{bb}$), sulfinyl (—S(O)$R_{bb}$), sulfonyl (—S(O)$_2R_{bb}$), sulfonamidyl (—S(O)$_2$N$R_{bb}R_{cc}$ or —N($R_{bb}$)S(O)$_2R_{bb}$) and conjugate groups. Wherein each $R_{aa}$, $R_{bb}$ and $R_{cc}$ is, independently, H, an optionally linked chemical functional group or a further substituent group with a preferred list including, without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substitutent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substitutent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substitutent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substitutent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substitutent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substitutent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substitutent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substitutent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substitutent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substitutent groups.

The term "heteroarylalkyl," as used herein, refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substitutent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substitutent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

The term "oxo" refers to the group (=O).

The terms "bicyclic nucleic acid (BNA)" and "bicyclic nucleoside" refer to a nucleoside wherein the furanose portion of the nucleoside includes a bridge connecting two carbon atoms on the furanose ring, thereby forming a bicyclic ring system.

The term "bicyclic nucleoside analog" refers to BNA like nucleosides wherein the ribose sugar has been replaced or modified. As used in the present application, the tetrahydropyran nucleoside analog analogs refer to tetrahydropyran nucleoside analogs wherein the ribose portion of the nucleoside is replaced with a tetrahydropyran ring.

The terms "stable compound" and "stable structure" are meant to indicate a compound that is sufficiently robust to survive isolation to a useful degree of purity from a reaction mixture, and Formulation into an efficacious therapeutic agent. Only stable compounds are contemplated herein.

Linking groups or bifunctional linking moieties such as those known in the art are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In some embodiments, the linker comprises a chain structure or an oligomer of repeating units such as ethylene glycols or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, oligomeric compounds are modified by covalent attachment of one or more 5' or 3'-terminal groups. The term "terminal group" as used herein is meant to include useful groups known to the art skilled that can be placed on one or both of the 3' and 5'-ends of an oligomeric compound for various purposes such as enabling the tracking of the oligomeric compound (a fluorescent label or other reporter group), improving the pharmacokinetics or pharmacodynamics of the oligomeric compound (a group for enhancing uptake and delivery) or enhancing one or more other desirable properties of the oligomeric compound (group for improving nuclease stability or binding affinity). In certain embodiments, 3' and 5'-terminal groups include without limitation, one or more modified or unmodified nucleosides, conjugate groups, capping groups, phosphate moieties and protecting groups.

In certain embodiments, oligomeric compounds are modified by covalent attachment of one or more conjugate groups. In general, conjugate groups modify one or more properties of the attached oligomeric compound including but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, oligomeric compounds are modified by covalent attachment of one or more 5' or 3'-terminal groups that include but are not limited to further modified or unmodified nucleosides. Such terminal groups can be useful for enhancing properties of oligomeric compounds such as for example nuclease stability, uptake and delivery.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE),2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoro-acetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include, but are not limited to, carbamate-protecting groups, such as 2-trimethylsilylethoxycarbonyl (Teoc), 1-methyl-1-(4-biphenyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In certain embodiments, oligomeric compounds are prepared by connecting nucleosides with optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12, pp. 2223-2311 (1992).

The term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.*, 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

In certain embodiments, compounds having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^{V}$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the $P^{V}$ state using known methods to yield, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

As used herein the term "internucleoside linkage" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyleneimino, and neutral non-ionic internucleoside linking groups such as amide-3 (3'-$CH_2$—N(H)—C(=O)—N(H)-5'), amide-4 (3'-$CH_2$—N(H)—C(=O)-5').

Specific examples of oligomeric compounds useful in this invention include oligonucleotides containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Modified internucleoside linkages not having a phosphorus atom include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In the context of this invention, the term "oligonucleoside" refers to a sequence of two or more nucleosides that are joined by internucleoside linkages that do not have phosphorus atoms.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

As used herein the phrase "neutral internucleoside linkage" is intended to include internucleoside linkages that are non-ionic. Neutral internucleoside linkages include but are not limited to phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linkages include nonionic linkages comprising mixed N, O, S and $CH_2$ component parts.

The compounds described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., Advanced Organic Chemistry, 3rd Edition, John Wiley & Sons, New York (1985); *Comprehensive Organic Synthesis. Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein the term "oligomeric compound" is meant to include a polymer having at least a region that is capable of hybridizing to a nucleic acid molecule. The term "oligomeric compound" includes oligonucleotides, oligonucleotide analogs and oligonucleosides as well as nucleotide mimetics and/or mixed polymers comprising nucleic acid and non-nucleic acid components and chimeric oligomeric compounds comprising mixtures of nucleosides from any of these categories. The tetryhydropyran nucleoside analogs can be classified as a mimetic as the ribose sugar portion has been replaced with a tetrahydropyran group. Oligomeric compounds are routinely prepared linearly but can be joined or otherwise prepared to be circular and may also include branching. Oligomeric compounds can form double stranded constructs such as for example two strands hybridized to form double stranded compositions. The double stranded compositions can be linked or separate and can include overhangs on the ends. In general, an oligomeric compound comprises a backbone of linked monomeric subunits where each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified. The linkage-sugar unit, which may or may not include a heterocyclic base, may be substituted with a mimetic such as the monomers in peptide nucleic acids. The ability to modify or substitute portions or entire monomers at each position of an oligomeric compound gives rise to a large number of possible motifs.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

The term "nucleobase" or "heterocyclic base moiety" as used herein, is intended to by synonymous with "nucleic acid base or mimetic thereof" In general, a nucleobase or heterocyclic base moiety is any substructure that contains one or more atoms or groups of atoms capable of hydrogen bonding to a base of a nucleic acid.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H- pyrimido[4,5-b]indol-2-one), pyridoindole cytidine (H-pyrido[3',':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

In certain embodiments, oligomeric compounds may also contain one or more nucleosides having modified sugar moieties. The furanosyl sugar ring can be modified in a number of ways including substitution with a substituent group (2', 3', 4' or 5'), bridging to form a BNA and substitution of the 4'-O with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-O(CH$_2$)$_2$—OCH$_3$ (2'-MOE or simply MOE) substituent group; 4'-thio modified sugars, 4'-thio-2'-substituted sugars and bicyclic modified sugars.

As used herein the term "nucleoside mimetic" is intended to include those structures used to replace the sugar or the sugar and the base not the linkage at one or more positions of an oligomeric compound such as for example nucleoside mimetics having morpholino or bicyclo[3.1.0]hexyl sugar mimetics e.g. non furanose sugar units with a phosphodiester linkage. The term "sugar surrogate" overlaps with the slightly broader term "nucleoside mimetic" but is intended to indicate replacement of the sugar unit (furanose ring) only. The term "nucleotide mimetic" is intended to include those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

As used herein the term "modified nucleoside" is meant to include all manner of modified nucleosides that can be incorporated into an oligomeric compound using oligomer synthesis. The term includes nucleosides having a ribofuranose sugar and can include a heterocyclic base but abasic modified nucleoside are also envisioned. One group of representative modified nucleosides includes without limitation bicyclic nucleosides, 2'-modified nucleosides, 4'-thio modified nucleosides and 4'-thio-2'-modified nucleosides and base modified nucleosides.

As used herein the term "monomer subunit" is meant to include all manner of monomers that can be incorporated into an oligomeric compound using oligomer synthesis. The term includes nucleosides having a ribofuranose sugar and a heterocyclic base but also includes monomers having modified sugars or surrogate sugars e.g. mimetics. As such the term includes nucleosides, modified nucleosides (such as bicyclic nucleosides), nucleoside mimetics (such as the tetrahydropyran nucleoside analogs provided herein).

Those skilled in the art, having possession of the present disclosure will be able to prepare oligomeric compounds of essentially any viable length to practice the methods disclosed herein. Such oligomeric compounds will include at least one and preferably a plurality of tetrahydropyranyl nucleoside analogs provided herein and may also include other monomer subunits including but not limited to nucleosides, modified nucleosides and nucleoside mimetics.

In certain embodiments, oligomeric compounds comprise from about 8 to about 80 monomer subunits in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin In another embodiment, the oligomeric compounds of the invention are 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In another embodiment, the oligomeric compounds of the invention are 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In another embodiment, the oligomeric compounds of the invention are 10 to 16 monomer subunits in length. One having ordinary skill in the art will appreciate that this embodies oligomeric compounds of 10, 11, 12, 13, 14, 15 or 16 monomer subunits in length, or any range therewithin In another embodiment, the oligomeric compounds of the invention are 12 to 16 monomer subunits in length. One having ordinary skill in the art will appreciate that this embodies oligomeric compounds of 12, 13, 14, 15 or 16 monomer subunits in length, or any range therewithin.

In another embodiment, the oligomeric compounds of the invention are 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds of any of a variety of ranges of lengths of linked monomer subunits are provided. In certain embodiments, oligomeric compounds are provided consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, ranges for the length of the oligomeric compounds are 8-16, 8-40, 10-12, 10-14, 10-16, 10-18, 10-20, 10-21, 12-14, 12-16, 12-18, 12-20 and 12-24 linked monomer subunits.

In certain embodiments, the ranges for the oligomeric compounds listed herein are meant to limit the number of monomer subunits in the oligomeric compounds, however such oligomeric compounds may further include protecting groups such as hydroxyl protecting groups, optionally linked conjugate groups, 5' and/or 3'-terminal groups and/or other substituents.

Chimeric oligomeric compounds have differentially modified nucleosides at two or more positions and are generally defined as having a motif. Chimeric oligomeric compounds of the invention may be formed as composite structures of two or more oligonucleotides, oligonucleotide analogs, oligonucleosides and/or oligonucleotide mimetics as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

In certain embodiments, oligomerization of modified and unmodified nucleosides and mimetics thereof, is performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—$CH_2$—O—$Si(iPr)_3$ (TOM), and the 5'-O-silyl ether-2'-ACE (5'-O-bis(trimethylsiloxy)cyclododecyloxysilyl ether (DOD)-2'-β-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries.

The primary groups being used for commercial RNA synthesis are:
TBDMS=5'-O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1(2-fluorophenyl)-4-methoxypiperidin-4-yl].

In certain embodiments, each of the aforementioned RNA synthesis strategies can be used herein. Strategies that would be a hybrid of the above e.g. using a 5'-protecting group from one strategy with a 2'-O-protecting from another strategy are also amenable herein.

In the context of this invention, "hybridization" means the pairing of complementary strands of oligomeric compounds. In certain embodiments, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent.

Suitable target segments may also be combined with their respective complementary antisense oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds provided herein can also be applied in the areas of drug discovery and target validation. In certain embodiments, provided here is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype. In certain embodiments, there is provided oligomeric compounds of the invention for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds of the invention may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or therapeutics, can be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

While in certain embodiments, oligomeric compounds provided herein can be utilized as described, the following examples serve only to illustrate and are not intended to be limiting.

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligonucleotides: Unsubstituted and substituted phosphodiester (P=O) oligonucleotides can be synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation is effected in certain embodiments by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligonucleotides are recovered by precipitating with greater than 3 volumes of ethanol from a 1 M $NH_4OAc$ solution. Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. No. 5,610,289 or 5,625,050.

Phosphoramidite oligonucleotides can be prepared as described in U.S. Pat. No. 5,256,775 or U.S. Pat. No. 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Example 3

Oligonucleotide Isolation

After cleavage from the controlled pore glass solid support or other support medium and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligonucleotides are purified by HPLC, as described by Chiang et al., *J. Biol. Chem.* 1991, 266, 18162-18171. Results obtained with HPLC-purified material are generally similar to those obtained with non-HPLC purified material.

Example 4

Oligonucleotide Synthesis

96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Oligonucleotide Analysis Using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

Cell Culture and Oligonucleotide Treatment

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing) Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents were obtained from Invitrogen Life Technologies (Carlsbad, Calif.). RT, real-time PCR was carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM° Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM° Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Example 8

Preparation of Compound 8

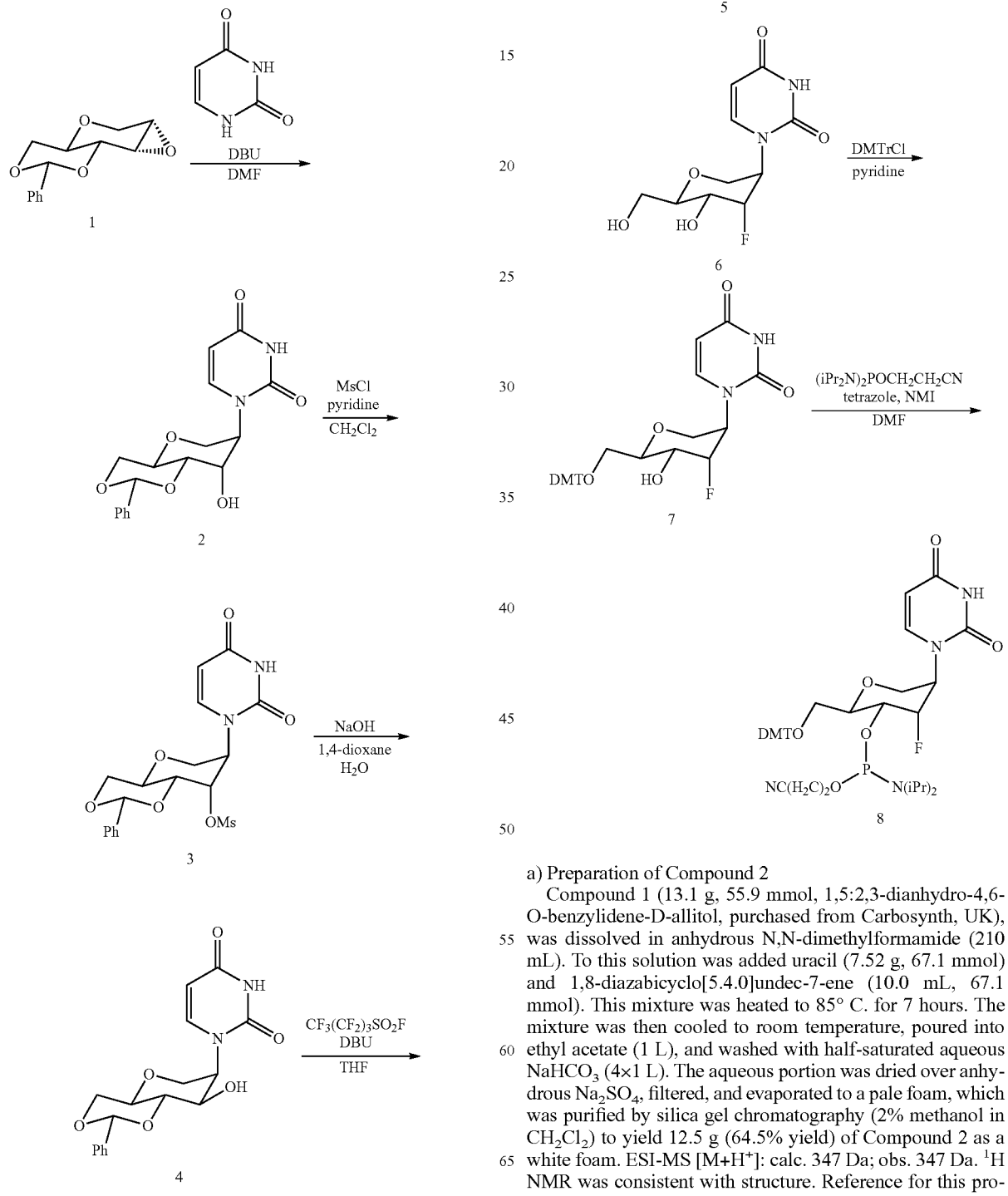

a) Preparation of Compound 2

Compound 1 (13.1 g, 55.9 mmol, 1,5:2,3-dianhydro-4,6-O-benzylidene-D-allitol, purchased from Carbosynth, UK), was dissolved in anhydrous N,N-dimethylformamide (210 mL). To this solution was added uracil (7.52 g, 67.1 mmol) and 1,8-diazabicyclo[5.4.0]undec-7-ene (10.0 mL, 67.1 mmol). This mixture was heated to 85° C. for 7 hours. The mixture was then cooled to room temperature, poured into ethyl acetate (1 L), and washed with half-saturated aqueous NaHCO$_3$ (4×1 L). The aqueous portion was dried over anhydrous Na$_2$SO$_4$, filtered, and evaporated to a pale foam, which was purified by silica gel chromatography (2% methanol in CH$_2$Cl$_2$) to yield 12.5 g (64.5% yield) of Compound 2 as a white foam. ESI-MS [M+H$^+$]: calc. 347 Da; obs. 347 Da. $^1$H NMR was consistent with structure. Reference for this procedure—Abramov, M.; Marchand, A.; Calleja-Marchand, A.;

Herdewijn, P. Synthesis of D-Altritol Nucleosides with a 3'-O-tert-butyldimethylsilyl protecting group. *Nucleosides, Nucleotides & Nucleic Acids* (2004) 23, 439.

b) Preparation of Compound 3

Compound 2 (12.1 g, 35.0 mmol) was dissolved in a mixture of anhydrous $CH_2Cl_2$ (50 mL) and anhydrous pyridine (50 mL). This mixture was cooled to 0° C., then treated with methanesulfonyl chloride (6.77 mL, 87.4 mmol). After maintaining at 0° C. for 15 minutes, the mixture was warmed to room temperature and stirred an additional 5 hours. Concentration in vacuo yielded a golden slush, which was resuspended in $CH_2Cl_2$ (500 mL), washed with half-saturated aq. $NaHCO_3$, dried over anhydrous $Na_2SO_4$, filtered, and evaporated to a golden oil. Subsequent purification by silica gel chromatography (2% methanol in $CH_2CU$ yielded 11.7 g (78.6% yield) of Compound 3 as a pale yellow foam. ESI-MS [M+H$^+$]: calc. 425 Da; obs. 425 Da. $^1$H NMR was consistent with structure.

c) Preparation of Compound 4

Compound 3 (11.2 g, 26.5 mmol) was suspended in 1,4-dioxane (100 mL). To this suspension was added 100 mL of 2M aqueous NaOH. The resulting mixture was warmed to 60° C. and stirred for 3.5 hours. The mixture was cooled to room temperature, then neutralized with acetic acid (11.4 mL). The mixture was concentrated in vacuo to ~100 mL and then poured into $CH_2Cl_2$ (500 mL). The resulting mixture was washed with saturated aq. $NaHCO_3$ (500 mL), dried over anhydrous $Na_2SO_4$, filtered, and evaporated to yield 8.23 g (89.7% yield) of Compound 4 as an off-white solid. ESI-MS [M+H$^+$]: calc. 347 Da; obs. 347 Da. $^1$H NMR was consistent with structure.

d) Preparation of Compound 5

Compound 4 (7.96 g, 23.0 mmol) was dissolved in anhydrous THF (100 mL). To this solution was added 1,8-diazabicyclo[5.4.0]undec-7-ene (5.1 mL, 34 mmol), followed by nonafluorobutanesulfonyl fluoride (11.6 mL, 34 mmol), which was added dropwise with stirring. This mixture was incubated at 30° C. for 84 hours. The mixture was poured into ethyl acetate (400 mL), washed with half-saturated aq. $NaHCO_3$ (2×500 mL), dried over anhydrous $Na_2SO_4$, filtered, and evaporated to a pale foam. Silica gel chromatography (1:1 hexanes:ethyl acetate) yielded 7.92 g of Compound 5 as an impure mixture. This mixture was used for subsequent reactions without further purification. A small portion was more carefully purified by silica gel chromatography for analytical characterization. ESI-MS [M+H$^+$]: calc. 349 Da; obs. 349 Da (major impurity [M+H$^+$]=329, consistent with elimination of HF). Both $^1$H and $^{19}$F NMR were consistent with structure for Compound 5.

e) Preparation of Compound 6

Impure Compound 5 (6.87 g, 19.7 mmol) was dissolved in anhydrous $CH_2Cl_2$ (100 mL). To this solution was added trifluoroacetic acid (35 mL). After stirring at room temperature for 1 hour, this mixture was concentrated in vacuo to a pale-orange oil. Purification by silica gel chromatography (stepwise gradient from 1% methanol to 10% methanol in $CH_2Cl_2$) yielded 3.58 g (69% yield) of Compound 6 as a white foam. ESI-MS [M+H$^+$]: calc. 261 Da; obs. 261 Da.

f) Preparation of Compound 7

Compound 6 (3.37 g, 12.9 mmol) was dissolved in anhydrous pyridine (40 mL). After cooling to 0° C., the solution was treated with 4,4'-dimethoxytrityl chloride (6.59 g, 19.5 mmol). After stirring at 0° C. for 20 minutes, the mixture was warmed to room temperature for an additional 3 hours. The resulting mixture was concentrated in vacuo to a brown oil, resuspended in $CH_2Cl_2$ (400 mL), washed with half-saturated aq. $NaHCO_3$ (2×400 mL), dried over anhydrous $Na_2SO_4$, filtered, and evaporated. Silica gel chromatography (2% v/v methanol in $CH_2Cl_2$, yielded 5.68 g (77.9% yield) of Compound 7 as a beige foam. Both $^1$H and $^{19}$F NMR were consistent with structure.

g) Preparation of Compound 8

Compound 7 (2.50 g, 4.45 mmol) was dissolved in anhydrous N,N-dimethylformamide (11.2 mL). To this solution was added 2-cyanoethyl-N,N,N',N'-tetraisopropylphosphorodiamidite (1.98 mL, 6.23 mmol), tetrazole (156 mg, 2.22 mmol), and N-methylimidazole (89 µL, 1.11 mmol). After stirring at room temperature for 3 hours, the mixture was treated with triethylamine (2.48 mL, 17.8 mmol), stirred for 5 minutes, then poured into ethyl acetate (250 mL). The resulting solution was washed with 1:1 saturated aq. $NaHCO_3$: saturated aq. NaCl (1×200 mL), followed by saturated aq. NaCl (1×200 mL). The organic portion was dried over anhydrous $Na_2SO_4$, filtered, and evaporated. Silica gel chromatography (1:1 hexanes:ethyl acetate) yielded 2.61 g (76.8% yield) of Compound 8 as a pale yellow foam. $^1$H, $^{19}$F, and $^{31}$P NMR were consistent with the structure of Compound 8 as a mixture of phosphorous diastereomers.

Example 9

Preparation of Compound 13

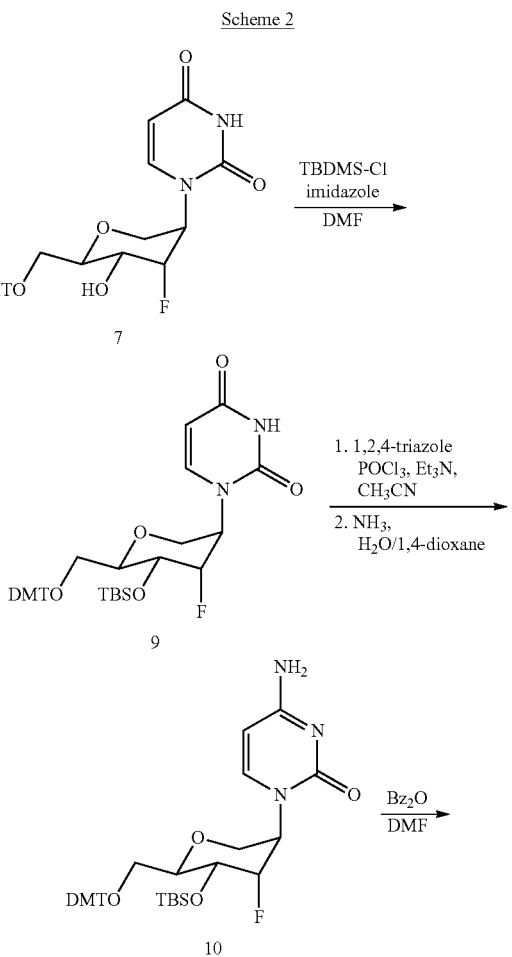

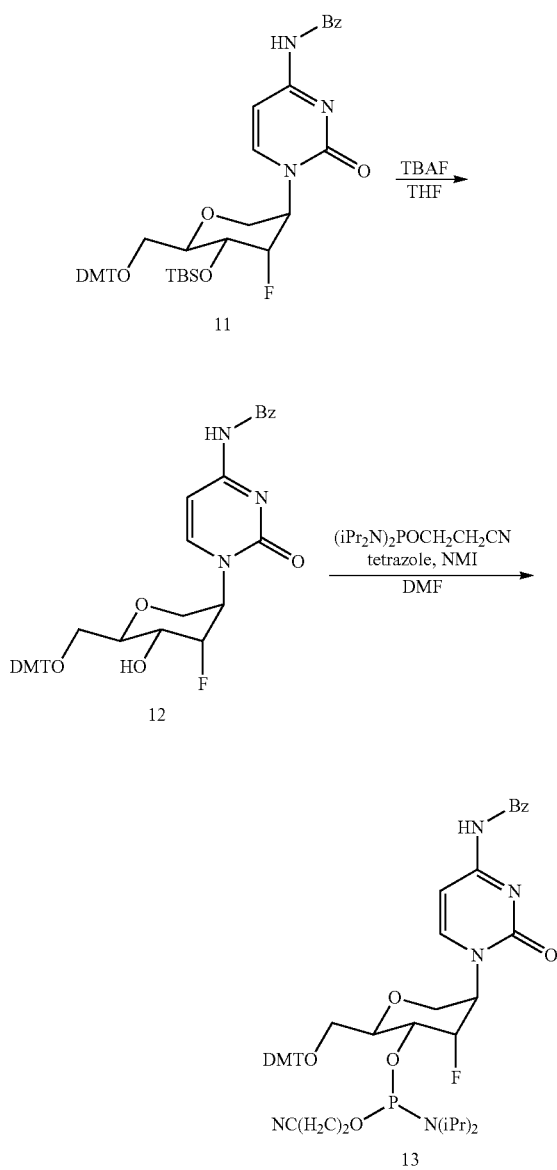

a) Preparation of Compound 9

Compound 7 (2.50 g, 4.44 mmol, prepared in the previous example) was dissolved in anhydrous N,N-dimethylformamide (10 mL). To this solution was added imidazole (1.82 g, 26.7 mmol) and tert-butyldimethylsilyl chloride (1.34 g, 8.88 mmol). After stirring at room temperature for 12 hours, the mixture was poured into ethyl acetate (250 mL), washed with half-saturated aq. NaHCO$_3$ (2×200 mL) and saturated aq. NaCl (2×200 mL), dried over anhydrous Na$_2$SO$_4$, filtered, and evaporated. Silica gel chromatography (1:1 hexanes:ethyl acetate) yielded 2.52 g (83.8% yield) of Compound 9 as a white foam. $^1$H and $^{19}$F NMR were consistent with the indicated structure.

b) Preparation of Compound 10

To a chilled (0° C.) suspension of 1,2,4-triazole (3.40 g, 49.2 mmol) in anhydrous acetonitrile (44 mL) was added phosphorous oxychloride (1.31 mL, 14.1 mmol). After stirring at 0° C. for 20 minutes, triethylamine (9.8 mL, 70 mmol) was added to the mixture. To the resulting slurry was added a solution of Compound 9 (2.38 g, 3.52 mmol) in anhydrous acetonitrile (20 mL). The mixture was held at 0° C. for 1 hour, then warmed to room temperature for 2 hours. The mixture was subsequently concentrated to approximately half its original volume, poured into ethyl acetate (250 mL), washed with half-saturated aq. NaCl (2×200 mL), dried over anhydrous Na$_2$SO$_4$, filtered, and evaporated to a yellow foam. This residue was redissolved in 1,4-dioxane (20 mL) and treated with conc. aq. NH$_4$OH (20 mL). The reaction vessel was sealed and stirred at room temperature for 12 hours, at which time the mixture was concentrated under reduced pressure, poured into CH$_2$Cl$_2$ (200 mL), washed with half-saturated aq. NaHCO$_3$ (1×200 mL), dried over anhydrous Na$_2$SO$_4$, filtered, and evaporated. Silica gel chromatography (1.5% v/v methanol in CH$_2$Cl$_2$) yielded 1.98 g (83.4%) of Compound 10 as a yellow foam. ESI-MS [M−H$^+$]: calc. 674.8 Da; obs. 674.3 Da. $^1$H and $^{19}$F NMR were consistent with structure.

c) Preparation of Compound 11

Compound 10 (1.86 g, 2.76 mmol) was dissolved in anhydrous N,N-dimethylformamide (10 mL). To the resulting solution was added benzoic anhydride (938 mg, 4.14 mmol). After stirring at room temperature for 14 hours, the mixture was poured into ethyl acetate (250 mL), washed with saturated aq. NaHCO$_3$ (1×200 mL) and half-saturated aq. NaCl (2×200 mL), dried over anhydrous Na$_2$SO$_4$, filtered and evaporated. Silica gel chromatography (1:1 hexanes:ethyl acetate) yielded 2.12 g (98.4%) of Compound 11 as a white foam. ESI-MS [M−H$^+$]: calc. 778 Da; obs. 778 Da. $^1$H and $^{19}$F NMR were consistent with structure.

d) Preparation of Compound 12

Compound 11 (1.98 g, 2.54 mmol) was dissolved in anhydrous THF (3 mL). To this solution was added 3.3 mL of 1 M tetrabutylammonium fluoride in THF. After 13 hours, the mixture was evaporated, redissolved in CH$_2$Cl$_2$, and subjected to silica gel chromatography. Elution with 1.5% (v/v) methanol in CH$_2$Cl$_2$ yielded 1.58 g (93.9%) of Compound 12 as an off-white foam. ESI-MS [M−H$^+$]: calc. 664.7 Da; obs. 664.2 Da. $^1$H and $^{19}$F NMR were consistent with structure.

e) Preparation of Compound 13

Compound 12 (1.52 g, 2.28 mmol) was dissolved in anhydrous N,N-dimethylformamide (5.8 mL).

To this solution was added 2-cyanoethyl-N,N,N',N'-tetraisopropylphosphorodiamidite (1.00 mL, 3.19 mmol), tetrazole (80 mg, 1.14 mmol), and N-methylimidazole (45 µL, 0.57 mmol). After stirring at room temperature for 3 hours, the mixture was treated with triethylamine (1.27 mL, 9.13 mmol), stirred for 5 minutes, and then poured into ethyl acetate (200 mL). The resulting solution was washed with 1:1 saturated aq. NaHCO$_3$:saturated aq. NaCl (1×200 mL), followed by saturated aq. NaCl (2×200 mL). The organic portion was dried over anhydrous Na$_2$SO$_4$, filtered, and evaporated. Silica gel chromatography (1:1 hexanes:ethyl acetate) yielded 1.58 g (80.1% yield) of Compound 13 as a pale yellow foam. $^1$H, $^{19}$F, and $^{31}$P NMR were consistent with the structure of Compound 13 as a mixture of phosphorous diastereomers.

Example 10

Preparation of Compound 20

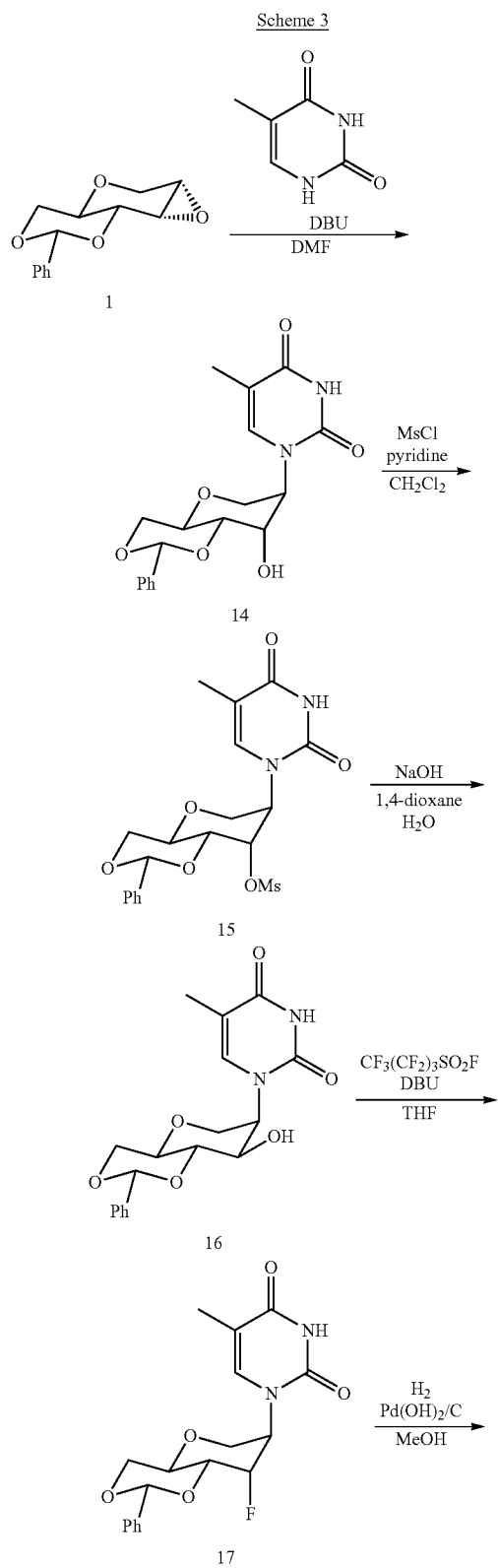

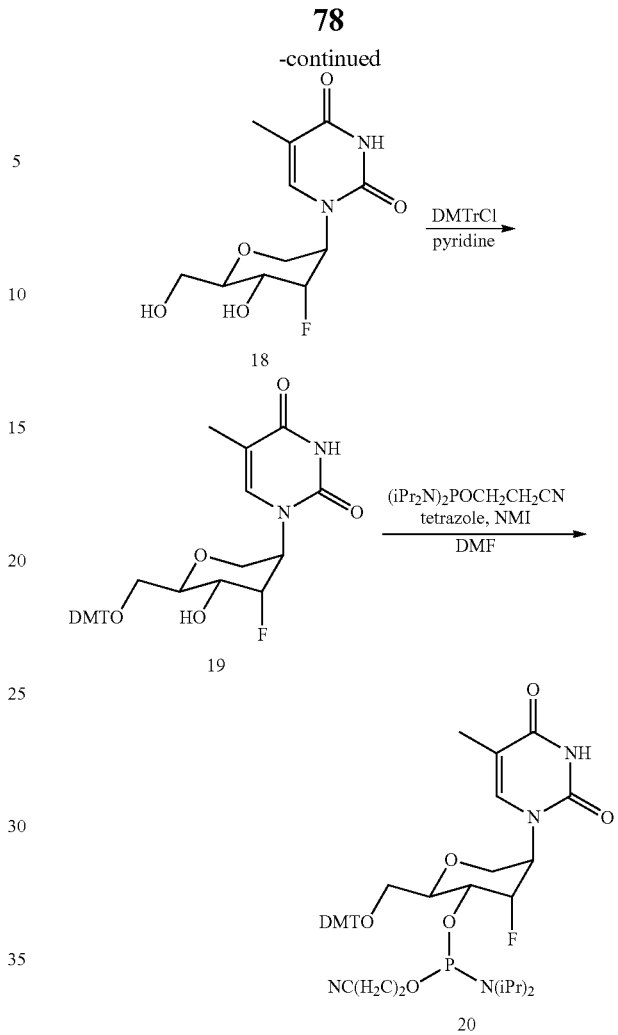

a) Preparation of Compound 14

Compound 1 (30.0 g, 128 mmol), was dissolved in anhydrous acetonitrile (600 mL). To this solution was added thymine (48.4 g, 384 mmol) and 1,8-diazabicyclo[5.4.0]undec-7-ene (57.4 mL, 384 mmol). This mixture was heated to 85° C. for 12 hours. After cooling to room temperature, unreacted thymine was removed by filtration. The filtered solution was concentrated in vacuo to a yellow oil, redissolved in $CH_2Cl_2$ (500 mL), washed with saturated aqueous $NaHCO_3$ (2×500 mL), dried over $Na_2SO_4$, filtered, and concentrated to a yellow oil. Silica gel chromatography (2% methanol in $CH_2Cl_2$) of the dried residue yielded 30.3 g (65.6%) of Compound 14 as an off-white foam. $^1$H NMR was consistent with structure. ESI-MS 1M+H$^+$1: calc. 361.4 Da; obs. 361.1 Da.

b) Preparation of Compound 15

Compound 14 (30.1 g, 83.6 mmol) was dissolved in a mixture of anhydrous $CH_2Cl_2$ (100 mL) and anhydrous pyridine (100 mL). This mixture was cooled to 0° C., then treated with methanesulfonyl chloride (8.4 mL, 109 mmol). The mixture was kept at 0° C. for 30 minutes, then warmed to room temperature and stirred for an additional 24 hours. The mixture was concentrated in vacuo to an orange oil, which was redissolved in $CH_2Cl_2$ (500 mL), washed with half-saturated aq. $NaHCO_3$ (2×500 mL), dried over anhydrous $Na_2SO_4$, filtered, and evaporated to a pale orange foam. $^1$H NMR was consistent with structure. ESI-MS 1M+H$^{11}$1: calc. 439.4 Da; obs. 439.1 Da. The resulting material was used for subsequent reaction without any additional purification.

c) Preparation of Compound 16

Compound 15 (approximately 34 g crude, 78 mmol) was suspended in 1,4-dioxane (125 mL). To this suspension was added 125 mL of 2M aqueous NaOH. The resulting mixture was warmed to 60° C. and stirred for 3 hours. The mixture was cooled to room temperature, then neutralized with acetic acid (14 mL). The mixture was concentrated in vacuo to ~75 mL, then poured into $CH_2Cl_2$ (1.75 L). The mixture was washed with saturated aq. $NaHCO_3$ (2×1.5 L), dried over anhydrous $Na_2SO_4$, filtered and evaporated to yield a yellow solid, which was used for subsequent reaction without any additional purification. ESI-MS [M+H$^+$]: calc. 361.4 Da; obs. 361.1 Da. $^1$H NMR was consistent with structure.

d) Preparation of Compound 17

Compound 16 (26.6 g crude, 73.8 mmol) was dissolved in anhydrous THF (450 mL). To this solution was added 1,8-diazabicyclo[5.4.0]undec-7-ene (16.5 mL, 111 mmol), followed by nonafluorobutanesulfonyl fluoride (34 mL, 111 mmol), which was added dropwise with stirring. This mixture was incubated at 30° C. for 42 hours. The resulting mixture was concentrated to ~75 mL, then poured into EtOAc (500 mL), washed with half-saturated aq. $NaHCO_3$ (2×500 mL), dried over anhydrous $Na_2SO_4$, filtered and evaporated to a brown oil. Silica gel chromatography (3:2 hexanes:ethyl acetate) yielded 18.1 g (67.8%) of Compound 17 as an impure mixture (~82% pure by both LCMS and $^1$H NMR). This mixture was used for subsequent reactions without further purification. ESI-MS [M+H$^+$]: calc. 363 Da; obs. 363 Da (major impurity [M+H$^+$]=343, consistent with elimination of HF).

e) Preparation of Compound 18

Impure Compound 17 (4.57 g, 12.6 mmol) was dissolved in methanol (300 mL). To this solution was added $Pd(OH)_2$/C (9 g). Flask was flushed with $H_2$ gas, sealed, and maintained with an $H_2$ atmosphere while stirring at room temperature. After 12 hours the $H_2$ gas was vented, $Pd(OH)_2$/C was removed by filtration through a celite plug, which was washed thoroughly with additional methanol. Concentrated in vacuo to a white foam. Silica gel chromatography (5% methanol in $CH_2Cl_2$), yielded 10.7 g (95%) of 18 as a white foam. ESI-MS [M+H$^+$]: calc. 275.2 Da; obs. 275.1 Da. Both $^1$H NMR and $^{19}$F NMR were consistent with structure.

f) Preparation of Compound 19

Compound 18 (10.6 g, 38.6 mmol) was dissolved in anhydrous pyridine (120 mL), cooled to 0° C. and treated with 4,4'-dimethoxytrityl chloride (26.1 g, 77.2 mmol). The resulting solution was slowly warmed to room temperature and stirred for 14 hours. The reaction mixture was quenched with methanol (10 mL) and concentrated in vacuo to a brown slush. The mixture was redissolved in $CH_2Cl_2$ (500 mL), washed with half-saturated aqueous $NaHCO_3$ (2×500 mL), dried over anhydrous $Na_2SO_4$, filtered and evaporated to a sticky brown foam. Silica gel chromatography (1% methanol in $CH_2Cl_2$) yielded 20.3 g (91%) of Compound 19 as a yellow foam. $^1$H NMR was consistent with structure.

g) Preparation of Compound 20

Compound 19 (9.00 g, 15.6 mmol) was dissolved in anhydrous N,N-dimethylformamide (37 mL) and 2-cyanoethyl-N,N,N',N'-tetraisopropylphosphorodiamidite (7.43 mL, 23.4 mmol), tetrazole (656 mg, 9.37 mmol), and N-methylimidazole (311 μL, 3.9 mmol) were added. After stirring at room temperature for 3 hours, the mixture was treated with triethylamine (8.7 mL, 62.4 mmol), stirred for 5 minutes, then poured into ethyl acetate (500 mL). The resulting solution was washed with half-saturated aqueous $NaHCO_3$ (3×500 mL), dried over anhydrous $Na_2SO_4$, filtered and evaporated to a sticky yellow foam. Silica gel chromatography (2:3 hexanes:ethyl acetate), followed by precipitation from hexanes/ethyl acetate yielded 10.5 g (87% yield) of Compound 20 as a pale yellow foam. $^1$H, $^{19}$F, and $^{31}$P NMR were consistent with the structure as a mixture of diastereomers.

Example 11

Preparation of Compound 25

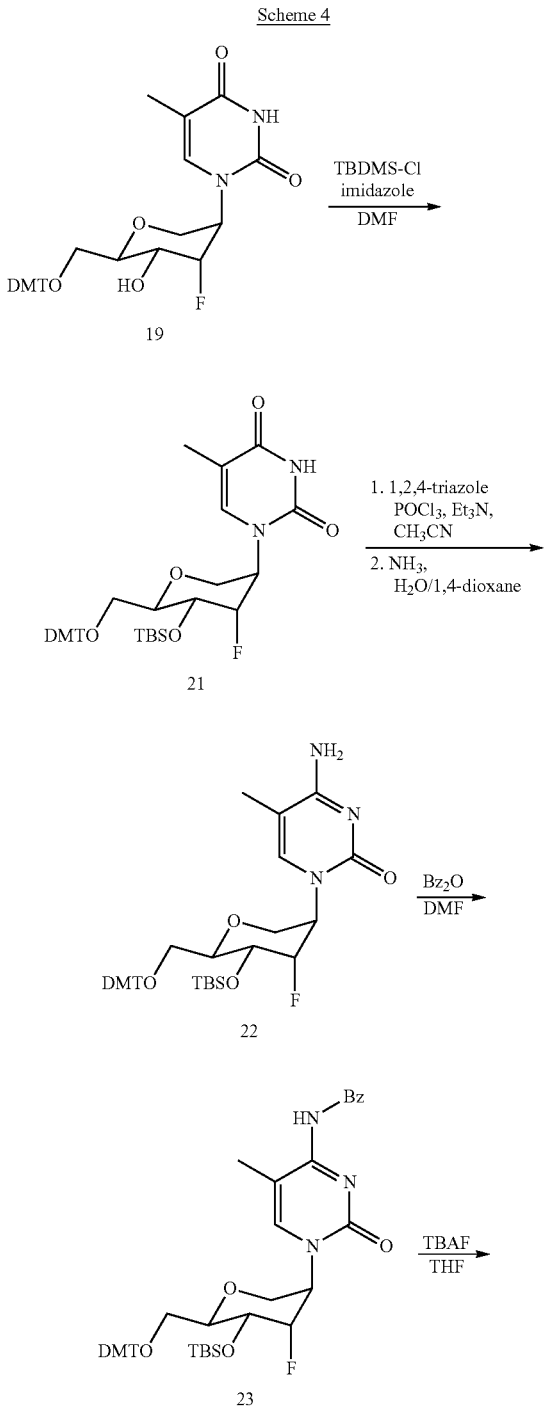

Scheme 4

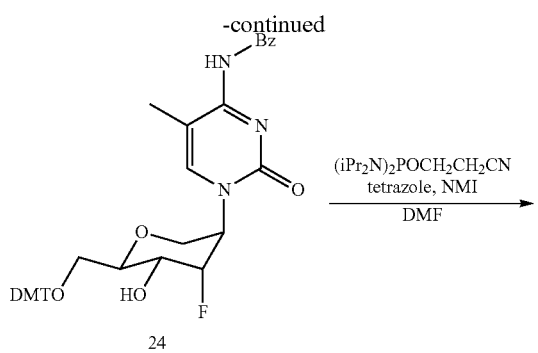

24

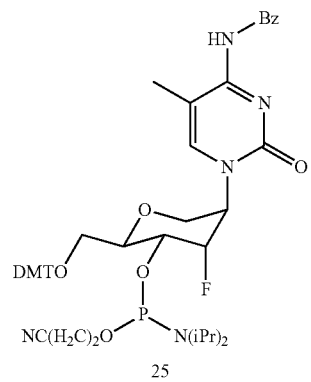

25 a) Preparation of Compound 21

Compound 19 (11.2 g, 19.4 mmol, prepared in the previous example) was dissolved in anhydrous N,N-dimethylformamide (44 mL). To this solution was added imidazole (7.9 g, 116 mmol) and tert-butyldimethylsilyl chloride (5.85 g, 38.8 mmol). After stirring at room temperature for 14 hours, quenched with the addition of methanol (10 mL), poured into ethyl acetate (500 mL), washed with half-saturated aq. NaHCO$_3$ (3×500 mL), dried over anhydrous Na$_2$SO$_4$, filtered, and evaporated to 13.2 g (98%) of Compound 21 as a pale yellow foam. $^1$H NMR was consistent with the indicated structure. Material was used for subsequent reaction without additional purification.

b) Preparation of Compound 22

To a chilled (0° C.) suspension of 1,2,4-triazole (18.4 g, 267 mmol) in anhydrous acetonitrile (350 mL) was added phosphorous oxychloride (7.1 mL, 76 mmol). After stirring at 0° C. for 30 minutes, triethylamine (53 mL, 382 mmol) was added to the mixture. To the resulting slurry was added a solution of Compound 21 (13.2 g, 19.1 mmol) in anhydrous acetonitrile (100 mL). The mixture was held at 0° C. for 1 hour, then warmed to room temperature for 3.5 hours. The mixture was subsequently concentrated to approximately half its original volume, poured into ethyl acetate (500 mL), washed with half-saturated aq. NaCl (2×500 mL), dried over anhydrous Na$_2$SO$_4$, filtered, and evaporated to a yellow foam. This residue was redissolved in 1,4-dioxane (175 mL) and treated with conc. aq. NH$_4$OH (175 mL). The reaction vessel was sealed and stirred at room temperature for 14 hours, at which time the mixture was concentrated under reduced pressure, poured into CH$_2$Cl$_2$ (500 mL), washed with half-saturated aq. NaHCO$_3$ (2×500 mL), dried over anhydrous Na$_2$SO$_4$, filtered, and evaporated to 12.4 g (94%) of Compound 22 as a yellow foam, which crystallized upon drying overnight. $^1$H NMR was consistent with structure. Material was used for subsequent reaction without additional purification.

c) Preparation of Compound 23

Compound 22 (12.3 g, 17.8 mmol) was dissolved in anhydrous N,N-dimethylformamide (60 mL). To the resulting solution was added benzoic anhydride (6.05 g, 26.7 mmol). After stirring at room temperature for 12 hours, the mixture was poured into ethyl acetate (500 mL), washed with half-saturated aq. NaHCO$_3$ (3×500 mL), dried over anhydrous Na$_2$SO$_4$, filtered and evaporated. Silica gel chromatography (3:1 hexanes:ethyl acetate) yielded 13.4 g (95.1%) of Compound 23 as a white foam. $^1$H NMR was consistent with structure.

d) Preparation of Compound 24

Compound 23 (13.4 g, 16.9 mmol) was dissolved in anhydrous THF (14 mL). To this solution was added 22 mL of 1 M tetrabutylammonium fluoride in THF. After 5 hours, the mixture was evaporated, then subjected to silica gel chromatography. Elution with 2:1 hexanes:ethyl acetate yielded 9.57 g (83.2%) of Compound 24 as a white foam. $^1$H NMR was consistent with structure.

e) Preparation of Compound 25

Compound 24 (9.5 g, 14.0 mmol) was dissolved in anhydrous N,N-dimethylformamide (33 mL). To this solution was added 2-cyanoethyl-N,N,N',N'-tetraisopropylphosphorodiamidite (6.7 mL, 21.0 mmol), tetrazole (589 mg, 8.41 mmol), and N-methylimidazole (279 µL, 3.50 mmol). After stirring at room temperature for 3 hours, the mixture was treated with triethylamine (7.8 mL, 56 mmol), stirred for 5 minutes, then poured into ethyl acetate (500 mL). The resulting solution was washed with saturated aq. NaCl (3×500 mL), dried over anhydrous Na$_2$SO$_4$, filtered, and evaporated. Silica gel chromatography (3:1 hexanes:ethyl acetate) yielded 11.8 g (95% yield) of Compound 25 as a white foam. $^1$H and $^{31}$P NMR were consistent with the structure of Compound 25 as a mixture of phosphorous diastereomers.

Example 12

Preparation of Compound 33

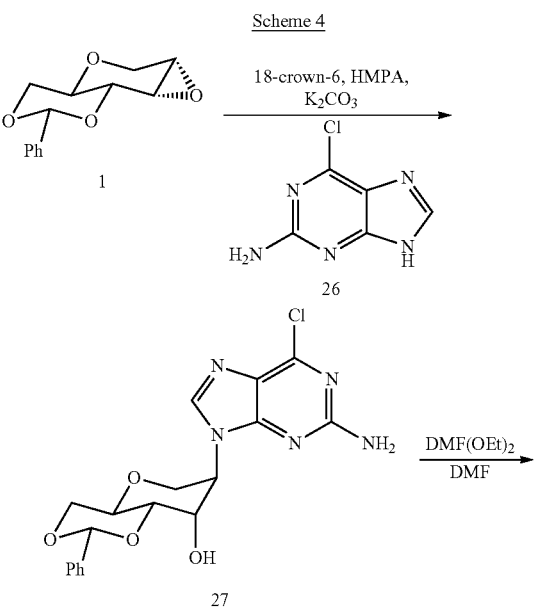

-continued

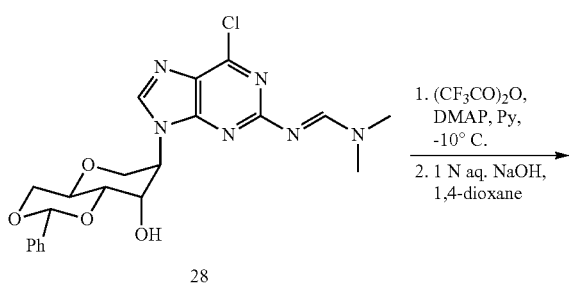
28

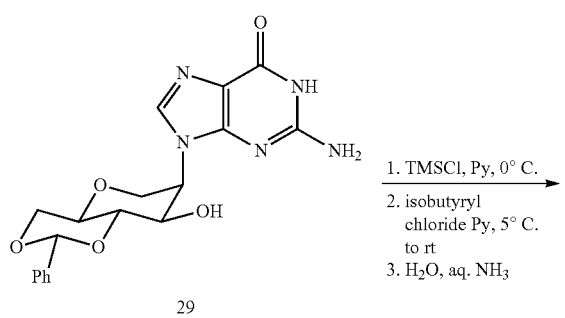
29

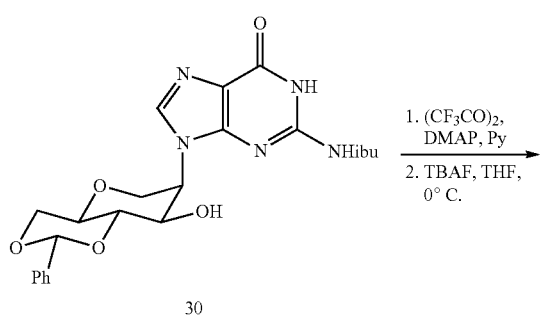
30

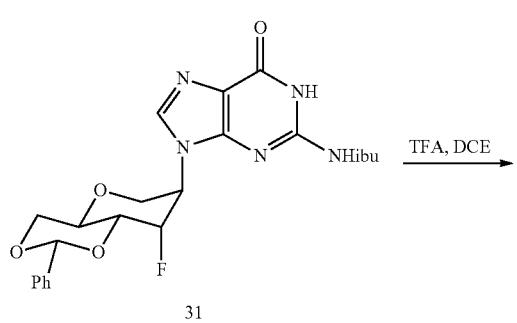
31

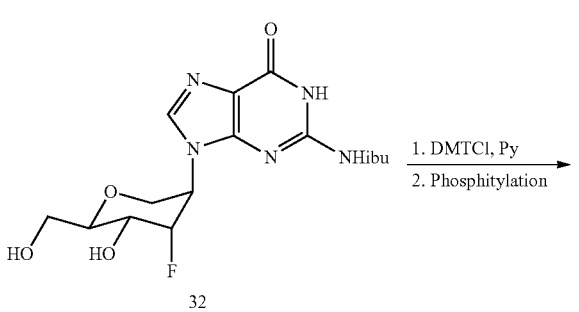
32

-continued

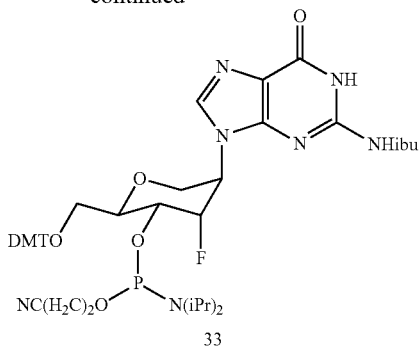
33 a) Preparation of Compound 27

Compound 1 (5.40 g, 4.56 mmol, 1,5:2,3-dianhydro-4,6-O-benzylidene-D-allitol, purchased from Carbosynth, UK) was mixed with 2-amino-6-chloropurine Compound 26 (5.89 g, 34.69 mmol) and dried over $P_2O_5$ under reduced pressure overnight. The mixture was suspended in anhydrous hexamethyl phosphoramide (86 mL) and 18-crown-6 (2.86 g, 10.82 mmol) and $K_2CO_3$ (3.46 g, 25.04 mmol) was added. The reaction mixture was stirred at 90° C. for 3 hours and allowed to equilibrate to room temperature. Crushed ice was added with subsequent stirring for 1 hour. The precipitate formed was filtered and washed with cold water followed by diethyl ether. The crude material was purified by silica gel column chromatography eluting with 5% MeOH in $CH_2Cl_2$ to yield Compound 27 (7.01 g, 75%). $^1$H NMR (300 MHz, DMSO-$d_6$) δ 3.61 (m, 1H), 3.78 (t, J=10.1 Hz, 1H), 3.92 (m, 1H), 4.18-4.28 (m, 4H), 5.63 (1, 1H), 5.83 (d, J=4.2 Hz, 1H), 5.40 (d, J=6.3 Hz, 1H), 5.85 (d, J=3.8 Hz, 1H), 6.99 (s, 2H), 7.31-7.42 (m, 5H), 8.21 (s, 1H); MS (ES) m/z 404.0 [M+H]$^-$.

Example 13

Preparation of Compound 41

Scheme 5

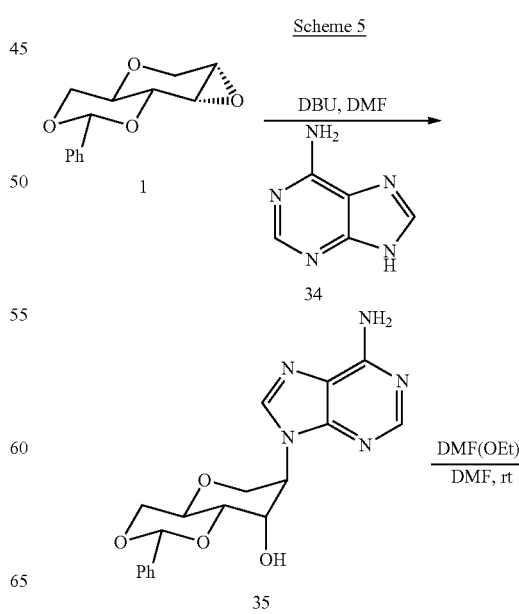

-continued
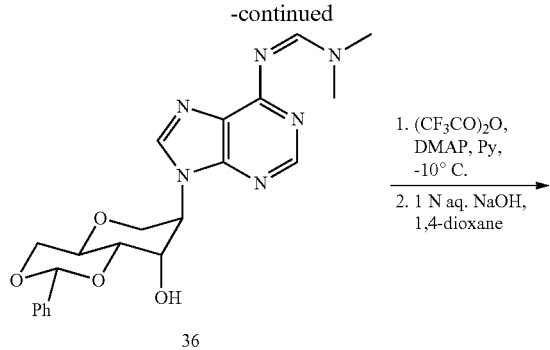
36
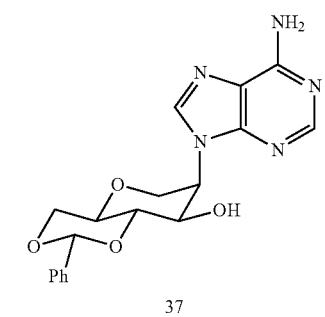
37
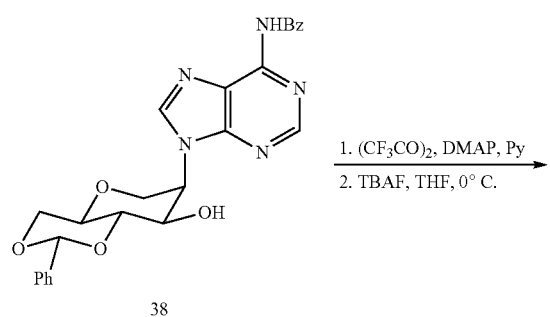
38
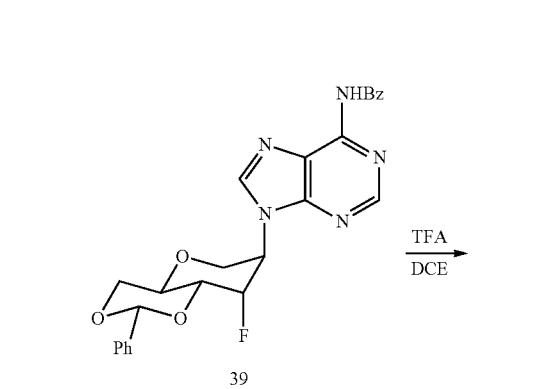
39
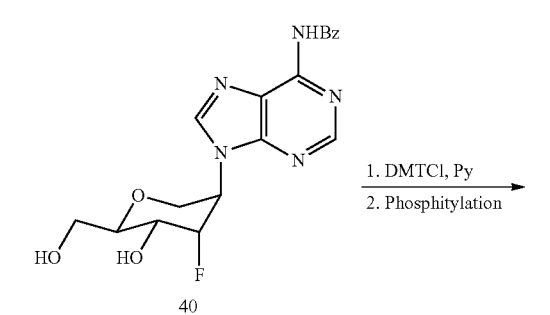
40
-continued
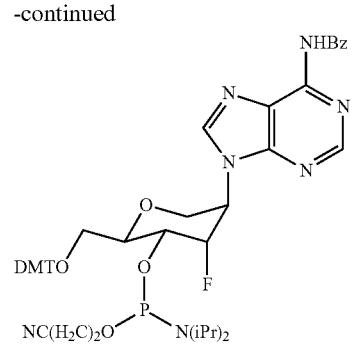
41
Compound 1, 1,5:2,3-dianhydro-4,6-O-benzylidene-D-allitol, is purchased from Carbosynth, UK.
Example 14
Preparation of Compound 49
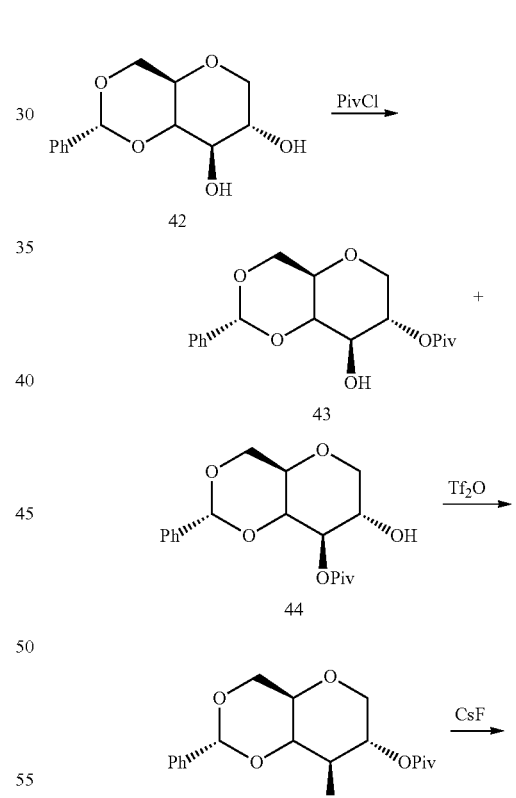
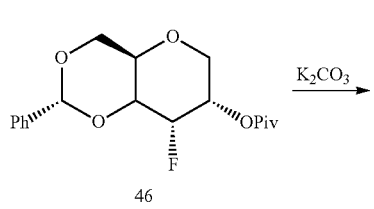
46

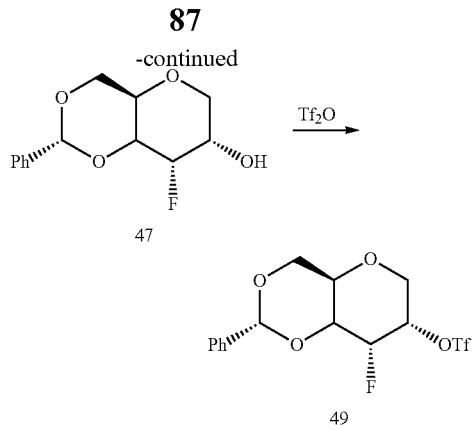

(300 MHz, chloroform-d) δ=7.53-7.42 (m, 2H), 7.42-7.32 (m, 3H), 5.59 (s, 1H), 5.10 (s, 2H), 4.48-4.33 (m, 1H), 4.32-4.15 (m, 1H), 3.90-3.69 (m, 2H), 3.57-3.42 (m, 1H), 3.40-3.22 (m, 1H), 1.24 (s, 9H).

A solution of Compound 45 and cesium fluoride (10 mmol, 1.5 g) in t-BuOH (10 mL) was heated at 70° C. for 2 hours. The reaction was then cooled to room temperature, diluted with ethyl acetate and the organic layer was washed with water and brine then dried (Na$_2$SO$_4$) and concentrated. Purification by column chromatography (silica gel, eluting with 10 to 20% ethyl acetate in hexanes) provided Compound 46 (0.94 g, 90% from 43). $^1$H NMR (300 MHz, chloroform-d) δ=7.49 (m, 2H), 7.37 (m, 3H), 5.56 (s, 1H), 5.29-5.02 (m, 1H), 5.02-4.81 (m, 1H), 4.49-4.32 (m, 1H), 4.22-4.04 (m, 1H), 3.99-3.54 (m, 7H), 1.23 (s, 9H).

c) Preparation of Compound 49

Potassium carbonate (3.2 mmol, 0.44 g) was added to a solution of compound 46 (1.18 mmol, 0.4 g) in methanol (10 mL). After stirring at room temperature for 3 hours, the solvent was evaporated under reduced pressure and the residue was partitioned between ethyl acetate and water. The organic layer was dried (Na$_2$SO$_4$) and concentrated to provide Compound 47 which was used without any further purification. $^1$H NMR (300 MHz, chloroform-d) δ=7.58-7.30 (m, 5H), 5.54 (s, 1H), 5.23-4.94 (m, 1H), 4.39 (dd, J=4.7, 10.0 Hz, 1H), 4.02-3.43 (m, 6H), 2.25-2.08 (m, 1H).

Trifluoromethanesulfonic anhydride (0.45 mmol, 0.08 mL) was added to a cold (0° C.) solution of compound 47 (0.3 mmol, 0.08 g) and pyridine (0.05 mL). After stirring for one hour, the reaction was quenched by adding water and the organic layer was washed with water and brine then dried (Na$_2$SO$_4$) and concentrated to provide crude 49 which was used without any further purification. $^1$H NMR (300 MHz, chloroform-d) δ=7.58-7.32 (m, 5H), 5.55 (s, 1H), 5.28 (1H, d, J=55 Hz), 5.02-4.85 (m, 1H), 4.42 (dd, J=4.9, 10.4 Hz, 1H), 4.09 (dd, J=5.7, 10.8 Hz, 1H), 4.01-3.80 (m, 2H), 3.78-3.50 (m, 2H); MS (e/z), 387 (m+1).

a) Preparation of Compound 43

Pivaloyl chloride (5.5 mmol, 0.67 mL) was added to a solution of commercially available 1,5-anhydro-4,6-O-benzylidene-D-glucitol (Carbosynth Limited, UK.) Compound 42 (5 mmol, 1.25 g), triethylamine (5.5 mmol, 0.77 mL) and dimethylaminopyridine (20 mg) in dichloromethane (25 mL). After stirring at room temperature for 24 hours, the reaction was diluted with dichloromethane and washed with 5% HCl, saturated sodium bicarbonate and brine then dried (Na$_2$SO$_4$) and concentrated. Purification by column chromatography (silica gel, eluting with 10 to 30% ethyl acetate in hexanes) provided Compound 43 (1.06 g) and Compound 44 (0.64 g) as white solids. Compound 43: $^1$H NMR (300 MHz, chloroform-d) δ=7.56-7.44 (m, 2H), 7.36 (m, 3H), 5.49 (s, 1H), 4.98-4.81 (m, 1H), 4.40-4.22 (m, 1H), 4.16-3.99 (m, 1H), 3.82 (s, 1H), 3.65 (s, 1H), 3.46 (s, 1H), 3.41-3.27 (m, 1H), 3.27-3.15 (m, 1H), 3.04-2.80 (m, 1H), 1.29-1.16 (m, 9H). Compound 44: $^1$H NMR (300 MHz, chloroform-d) δ=7.49-7.40 (m, 2H), 7.39-7.32 (m, 3H), 5.53 (s, 1H), 5.08-4.91 (m, 1H), 4.42-4.29 (m, 1H), 4.19-4.04 (m, 1H), 3.92-3.76 (m, 1H), 3.76-3.55 (m, 2H), 3.50-3.30 (m, 2H), 1.24 (s, 9H).

b) Preparation of Compound 46

Trifluoromethanesulfonic anhydride (4.8 mmol, 0.8 mL) was added to a cold (0° C.) solution of Compound 43 (3.2 mmol, 1.07 g) and pyridine (0.5 mL). After stirring for one hour the reaction was quenched by adding water and the organic layer was washed with water and brine then dried (Na$_2$SO$_4$) and concentrated to provide crude Compound 45 which was used without any further purification. $^1$H NMR Example 15

Preparation of Compound 49 (Alternate Route)

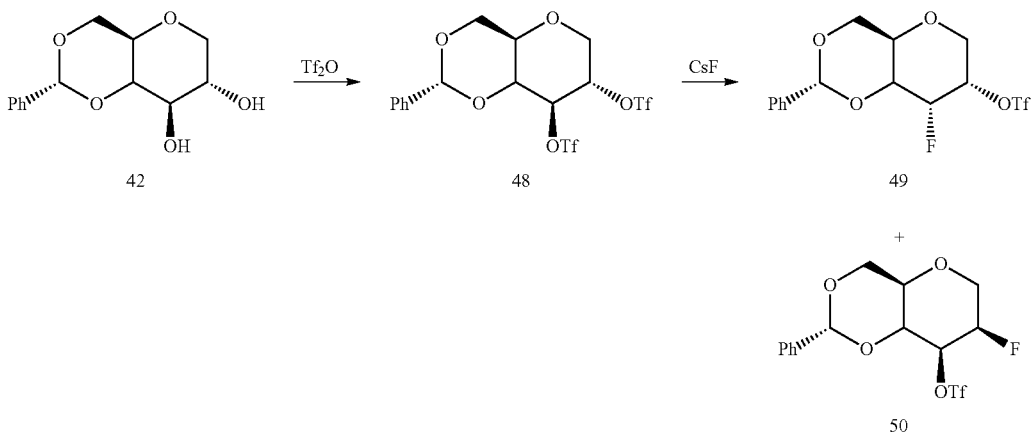

a) Preparation of Compound 48

Trifluoromethanesulfonic anhydride (12.0 mmol, 2.0 mL) was added to a cold (0° C.) dichloromethane solution (40 mL) of Compound 42 (4.0 mmol, 1.0 g) and pyridine (16 mmol., 1.3 mL). After stirring for one hour, the reaction was quenched by adding water and the organic layer was washed with water and brine then dried and concentrated to provide crude Compound 48 (2.24 g, quantitative) which was used without any further purification. $^1$H NMR (CDCl$_3$): δ 7.52-7.45 (m, 2H), 7.41-7.35 (m, 3H), 5.58 (s, 1H), 5.08 (1H, t, J=9 Hz), 5.06-4.91 (m, 1H), 4.50-4.25 (m, 2H), 3.83-3.69 (m, 2H), 3.65-3.43 (m, 2H). MS (e/z), 517 (m+1).

b) Preparation of Compounds 49 and 50

Compound 48 (2.05 mmol, 1.1 g) and CsF (6.2 mmol., 0.94 g) were mixed with dry t-butanol (15 mL) and the mixture was stirred at 90° C. for 25 minutes. The reaction was cooled to room temperature and extracted with ethyl acetate. The ethyl acetate solution was concentrated to dryness and the residue was purified by silica gel chromatography by eluting with 5% ethyl acetate in hexanes. Compound 49 was obtained as clear oil (0.47 g, 59% yield). $^1$H NMR (300 MHz, chloroform-d) δ=7.58-7.32 (m, 5H), 5.55 (s, 1H), 5.28 (1H, d, J=55 Hz), 5.02-4.85 (m, 1H), 4.42 (dd, J=4.9, 10.4 Hz, 1H), 4.09 (dd, J=5.7, 10.8 Hz, 1H), 4.01-3.80 (m, 2H), 3.78-3.50 (m, 2H); MS (e/z), 387 (m+1). Compound 50 was obtained as a white solid (0.14 g, 18% yield). $^1$H NMR (CDCl$_3$): δ 7.50-7.43 (m, 2H), 7.40-7.34 (m, 3H), 5.64 (s, 1H), 5.15-4.90 (m, 2H), 4.45-4.15 (m, 3H), 3.80-3.52 (m, 2H), 3.55-3.40 (m, 1H). MS (e/z), 387 (m+1).

Example 16

Preparation of Compound 58a

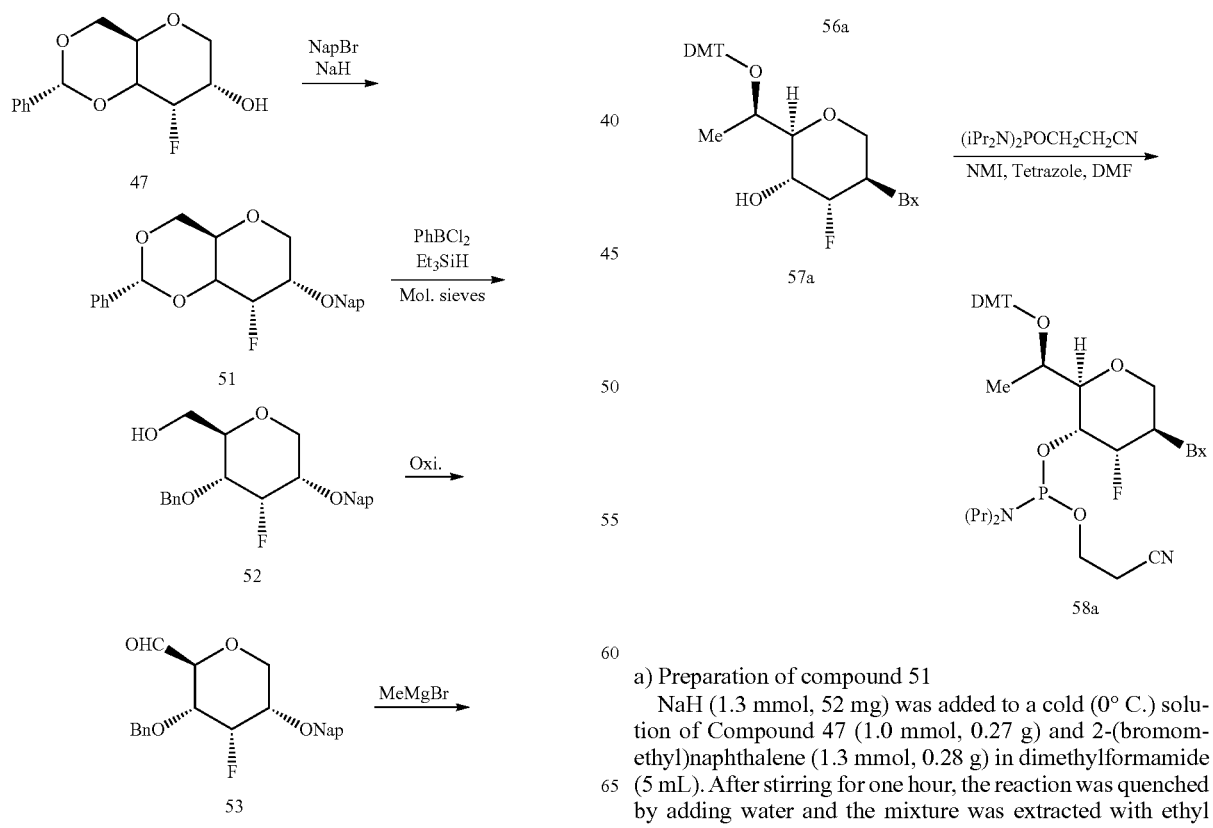

a) Preparation of compound 51

NaH (1.3 mmol, 52 mg) was added to a cold (0° C.) solution of Compound 47 (1.0 mmol, 0.27 g) and 2-(bromomethyl)naphthalene (1.3 mmol, 0.28 g) in dimethylformamide (5 mL). After stirring for one hour, the reaction was quenched by adding water and the mixture was extracted with ethyl acetate. The ethyl acetate solution was washed with water and brine then dried and concentrated to provide crude Compound 51 which was purified by silica gel column chromatography by eluting with 5% ethyl acetate in hexanes. Compound 51 was obtained as a white solid (0.4 g, quantitative). $^1$H NMR (CDCl$_3$): δ 8.0-7.25 (m, 12H), 5.47 (s, 1H), 5.17 (1H, d, J=54 Hz), 4.87-4.76 (m, 2H), 4.40-4.30 (m, 1H), 3.95-3.78 (m, 2H), 3.75-3.56 (m, 2H), 3.51-3.39 (m, 2H). MS (e/z), 395, 417 (m+1, m+23).

b) Preparation of Compound 52

Molecular sieves 4A (powder, 4.45 g) were placed in a 100 mL flask with heating at 140° C. over four hours with vacuation. After cooling to room temperature, Compound 51 and dichloromethane (15 mL) were added. After stirring for one hour at room temperature, the mixture was cooled to −78° C., and Et$_3$SiH (4.11 mmol. 0.66 mL) and PhBCl$_2$ (3.63 mmol. 0.48 mL) were added successively with constant stirring. The mixture was stirred for an additional 10 minutes at −78° C. and 30% H$_2$O$_2$ (12.6 mmol. 1.6 mL) was added. After filtration, the reaction mixture was extracted with dichloromethane. The organic solution was washed with water and brine then dried and concentrated to provide crude Compound 52 which was purified by silica gel column chromatograph by eluting with 1% acetone in dichloromethane. Compound 52 was obtained as a white solid (0.31 g, 62%). $^1$H NMR (CDCl$_3$): δ 7.87-7.77 (m, 4H), 7.52-7.46 (m, 3H), 7.40-7.30 (m, 5H), 5.14 (1H, d, J=54 Hz), 4.83-4.52 (m, 4H), 3.90-3.83 (m, 2H), 3.73-3.66 (m, 3H), 3.56-3.34 (m, 2H), 1.68 (1H, t, J=6 Hz). MS (e/z), 419 (m+23).

c) Preparation of Compound 53

Compound 52 (0.025 mmol. 0.01 g) was dissolved in dichloromethane (0.3 mL), Dess-Martin reagent (0.025 mmol. 0.01 g) was added. The reaction was stirred at room temperature for 10 minute and concentrated to provide Compound 53. $^1$H NMR (CDCl$_3$): δ 9.70 (s, 1H), 8.1-7.3 (m, 12H), 5.17 (1H, d, J=54 Hz), 4.80 (s, 2H), 4.45-4.75 (m, 2H), 4.25-4.20 (m, 1H), 4.0-3.90 (m, 1H), 3.85-3.35 (m, 3H).

d) Preparation of Compound 58a

Compounds 54a and 54b are prepared from Compound 53 by adding MeMgBr in the presence of Cerium chloride. Alternately, compounds 54a and 54b can be interconverted to each other by means of a Mitsunobu reaction. The secondary hydroxyl group in 54a is protected as an ester, preferably as an isobutyryl ester and the 2'O-naphthyl group is removed using DDQ followed by reaction with triflic anhydride to provide Compound 55a. Reaction with a suitably protected nucleobase and a strong base such as sodium hydride in a solvent such as DMSO at temperatures between 50 and 100° C., followed by removal of the benzyl group using catalytic hydrogenation and reprotection as the silyl ether provides Compound 56a. Removal of the isobutyryl group using methanolic ammonia or potassium carbonate in methanol followed by reaction with DMTCl and lutidine and pyridine as the solvent at temperatures between 25 and 50 degree celcius followed by removal of the silyl protecting group using triethylamine trihydrofluoride provides Compound 57a. A phosphitylation reaction provides the phosphoramidite, Compound 58a.

Example 17

Preparation of Compound 58b

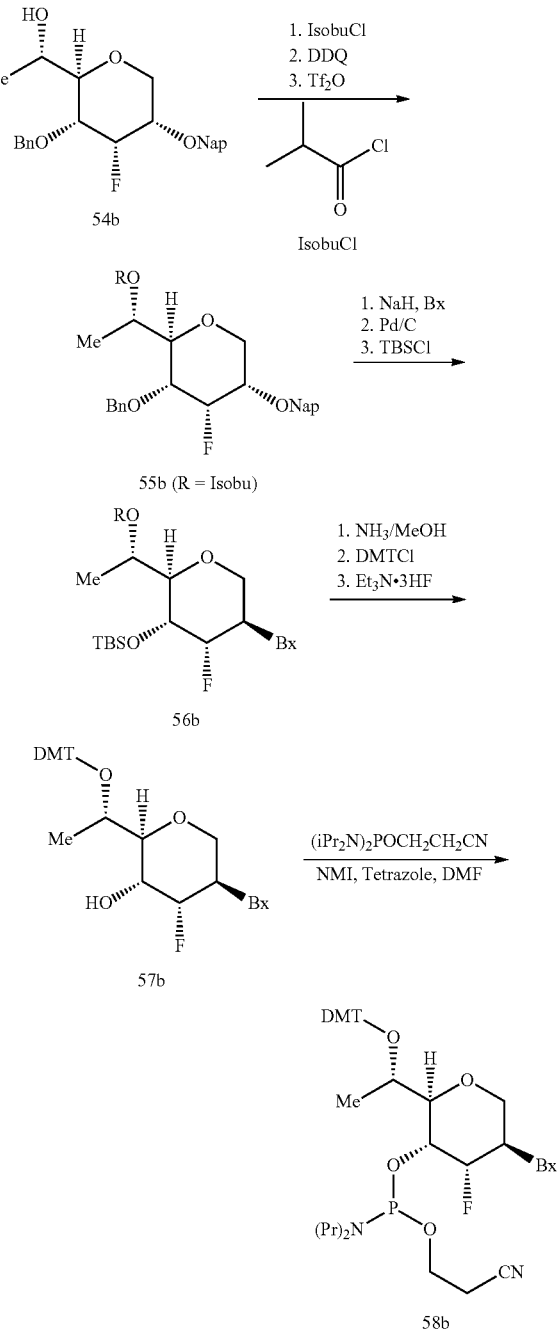

Compounds 54a and 54b are prepared from aldehyde 53 by adding MeMgBr in the presence of Cerium chloride. Alternately, compounds 54a and 54b can be interconverted to each other by means of a Mitsunobu reaction. The secondary hydroxyl group in 54b is protected as an ester, preferably as an isobutyryl ester and the 2'O-naphthyl group is removed using DDQ followed by reaction with triflic anhydride to provide Compound 55b. Reaction with a suitably protected nucleobase and a strong base such as sodium hydride in a solvent such as DMSO at temperatures between 50 and 100° C., followed by removal of the benzyl group using catalytic hydrogenation and reprotection as the silyl ether provides Compound 56b. Removal of the isobutyryl group using methanolic ammonia or potassium carbonate in methanol followed by reaction with DMTCl and lutidine and pyridine as the solvent at temperatures between 25 and 50 degree Celsius followed by removal of the silyl protecting group using triethylamine trihydrofluoride provides Compound 57b. A phosphitylation reaction provides phosphoramidite 58b.

Example 18

Preparation of Compound 63

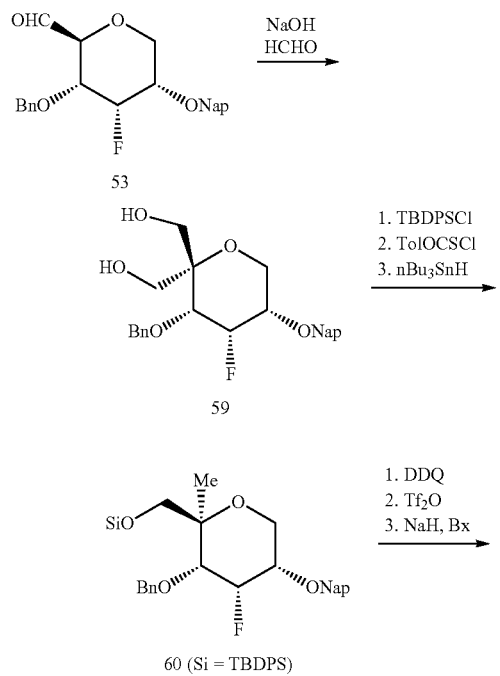

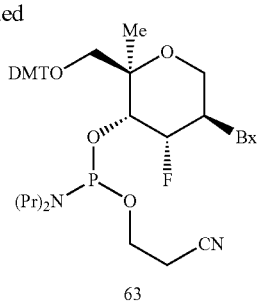

a) Preparation of Compound 59

Compound 53 (0.7 mmol. 0.27 g) was dissolved in THF (2 mL), water (0.7 mL), HCHO (0.7 mL), and 4 N NaOH (aq., 0.7 mL) was added. The reaction was stirred at room temperature for three days. The reaction was extracted with ethyl acetate and washed with water and brine then dried and concentrated to provide crude 59 which was purified by silica gel column chromatograph by eluting with 10% acetone in dichloromethane. Compound 59 was obtained as a white solid (0.19 g, 64%). $^1$H NMR (CDCl$_3$): 7.94-7.80 (m, 4H), 7.61-7.45 (m, 3H), 7.42-7.21 (m, 5H), 5.20 (1H, d, J-54 Hz), 4.49-4.40 (m, 4H), 4.20-3.35 (m, 11H), 2.10-1.95 (m, 1H), 1.90-1.75 (m, 1H).

b) Preparation of Compound 63

Reaction of Compound 59 with TBDPSCl provides a mixture of mono silylated products which are separated and the hydroxyl group is deoxygenated by means of a Barton deoxygenation reaction to provide Compound 60. Removal of the 2'O-naphthyl group with DDQ followed by triflation and reaction with a suitably protected nucleobase and a strong base such as sodium hydride in a solvent such as DMSO at temperatures between 50 and 100° C. provides Compound 61. Removal of the silyl protecting group using triethylamine trihydrofluoride followed by removal of the benzyl group by catalytic hydrogenation provides Compound 62. Protection of the primary hydroxyl group as the DMT ether followed by a phosphitylation reaction provides the phosphoramidite, Compound 63.

Example 19

Preparation of Compound 68

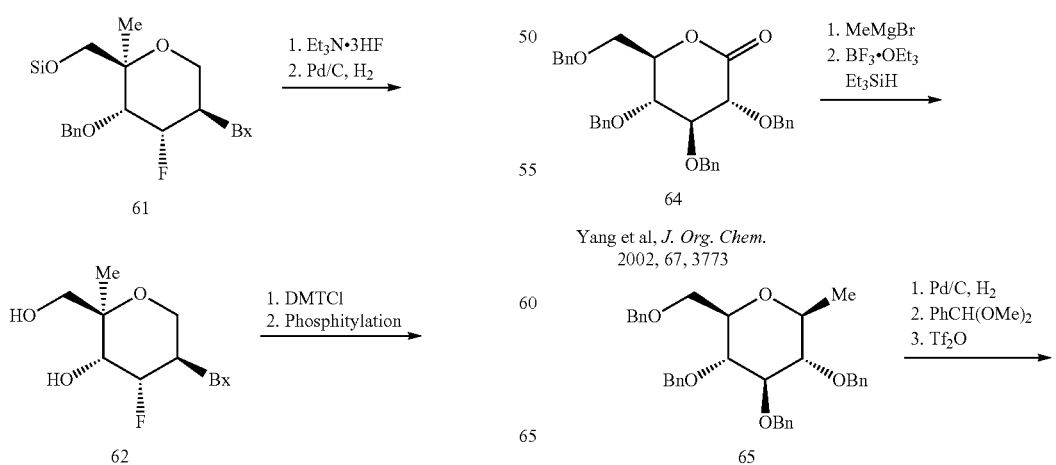

Yang et al, *J. Org. Chem.* 2002, 67, 3773

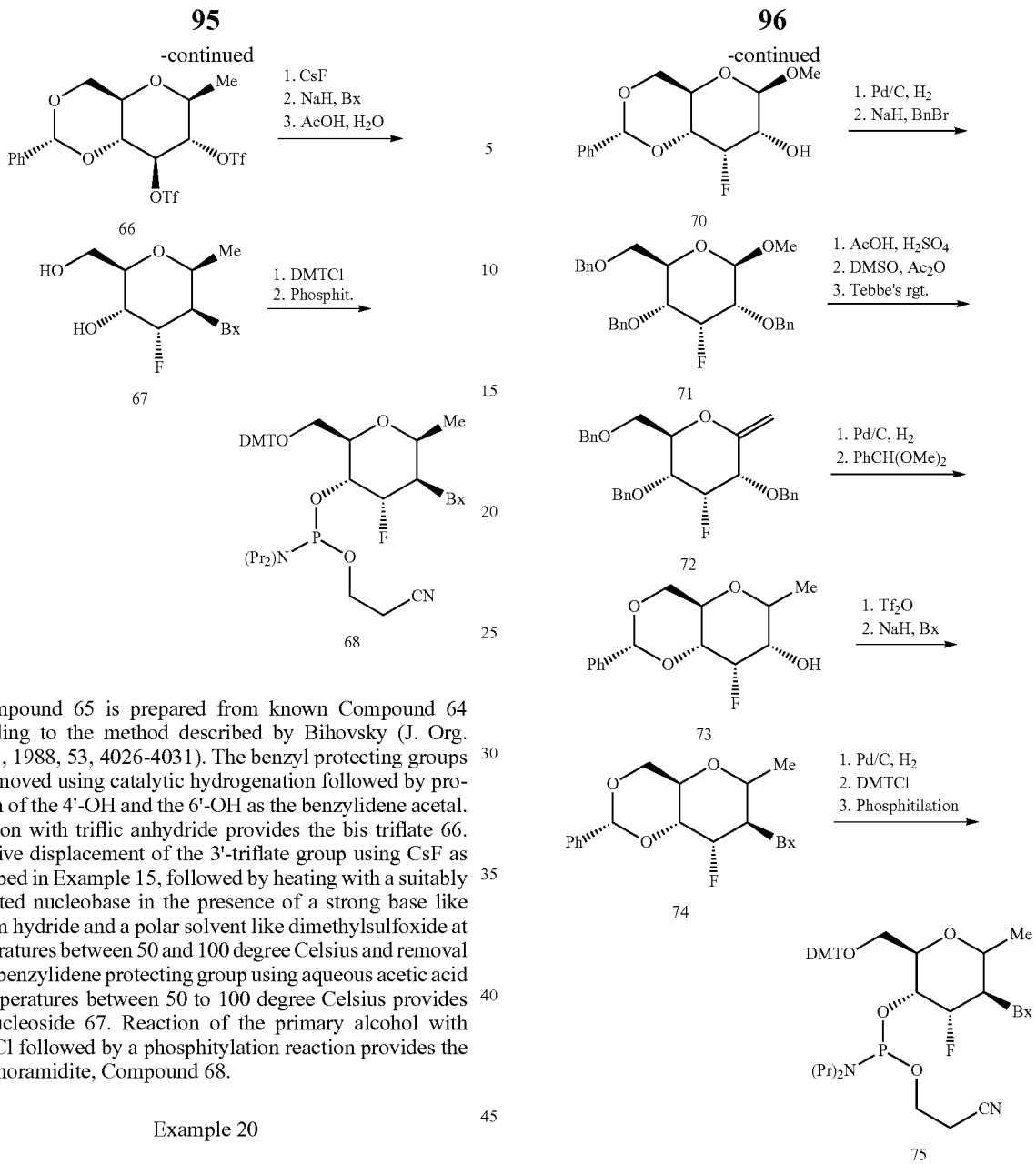

Compound 65 is prepared from known Compound 64 according to the method described by Bihovsky (J. Org. Chem., 1988, 53, 4026-4031). The benzyl protecting groups are removed using catalytic hydrogenation followed by protection of the 4'-OH and the 6'-OH as the benzylidene acetal. Reaction with triflic anhydride provides the bis triflate 66. Selective displacement of the 3'-triflate group using CsF as described in Example 15, followed by heating with a suitably protected nucleobase in the presence of a strong base like sodium hydride and a polar solvent like dimethylsulfoxide at temperatures between 50 and 100 degree Celsius and removal of the benzylidene protecting group using aqueous acetic acid at temperatures between 50 to 100 degree Celsius provides the nucleoside 67. Reaction of the primary alcohol with DMTCl followed by a phosphitylation reaction provides the phosphoramidite, Compound 68.

Example 20

Preparation of Compound 75

Compound 69 is prepared by reacting commercially available Methyl-fl-D-glucopyranose with dimethylbenzylidene acetal in the presence of p-toluenesulfonic acid at temperatures between 60 and 80 degree Celsius. Selective protection of Compound 69 with pivaloyl chloride, triflation, displacement with CsF and hydrolysis of the pivaloyl ester with potassium carbonate in methanol as described in Example 14 provides Compound 70. Removal of the benzylidene protecting group followed by reprotection of the hydroxyl groups as the benzyl ether provides Compound 71. Hydrolysis of the OMe acetal by heating with acetic acid and aqueous sulfuric acid followed by oxidation of the lactol with acetic anhydride in DMSO and an olefination reaction with Tebbe's or Petassis's reagent provides the olefin 72. Reduction of the vinyl group and removal of the benzyl protecting groups using catalytic hydrogenation followed by reprotection of the 4'OH and the 6'OH as the benzylidene acetal provides Compound 73. Triflation with triflic anhydride followed by reaction with a suitably protected nucleobase and a strong base such as sodium hydride in a solvent such as DMSO at temperatures between 50 and 100° C. provides Compound 74. Removal of the benzylidene protecting group using catalytic hydrogenation, protection of the primary alcohol as the DMT ether and a phosphitylation reaction provides the phosphoramidite Compound 75.

Example 21

Preparation of Compound 81

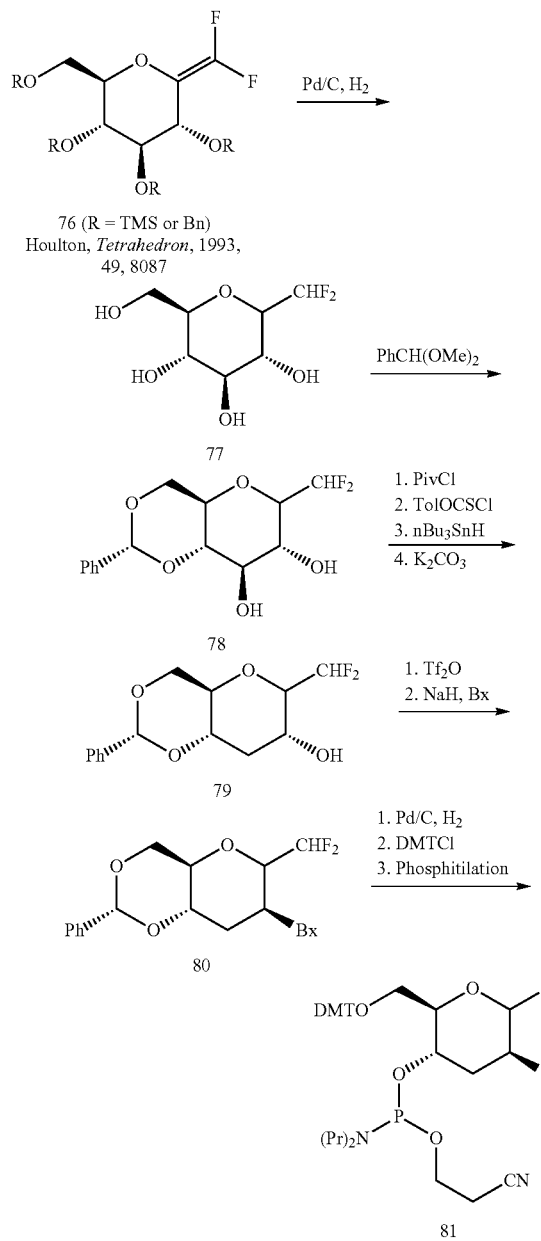

Compound 76 is prepared according to the procedure described by Houlton (Tetrahedron, 1993, 49, 8087) and is reduced to Compound 77 by means of a catalytic hydrogenation reaction. Protection of the 4'OH and the 6'OH as the benzylidene acetal provides Compound 78. Treatment of the 2'OH with pivaloyl chloride according to method described in Example 14 followed by Barton deoxygenation of the 3'OH group and hydrolysis of the pivaloyl ester provides Compound 79. Triflation with triflic anhydride followed by reaction with a suitably protected nucleobase and a strong base such as sodium hydride in a solvent such as DMSO at temperatures between 50 and 100° C. provides Compound 80. Removal of the benzylidene protecting group using catalytic hydrogenation, protection of the primary alcohol as the DMT ether and a phosphitylation reaction provides the phosphoramidite, Compound 81.

Example 22

Preparation of Compound 85

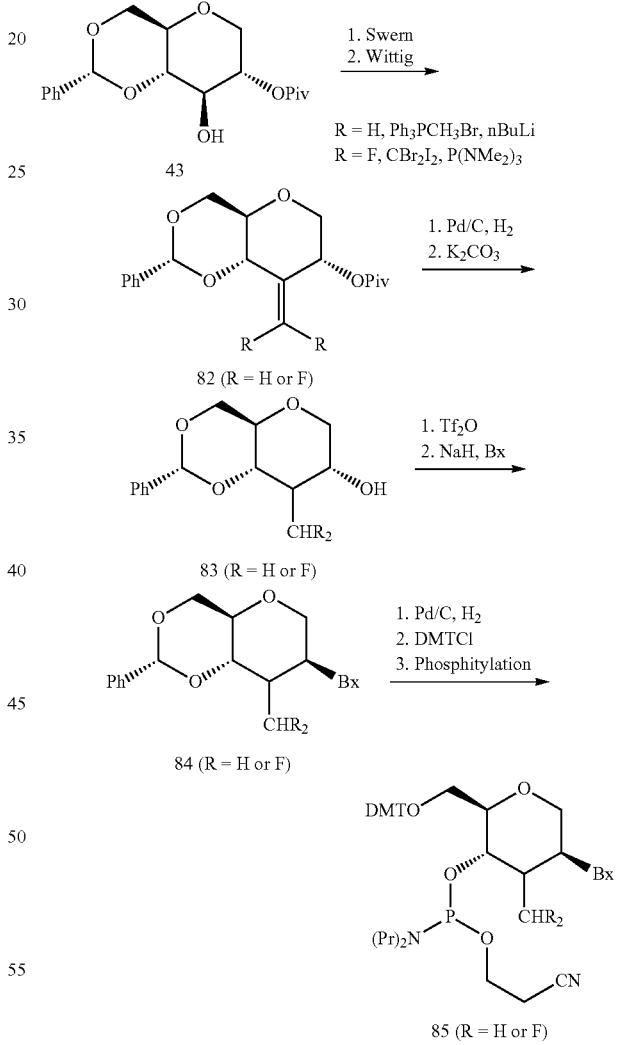

Oxidation of Compound 43 (prepared as per the procedures illustrated in Example 14) followed by a Wittig reaction provides Compound 82. Reduction of the olefin by means of a catalytic hydrogenation reaction followed by removal of the pivaloyl group with potassium carbonate in methanol provides Compound 83. Triflation with triflic anhydride followed by reaction with a suitably protected nucleobase and a strong base such as sodium hydride in a solvent such as DMSO at temperatures between 50 and 100° C. provides Compound 84. Removal of the benzylidene protecting group using catalytic hydrogenation, protection of the primary alcohol as the DMT ether and a phosphitylation reaction provides the phosphoramidite, Compound 85.

Example 23

Preparation of Compound 92

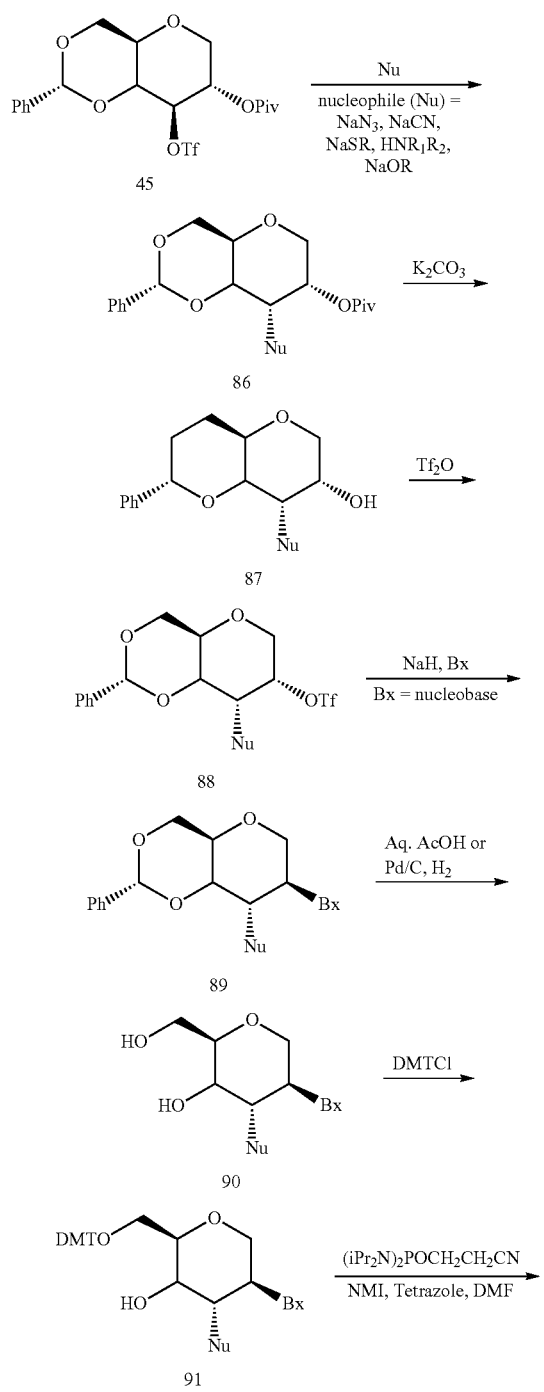

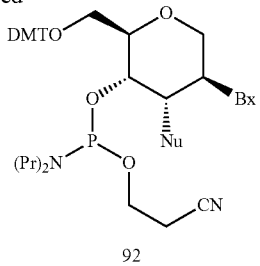

Compound 45 (prepared as per the procedures illustrated in Example 14) is reacted with a suitable nucleophile such as sodium azide, sodium cyanide, sodium sulfide, a primary or secondary amine derivative or sodium methoxide provides Compound 86 wherein the nucleophile (Nu) can be selected from any desired nucleophile which can include such nucleophiles as azide, cyanide, thiol, thioether, amine or alkoxide. Hydrolysis of the pivaloyl group using potassium carbonate provides Compound 87. Triflation of the hydroxyl group using triflic anhydride provides Compound 88. Reaction with a suitably protected nucleobase and a strong base such as sodium hydride in a solvent such as DMSO at temperatures between 50 and 100° C. provides Compound 89. Removal of the benzylidene protecting group using catalytic hydrogenation or by heating with aqueous acetic acid provides Compound 90. Protection of the primary alcohol as the DMT ether provides Compound 91 followed by a phosphitylation reaction provides the phosphoramidite, Compound 92.

Example 24

Preparation of Compound 99

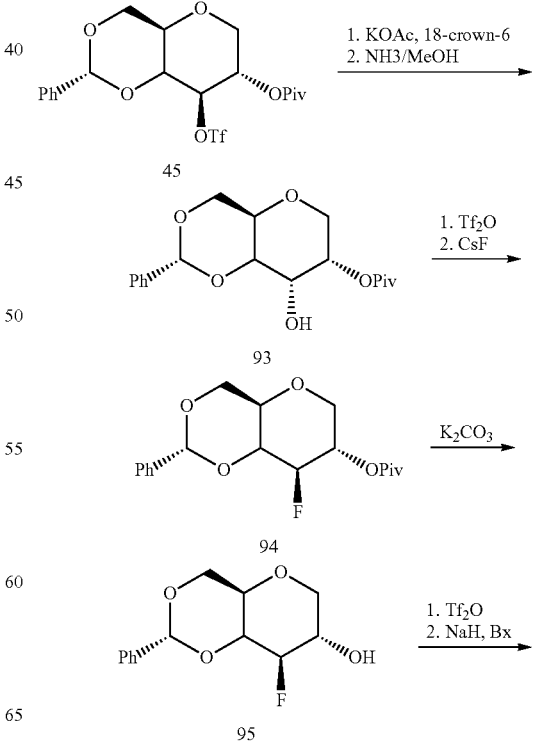

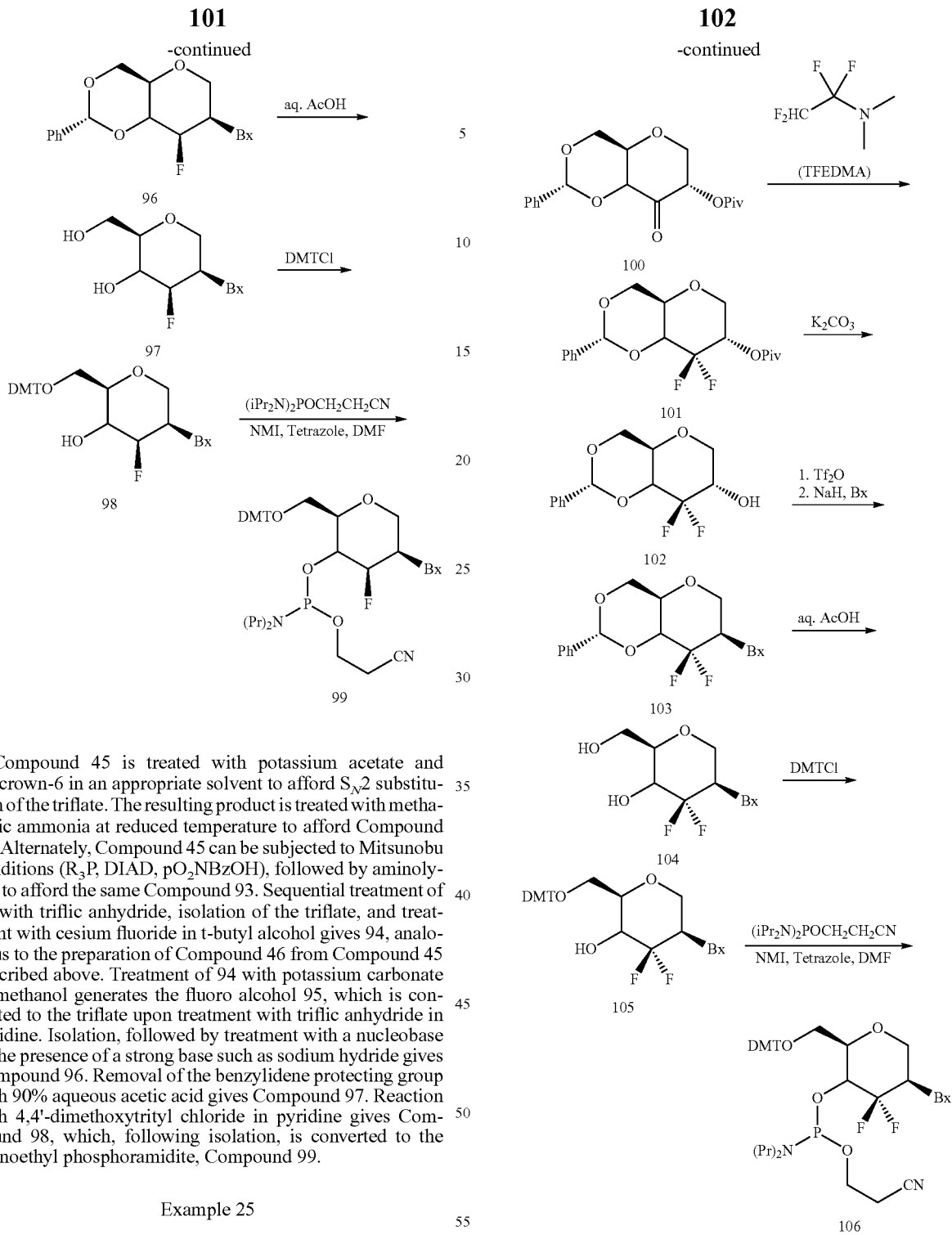

Compound 45 is treated with potassium acetate and 18-crown-6 in an appropriate solvent to afford $S_N2$ substitution of the triflate. The resulting product is treated with methanolic ammonia at reduced temperature to afford Compound 93. Alternately, Compound 45 can be subjected to Mitsunobu conditions ($R_3P$, DIAD, $pO_2NBzOH$), followed by aminolysis, to afford the same Compound 93. Sequential treatment of 93 with triflic anhydride, isolation of the triflate, and treatment with cesium fluoride in t-butyl alcohol gives 94, analogous to the preparation of Compound 46 from Compound 45 described above. Treatment of 94 with potassium carbonate in methanol generates the fluoro alcohol 95, which is converted to the triflate upon treatment with triflic anhydride in pyridine. Isolation, followed by treatment with a nucleobase in the presence of a strong base such as sodium hydride gives Compound 96. Removal of the benzylidene protecting group with 90% aqueous acetic acid gives Compound 97. Reaction with 4,4'-dimethoxytrityl chloride in pyridine gives Compound 98, which, following isolation, is converted to the cyanoethyl phosphoramidite, Compound 99.

Example 25

Preparation of Compound 106

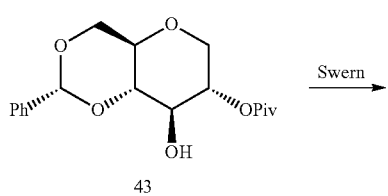

Oxidation of Compound 43 (prepared as per the procedures illustrated in Example 14) under Swern conditions (oxalyl chloride, DMSO, triethylamine, dichloromethane) gives ketone 100. Treatment with a fluorinating reagent such as 1,1,2,2-tetrafluoroethyl-N,N-dimethylamine (alternately deoxofluor or DAST) gives Compound 101. Removal of the pivaloyl group under potassium carbonate/methanol conditions gives Compound 102. Sequential treatment with triflic anhydride in pyridine, isolation, and treatment with a nucleobase in the presence of base gives the nucleoside analog, Compound 103. Removal of the benzylidene with 90% aqueous acetic acid gives Compound 104, which is converted to Compound 105 upon treatment with 4,4-dimethoxytrityl chloride in pyridine. A phosphitylation reaction provides the phosphoramidite, Compound 106.

Example 26

Preparation of Compound 116

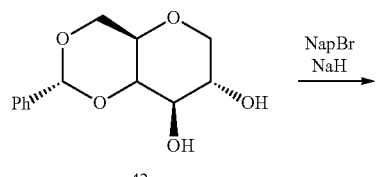
42

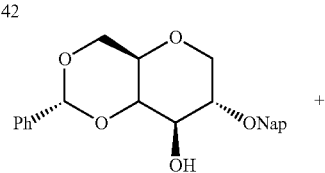
107

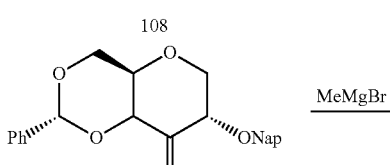
108

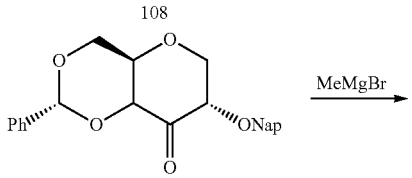
109

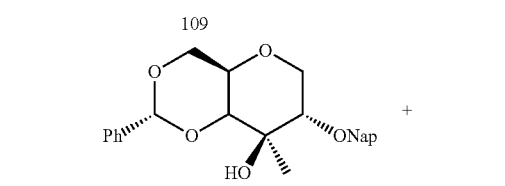
110

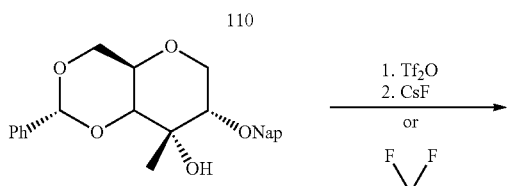
111

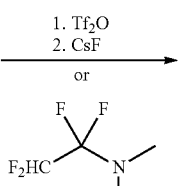
(TFEDMA)

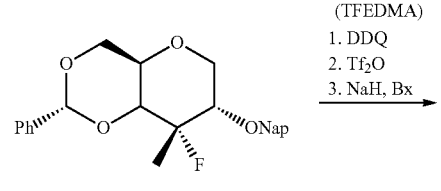
112

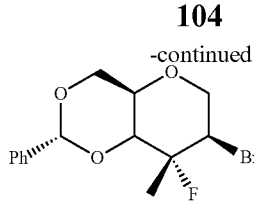
113

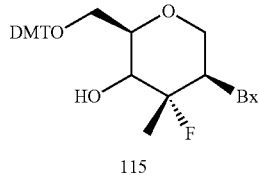
114

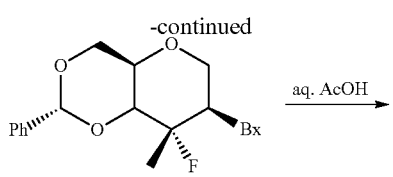
115

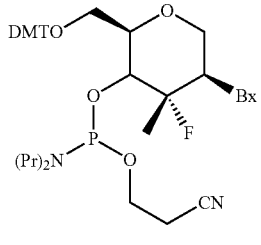
116

Treatment of Compound 42 (prepared as per the procedures illustrated in Example 14) with 2-(bromomethyl)-naphthalene (Nap bromide) in the presence of sodium hydride gives a mixture of Nap-protected regioisomers (107 and 108). Separation by silica gel chromatography provides the isomer, Compound 107. Oxidation of Compound 107 under Swern conditions (oxalyl chloride, DMSO, triethylamine, dichloromethane) gives the ketone, Compound 109, which is subsequently treated with methyl magnesium bromide (Methyl Grignard) to give a mixture of the methyl alcohols, compounds 110 and 111. Isolation of the desired stereoisomer 110 by silica gel chromatography, followed by formation of the triflate under triflic anhydride/pyridine conditions and treatment with cesium fluoride gives the fluorinated Compound 112. Alternatively, treatment of 110 with TFEDMA gives Compound 112 in a single process. Removal of the Nap protecting group with DDQ, followed by triflation, isolation, and treatment with a nucleobase in the presence of a base gives Compound 113. Removal of the benzylidene with 90% aqueous acetic acid affords Compound 114, which is converted to Compound 115 upon treatment with 4,4-dimethoxytrityl chloride in pyridine. A phosphitylation reaction provides the phosphoramidite, Compound 116.

Example 27

Preparation of Compound 129

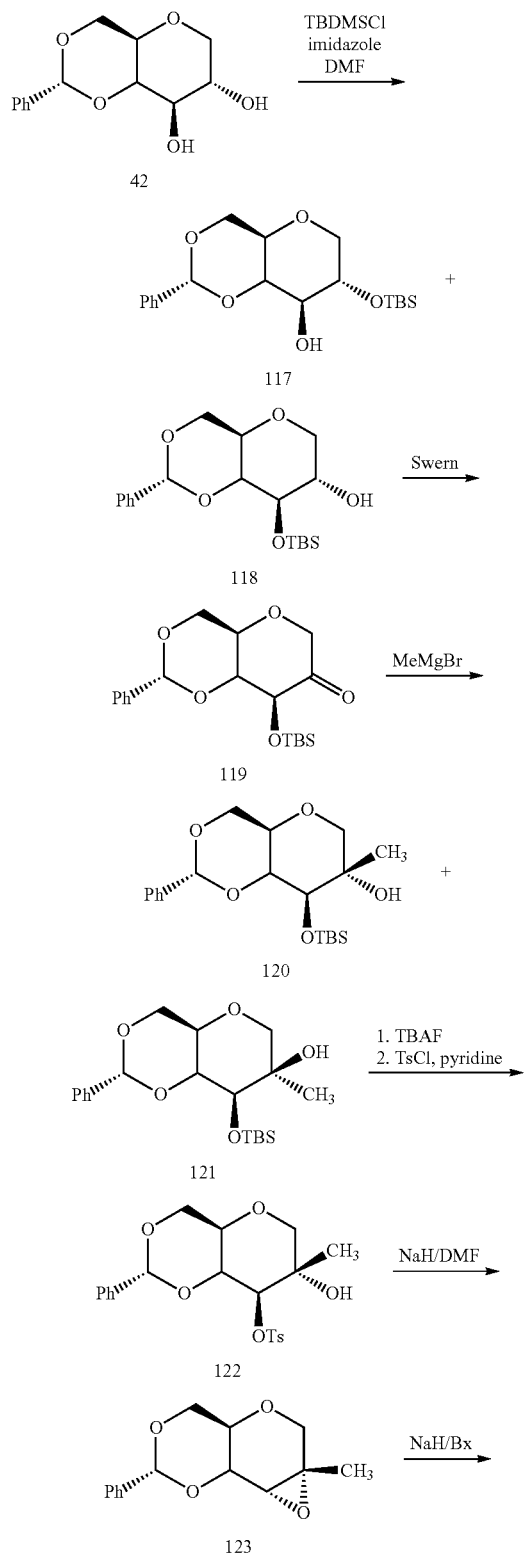

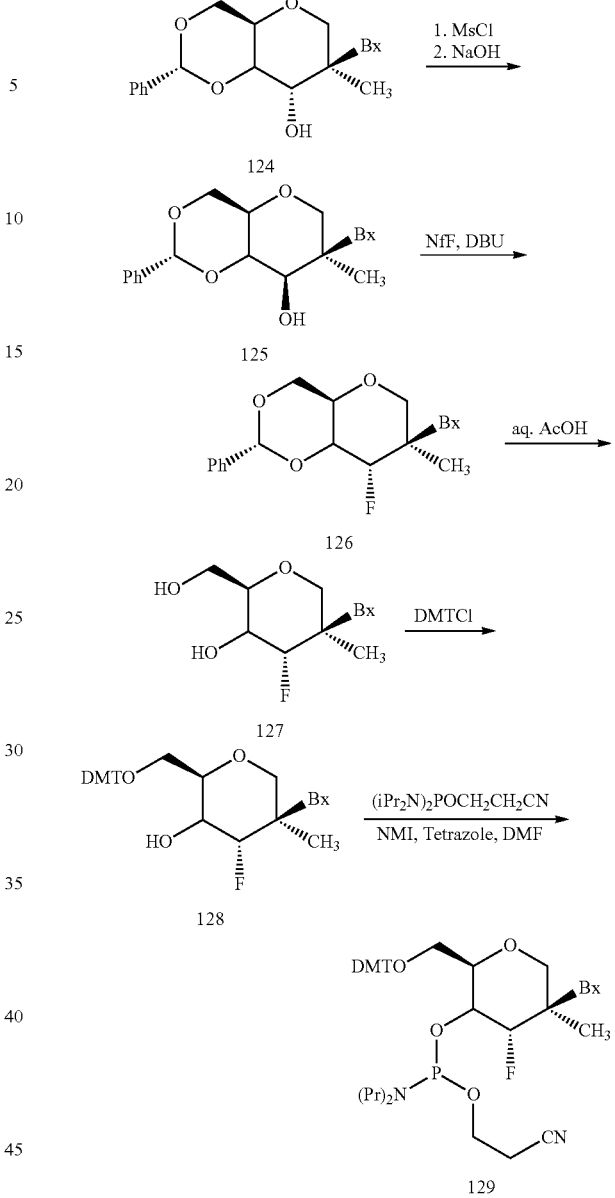

Treatment of Compound 42 (prepared as per the procedures illustrated in Example 14) with tertbutyldimethylsilyl chloride in the presence of imidazole and DMF yields a mixture of the silylated compounds 117 and 118 as described previously in *Nucleosides, Nucleotides, and Nucleic Acids* (2004), 23(1&2), 439-455. Following silica gel chromatography, the isomer, Compound 117 is oxidized under Swern conditions (oxalyl chloride, DMSO, triethylamine, dichloromethane) to generate the ketone, Compound 119. Treatment with methyl magnesium bromide gives a mixture of alcohols, compounds 120 and 121. Separation by silica gel chromatography, treatment of isolated Compound 120 with tetrabutylammonium fluoride, followed by conversion to the tosylate under tosyl chloride and pyridine conditions, gives Compound 122. Treatment with base converts tosylate 122 to the corresponding epoxide, Compound 123, as documented with similar compounds (*Bioorg. Med. Chem. Lett.* 1996, 6, 1457). Reaction of Compound 123 with a selected pyrimidine heterocycle (heterocyclic base) in the presence of base results in formation of Compound 124. Inversion of stereochemistry of the hydroxyl group is achieved by treatment with mesyl chloride, followed by hydrolysis of the resulting mesylate, which proceeds through an anhydro cyclic intermediate. Fluorination with nonafluorobutane sulfonyl fluoride under DBU/THF conditions gives the fluorinated Compound 126. Removal of the benzylidene group with 90% aqueous acetic acid affords Compound 127, which is converted to Compound 128 upon treatment with 4,4-dimethoxytrityl chloride in pyridine. A phosphitylation reaction provides the phosphoramidite, Compound 129.

Example 28

Preparation of Compound 134

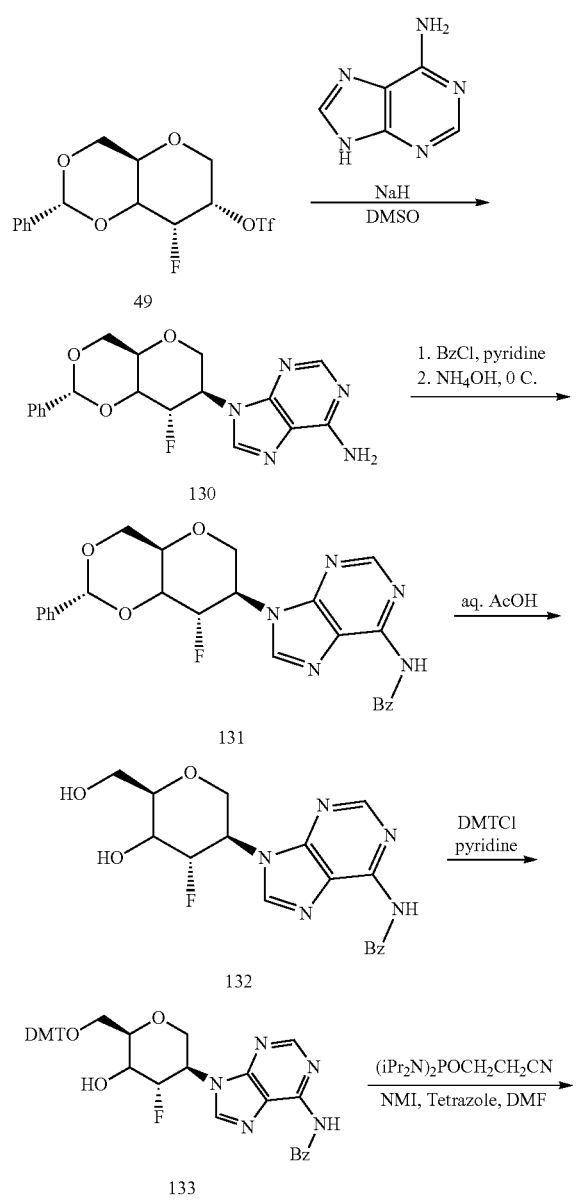

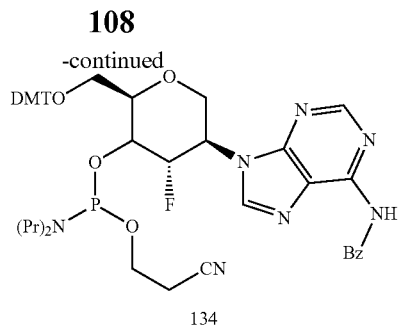

a) Preparation of Compound 130

Compound 49 (prepared as per the procedures illustrated in Example 14, 10.8 mmol, 4.20 g) and adenine (54.5 mmol, 7.35 g) were suspended in anhydrous DMSO (80 mL). To this suspension was added sodium hydride (54.4 mmol, 2.18 g of a 60% mineral oil suspension). The resulting mixture was heated to 55° C. for 12 hours, cooled to room temperature and poured into water (400 mL). The mixture was extracted with ethyl acetate (3×400 mL), and the combined organic extracts were washed with half-saturated aqueous NaCl (3×500 mL). The organic layer was dried over anhydrous $Na_2SO_4$, filtered, and evaporated to give 3.93 g (97% yield) of a brown solid. NMR ($^1H$ and $^{19}F$) and LCMS mass analysis were consistent with structure. This material was used without further purification.

b) Preparation of Compound 131

Compound 130 (10.5 mmol, 3.93 g) was dissolved in anhydrous pyridine (50 mL). After cooling to 0° C., the solution was treated with benzoyl chloride (16.9 mmol, 1.97 mL). Stirring was continued at 0° C. for 15 minutes at which time the mixture was warmed to room temperature over 2.5 hours. The mixture was cooled to 0° C., quenched with 20 mL $H_2O$ and stirred for 15 minutes. Concentrated aqueous $NH_4OH$ (20 mL) was added to the mixture with stirring for 30 minutes. The mixture was concentrated mixture in vacuo to approximately 40 mL and poured into ethyl acetate (500 mL). The mixture was washed with half-saturated aqueous NaCl (3×500 mL), dried over anhydrous $Na_2SO_4$, filtered, and evaporated to a light-brown foam. Purification by silica gel chromatography (1.5% methanol in dichloromethane) yielded 2.33 g of Compound 131 as a light brown foam. NMR ($^1H$ and $^{19}F$) and LCMS analyses were consistent with structure.

c) Preparation of Compound 132

Compound 131 (4.84 mmol, 2.30 g) was dissolved in 70 mL of 90% (v/v) aqueous acetic acid. The solution was heated to 80° C. for 4 hours and then concentrated in vacuo to a viscous yellow oil. Triethylamine (10 drops) were added followed by 5 mL of methanol and 100 mL ethyl acetate. A white precipitate formed, which was collected by filtration, washed with ethyl acetate, and vacuum dried overnight. Final mass of white solid, Compound 132, was 1.28 g (69%). NMR ($^1H$ and $^{19}F$) and LCMS analyses were consistent with structure of Compound 132.

d) Preparation of Compound 133

Compound 132 (3.24 mmol, 1.25 g) was suspended in anhydrous pyridine (12 mL). The resulting suspension was cooled to 0° C. and treated with 4,4'-dimethoxytrityl chloride (5.19 mmol, 1.76 g) with stirring. Stirring was continued at 0° C. for 15 minutes and at room temperature for 5 hours when the mixture was quenched with methanol (2 mL) and concentrated in vacuo to a thick yellow oil. The oil was dissolved in dichloromethane (150 mL) and washed with saturated aqueous $NaHCO_3$ (100 mL) followed by saturated aqueous NaCl (2×100 mL). The organic layer was dried over anhydrous Na₂SO₄, filtered, and evaporated to a yellow foam. Purification by silica gel chromatography yielded 2.05 g (92% yield) of Compound 133 as a yellow foam. NMR analysis ($^1$H and $^{19}$F) was consistent with structure.

e) Preparation of Compound 134

Compound 133 (2.59 mmol, 1.79 g) was dissolved in anhydrous DMF (6 mL) tetrazole (1.56 mmol, 109 mg), 1-methylimidazole (0.65 mmol, 52 µL) and tetraisopropylamino-2-cyanoethylphosphorodiamidite (3.90 mmol, 1.24 mL) were added. After stirring for 4.5 hours, the reaction was quenched with the addition of triethylamine (10.4 mmol, 1.45 mL). The mixture was poured into ethyl acetate (150 mL), washed with saturated aqueous NaCl (4×100 mL), dried over anhydrous Na₂SO₄, filtered, and evaporated to a pale yellow foam. The solid was redissolved in ethyl acetate (7 mL) and precipitated by dropwise addition into 70 mL of hexanes. Silica gel purification (1:1 hexanes:ethyl acetate) of the resulting precipitate yielded 1.92 g (83%) of Compound 134 as a white foam. NMR ($^1$H, $^{19}$F, and $^{31}$P) are consistent with structure. $^{31}$P NMR (CDCl₃): δ ppm 151.64, 151.58, 150.37, 150.33.

Example 29

Preparation of Compound 140

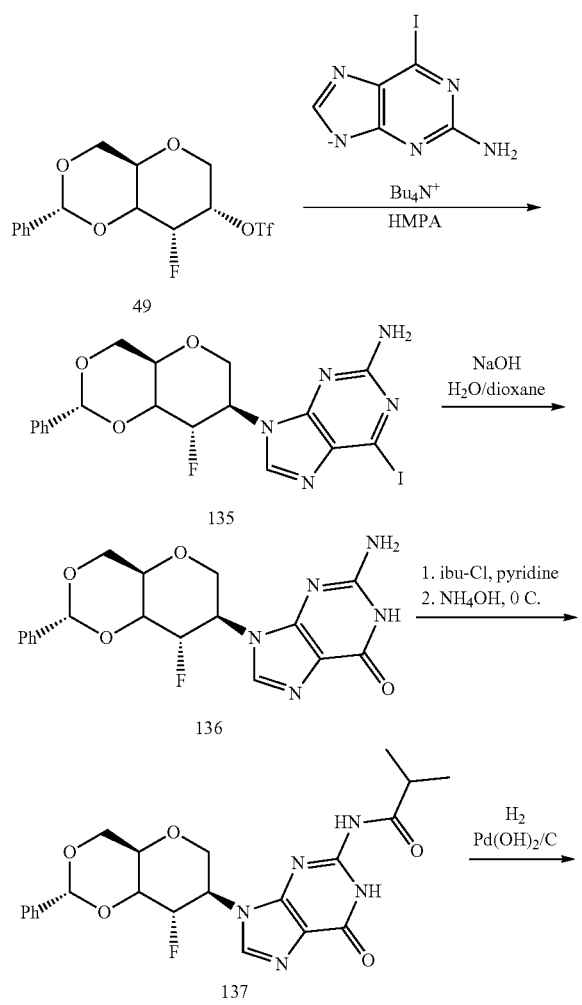

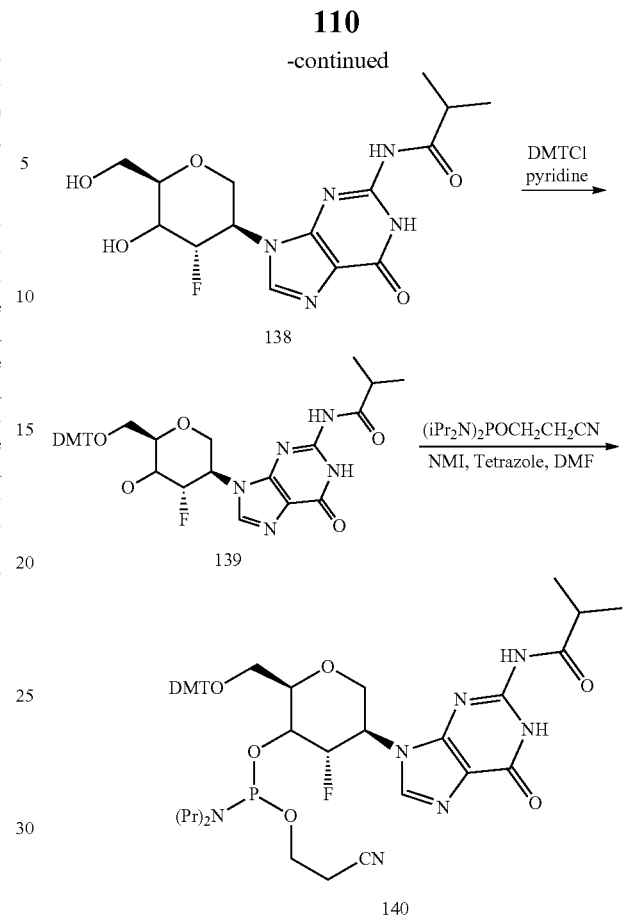

a) Preparation of Compound 135

Compound 49 (prepared as per the procedures illustrated in Example 14, 7.51 mmol, 2.9 g) and 6-iodo-2-aminopurine tetrabutylammonium salt (17.6 mmol, 8.5 g, prepared as described in *J. Org. Chem.* 1995, 60, 2902-2905), were dissolved in anhydrous HMPA (26 mL). The mixture was stirred at room temperature for 18 hours, poured into ethyl acetate, washed with water and saturated NaCl, dried over anhydrous Na₂SO₄, filtered and evaporated. Purification by silica gel chromatography (1:1 hexanes:ethyl acetate) yielded 2.78 g (75% yield) of Compound 135. NMR ($^1$H and $^{19}$F) and LCMS analyses were consistent with structure.

b) Preparation of Compound 136

Compound 135 (0.64 mmol, 0.32 g) was dissolved in 1,4-dioxane (9 mL) and 9 mL of 1M aqueous NaOH was added with heating at 55° C. for 18 hours. The mixture was cooled then neutralized with 1N HCl. The mixture was concentrated in vacuo and the residue purified by silica gel chromatography (5% methanol in dichloromethane) to yield 0.22 g (88% yield) of 136. NMR ($^1$H and $^{19}$F) and LCMS analyses were consistent with structure.

c) Preparation of Compound 137

Compound 136 (3.23 mmol, 1.25 g) was dissolved in anhydrous pyridine (13.6 mL), cooled to 0° C., then treated with isobutyryl chloride (4.85 mmol, 0.51 mL). The mixture was warmed to room temperature and stirred for 6 hours. The mixture was cooled to 0° C. and treated with concentrated aqueous NH₄OH (3.2 mL) with stirring for 30 minutes. The mixture was poured into ethyl acetate (100 mL), washed with water (200 mL) and brine (200 mL), dried over anhydrous Na₂SO₄, filtered, and evaporated. Purification by silica gel chromatography (gradient of 0 to 5% methanol in dichloromethane) yielded 1.21 g (82% yield) of Compound 137. NMR ($^1$H and $^{19}$F) and LCMS analyses were consistent with structure.

d) Preparation of Compound 138

Compound 137 (0.219 mmol, 0.103 g) was dissolved in methanol (10 mL) and acetic acid (0.2 mL) and Pd(OH)$_2$/C (0.44 g) were added with stirring under an atmosphere (balloon pressure) of hydrogen for 14 hours. The catalyst was removed by filtration, and the resulting filtrate was concentrated and triturated with acetonitrile to obtain Compound 138 as a white solid. NMR ($^1$H and $^{19}$F) and LCMS analyses were consistent with structure.

e) Preparation of Compound 139

Compound 138 (3.83 mmol, 1.41 g) was dissolved in anhydrous pyridine (32 mL) and 4,4'-dimethoxytrityl chloride (5.0 mmol, 1.71 g) was added with stirring at room temperature for 3 hours followed by quenching with methanol (0.5 mL). The solution was concentrated in vacuo, then redissolved in ethyl acetate. The organic solution was washed with saturated aqueous NaHCO$_3$ and brine, dried over anhydrous Na$_2$SO$_4$, filtered, and evaporated. Purification by silica gel chromatography yielded 1.63 g (70% yield) of 139. NMR ($^1$H and $^{19}$F) analysis was consistent with structure.

f) Preparation of Compound 140

Compound 139 (1.59 mmol, 1.07 g) was dissolved in anhydrous DMF (4.25 mL) and tetrazole (1.35 mmol, 95 mg), 1-methylimidazole (0.45 mmol, 35 µL), and tetraisopropyl-2-cyanoethylphosphorodiamidite (2.25 mmol, 0.71 mL) were added. The mixture was stirred at room temperature for 3 hours, poured into ethyl acetate and washed with saturated aqueous NaHCO$_3$ and brine. The organic layer was dried over anhydrous Na$_2$SO$_4$, filtered, and evaporated. Purification by silica gel chromatography yielded 1.07 g (78% yield) of Compound 140. NMR ($^1$H, $^{19}$F, and $^{31}$P) analysis was consistent with structure. $^{31}$P NMR (CDCl$_3$): δ ppm 151.30, 151.24, 148.82, 148.78.

Example 30

Preparation of Gapped Oligomeric Compounds

Automated solid-phase synthesis was used to prepare oligomeric compounds used herein. One illustrative gapped oligomeric compound is ISIS-410131, having SEQ ID NO: 01, and Formula: 5'-C$_f$U$_f$TAGCACTGGCC$_f$U$_f$-3'. Each internucleoside linking group is a phosphorothioate, each of the T, A, G and C letters not followed by a subscript f designates a β-D-2'-deoxyribonucleoside and each C$_f$ and U$_f$ is a monomer subunit wherein Bx is the heterocyclic base cytosine or uridine respectively and wherein the monomer subunit has the Formula and configuration:

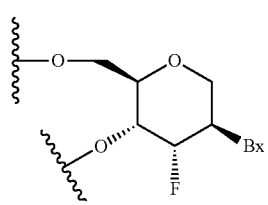

The synthesis of 410131 was carried out on a 40 mmol scale using an ÄKTA Oligopilot 10 (GE Healthcare) synthesizer with a polystyrene solid support loaded at 200 mmol/g with a universal linker. All nucleoside phosphoramidites, including compounds 8 and 13 were prepared as 0.1 M solutions in anhydrous acetonitrile. Coupling was performed using 4 molar equivalents of the respective phosphoramidite in the presence of 4,5-dicyanoimidazole, with a coupling time of 14 minutes. Thiolation of trivalent phosphorous to the phosphorothioate was achieved upon treatment with 0.2 M phenylacetyl disulfide in 1:1 3-picoline:acetonitrile. The resulting gapped oligomeric compound was deprotected using 1:1 triethylamine:acetonitrile (1 hour at room temperature), followed by conc. aq. NH$_4$OH at 55° C. for 7 hours. Ion exchange purification followed by reverse-phase desalting yielded 9.8 mmol (44 mg) of purified oligonucleotide. Mass and purity analysis by LC/MS ion-pair chromatography showed a UV purity of 98.5%, with an ESI mass of 4522.8 Da (calc. 4523.6 Da).

Example 31

2-10-2 Gapped Oligomeric Compounds Targeted to PTEN

In Vitro Study

Gapped oligomeric compounds were synthesized and tested for their ability to reduce PTEN expression over a range of doses. bEND cells were transfected with gapped oligomeric compounds at doses of 0.3125, 0.625, 1.25, 2.5, 5, 10, 20 or 40 nM using 3 µg/mL Lipofectin in OptiMEM for 4 hrs, after which transfection mixtures were replaced with normal growth media (DMEM, high glucose, 10% FBS, pen-strep). RNA was harvested the following day (approximately 24 hours from the start of transfection) and analyzed for PTEN and cyclophilin A RNA levels using real time RT-PCR. Values represent averages and standard deviations (n=3) of PTEN RNA levels normalized to those of cyclophilin A.

The resulting dose-response curves were used to determine the IC$_{50}$s listed below. Tms were determined in 100 mM phosphate buffer, 0.1 mM EDTA, pH 7, at 260 nm using 4 µM of the modified oligomers listed below and 4 µM of the complementary RNA AGGCCAGTGCTAAG (SEQ ID NO: 7).

| SEQ ID NO./ ISIS NO. | Composition (5' to 3') | Tm (° C.) | IC$_{50}$ (nM) |
|---|---|---|---|
| 01/392753 | C$_e$U$_e$TAGCACTGGCC$_e$U$_e$ | 51.3 | 37 |
| 01/410312 | C$_m$U$_m$TAGCACTGGCC$_m$U$_m$ | 49.2 | 23 |
| 01/410131 | C$_f$U$_f$TAGCACTGGCC$_f$U$_f$ | 50.0 | 16 |

Each internucleoside linking group is a phosphorothioate. Subscripted nucleosides are defined below wherein Bx is a heterocyclic base:

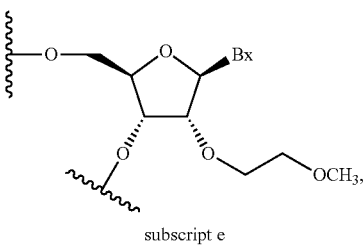

subscript e

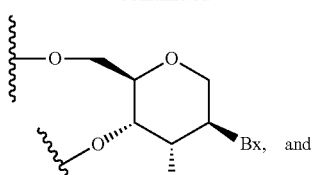

subscript m

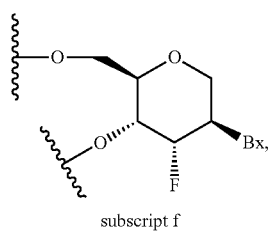

subscript f

Example 32

2-10-2 Gapped Oligomeric Compounds Targeted to PTEN

In Vitro Study

Gapped oligomeric compounds were synthesized and tested for their ability to reduce PTEN expression over a range of doses. bEND cells were transfected with gapped oligomeric compounds at doses of 0.3125, 0.625, 1.25, 2.5, 5, 10, 20 or 40 nM using 3 μg/mL Lipofectin in OptiMEM for 4 hrs, after which transfection mixtures were replaced with normal growth media (DMEM, high glucose, 10% FBS, pen-strep). RNA was harvested the following day (approximately 24 hours from start of transfection) and analyzed for PTEN and cyclophilin A RNA levels using real time RT-PCR. Values represent averages and standard deviations (n=3) of PTEN RNA levels normalized to those of cyclophilin A.

| SEQ ID NO./ ISIS NO. | Composition (5' to 3') |
|---|---|
| 02/392063 | $^{Me}C_lT_l$TAGCACTGGC$^{Me}C_lT_l$ |
| 01/410131 | $C_fU_f$TAGCACTGGCC$_fU_f$ |
| 02/417999 | $^{Me}C_lT_l$TAGCACTGGC$^{Me}C_lT_f$ |

| SEQ ID NO./ ISIS NO. | % UTC @ Dosage | | | | | | | |
|---|---|---|---|---|---|---|---|---|
| | 0.3125 | 0.625 | 1.25 | 2.5 | 5 | 10 | 20 | 40 |
| 02/392063 | 86 | 83 | 66 | 40 | 36 | 24 | 32 | 17 |
| 01/410131 | 78 | 70 | 71 | 50 | 52 | 35 | 29 | 17 |
| 02/417999 | 98 | 108 | 77 | 72 | 68 | 43 | 33 | 20 |

Each internucleoside linking group is a phosphorothioate and superscript Me indicates that the following C is a 5-methyl C. Subscripted nucleosides are defined below wherein Bx is a heterocyclic base:

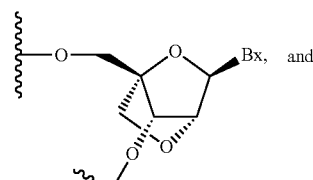

subscript l

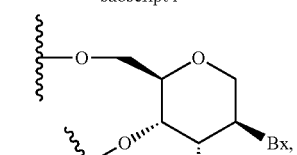

subscript f

Example 33

2-10-2 Gapped Oligomeric Compounds Targeted to PTEN

In Vivo Study

Six week old Balb/c mice (Jackson Laboratory, Bar Harbor, Me.) were injected once with the gapped oligomeric compounds targeted to PTEN at a dose of 20 or 60 mg/kg. The mice were sacrificed 72 hrs following administration. Liver tissues were homogenized and mRNA levels were quantitated using real-time PCR as described herein for comparison to untreated control levels (% UTC). Plasma chemistry analysis was completed.

| SEQ ID NO./ ISIS NO. | Composition (5' to 3') | dose (mg/kg) | % UTC |
|---|---|---|---|
| saline | | N/A | 100 |
| 01/392753 | $C_eU_e$TAGCACTGGCC$_eU_e$ | 20 | 84 |
| 01/392753 | $C_eU_e$TAGCACTGGCC$_eU_e$ | 60 | 68 |
| 01/410312 | $C_mU_m$TAGCACTGGCC$_mU_m$ | 20 | 83 |
| 01/410312 | $C_mU_m$TAGCACTGGCC$_mU_m$ | 60 | 27 |
| 01/410131 | $C_fU_f$TAGCACTGGCC$_fU_f$ | 20 | 26 |
| 01/410131 | $C_fU_f$TAGCACTGGCC$_fU_f$ | 60 | 8 |

Each internucleoside linking group is a phosphorothioate. Subscripted nucleosides are defined below:

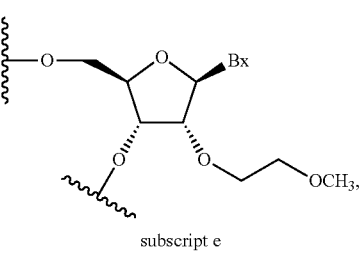

subscript e

-continued

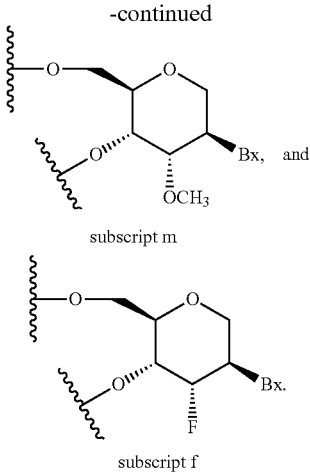

subscript m subscript f

No increase in ALT and no significant effect on body or organ weights were observed after treatment with these gapped oligomeric compounds.

Example 34

Gapped Oligomeric Compounds Targeted to PTEN

In Vivo Study

Six week old Balb/c mice (Jackson Laboratory, Bar Harbor, Me.) were injected twice per week for three weeks with the gapped oligomeric compounds targeted to PTEN at a dose of 0.47, 1.5, 4.7 or 15 mg/kg. The mice were sacrificed 48 hours following last administration. Liver tissues were homogenized and mRNA levels were quantitated using real-time PCR as described herein for comparison to untreated control levels (% UTC). Plasma chemistry analysis was completed. Tms were determined in 100 mM phosphate buffer, 0.1 mM EDTA, pH 7, at 260 nm using 4 µM of the modified oligomers listed below and 4 µM of the complementary RNA AGGCCAGTGCTAAG (SEQ ID NO: 7).

| SEQ ID NO./ ISIS NO. | Composition (5' to 3') | Tm (° C.) |
|---|---|---|
| 01/410131 | $C_fU_fTAGCACTGGCC_fU_f$ | 50.7 |
| 02/417999 | $^{Me}C_fT_fTAGCACTGGC^{Me}C_fT_f$ | 52.6 |

Each internucleoside linking group is a phosphorothioate, superscript Me indicates that the following C is a 5-methyl C and nucleosides followed by a subscript f are defined in the formula below wherein Bx is a heterocyclic base:

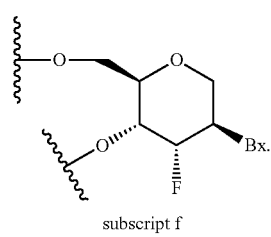

subscript f

| SEQ ID NO./ ISIS NO. | % UTC @ 0.47 mg/kg | % UTC @ 1.5 mg/kg | % UTC @ 4.7 mg/kg | % UTC @ 15 mg/kg |
|---|---|---|---|---|
| 01/410131 | — | — | — | 12 |
| 02/417999 | 77 | 64 | 31 | 10 |
| Saline | % UTC = 100 (dosage N/A) | | | |

Liver transaminase levels, alanine aminotranferease (ALT) and aspartate aminotransferase (AST), in serum were also measured relative to saline injected mice. The approximate liver transaminase levels are listed in the table below.

| SEQ ID NO./ ISIS NO. | AST @ 0.47 mg/kg | AST @ 1.5 mg/kg | AST @ 4.7 mg/kg | AST @ 15 mg/kg |
|---|---|---|---|---|
| 01/410131 | — | — | — | 106 |
| 02/417999 | 51 | 90 | 86 | 37 |
| Saline | 82 (dosage N/A) | | | |

| SEQ ID NO./ ISIS NO. | ALT @ 0.47 mg/kg | ALT @ 1.5 mg/kg | ALT @ 4.7 mg/kg | ALT @ 15 mg/kg |
|---|---|---|---|---|
| 01/410131 | — | — | — | 27 |
| 02/417999 | 28 | 31 | 42 | 21 |
| Saline | 34 (dosage N/A). | | | |

Example 35

Gapped Oligomeric Compounds Targeted to PTEN

In Vivo Study

Six week old Balb/c mice (Jackson Laboratory, Bar Harbor, Me.) were injected once with the gapped oligomeric compounds targeted to PTEN at a dose of 3.2, 10, 32 or 100 mg/kg. The mice were sacrificed 72 hours following administration. Liver tissues were homogenized and mRNA levels were quantitated using real-time PCR as described herein for comparison to untreated control levels (% UTC). Plasma chemistry analysis was completed. Tms were determined in 100 mM phosphate buffer, 0.1 mM EDTA, pH 7, at 260 nm using 4 µM of the modified oligomers listed below and 4 µM of the complementary RNA TCAAGGCCAGTGCTAA-GAGT (SEQ ID NO: 8) for 2/14/2 motif oligomers and AGGCCAGTGCTAAG (SEQ ID NO: 7) for 2/10/2 oligomers.

| SEQ ID NO./ ISIS NO. | Composition (5' to 3') | Tm (° C.) | Motif |
|---|---|---|---|
| 03/411026 | $C_fU_fGCTAGCCTCTGGATU_fU_f$ | 57.1 | 2/14/2 |
| 04/418000 | $^{Me}C_fT_fGCTAGCCTCTGGATT_fT_f$ | 58.5 | 2/14/2 5-CH$_3$ wings |
| 01/410131 | $C_fU_fTAGCACTGGCC_fU_f$ | 50.7 | 2/10/2 |
| 02/417999 | $^{Me}C_fT_fTAGCACTGGC^{Me}C_fT_f$ | 52.6 | 2/10/2 5-CH$_3$ wings |
| 02/392063 | $^{Me}C_fT_fTAGCACTGGC^{Me}C_fT_f$ | 60.5 | 2/10/2 5-CH$_3$ wings |

Each internucleoside linking group is a phosphorothioate and superscript Me indicates that the following C is a 5-methyl C. Subscripted nucleosides are defined below wherein Bx is a heterocyclic base:

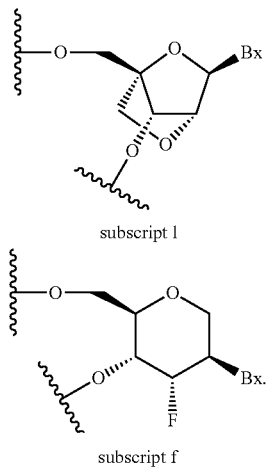

subscript l subscript f

| SEQ ID NO./ ISIS NO. | % UTC @ 3.2 mg/kg | % UTC @ 10 mg/kg | % UTC @ 32 mg/kg | % UTC @ 100 mg/kg |
|---|---|---|---|---|
| 02/392063 | 92 | 29 | 7 | 7 |
| 03/411026 | 92 | 52 | 12 | 7 |
| 04/418000 | 100 | 38 | 12 | 5 |
| 01/410131 | 100 | 59 | 9 | 3 |
| 02/417999 | 94 | 31 | 10 | 5 |
| Saline | % UTC = 100 | | | |

Liver transaminase levels, alanine aminotranferease (ALT) and aspartate aminotransferase (AST), in serum were also measured relative to saline injected mice. The approximate liver transaminase levels are listed in the table below.

| SEQ ID NO./ ISIS NO. | AST @ 3.2 mg/kg | AST @ 10 mg/kg | AST @ 32 mg/kg | AST @ 100 mg/kg |
|---|---|---|---|---|
| 02/392063 | 57 | 86 | 81 | 27399 |
| 03/411026 | 166 | 78 | 69 | 130 |
| 04/418000 | 90 | 94 | 80 | 345 |
| 01/410131 | 48 | 87 | 187 | 51 |
| 02/417999 | 72 | 126 | 99 | 55 |

| SEQ ID NO./ ISIS NO. | ALT @ 3.2 mg/kg | ALT @ 10 mg/kg | ALT @ 32 mg/kg | ALT @ 100 mg/kg |
|---|---|---|---|---|
| 02/392063 | 9 | 13 | 10 | 18670 |
| 03/411026 | 25 | 20 | 26 | 115 |
| 04/418000 | 17 | 33 | 44 | 321 |
| 01/410131 | 14 | 15 | 22 | 11 |
| 02/417999 | 13 | 22 | 15 | 11. |

Example 36

Gapped Oligomeric Compounds Targeted to PTEN

In Vivo Study

Six week old Balb/c mice (Jackson Laboratory, Bar Harbor, Me.) were injected once with the gapped oligomeric compounds targeted to PTEN at a dose of 3.2, 10, 32 or 100 mg/kg. The mice were sacrificed 72 hours following last administration. Liver tissues were homogenized and mRNA levels were quantitated using real-time PCR as described herein for comparison to untreated control levels (% UTC). Estimated $ED_{50}$ concentrations for each oligomeric compound were calculated using Graphpad Prism as shown below.

| SEQ ID NO./ ISIS NO. | Composition (5' to 3') | $ED_{50}$ (mg/kg) |
|---|---|---|
| 02/417999 | $^{Me}C_fT_f$TAGCACTGGC$^{Me}C_fT_f$ | 7.5 |
| 02/425857 | $^{Me}C_hT_h$TAGCACTGGC$^{Me}C_hT_h$ | 14.5 |

Each internucleoside linking group is a phosphorothioate and superscript Me indicates that the following C is a 5-methyl C. Subscripted nucleosides are defined below wherein Bx is a heterocyclic base:

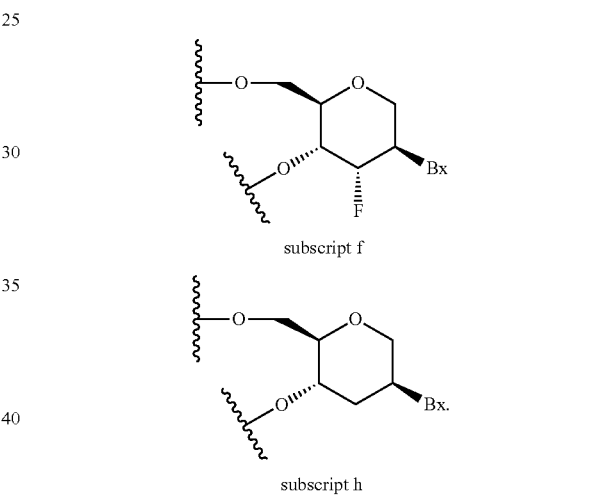

subscript f subscript h

| SEQ ID NO./ | % UTC at dosage | | | |
|---|---|---|---|---|
| ISIS NO. | 3.2 mg/kg | 10 mg/kg | 32 mg/kg | 100 mg/kg |
| 02/417999 | 77 | 41 | 9 | 5 |
| 02/425857 | 76 | 72 | 20 | 6 |
| Saline | 100 | | | |

Liver transaminase levels, alanine aminotranferease (ALT) and aspartate aminotransferase (AST), in serum were also measured relative to saline injected mice. The approximate liver transaminase levels are listed in the table below.

| SEQ ID NO./ | AST (IU/L) at dosage | | | |
|---|---|---|---|---|
| ISIS NO. | 3.2 mg/kg | 10 mg/kg | 32 mg/kg | 100 mg/kg |
| 02/417999 | 72 | 126 | 99 | 55 |
| 02/425857 | 88 | 64 | 77 | 46 |
| Saline | 77 (dosage: n/a) | | | |

| SEQ ID NO./ | ALT (IU/L) at dosage | | | |
|---|---|---|---|---|
| ISIS NO. | 3.2 mg/kg | 10 mg/kg | 32 mg/kg | 100 mg/kg |
| 02/417999 | 26 | 24 | 19 | 31 |
| 02/425857 | 28 | 26 | 29 | 51 |
| Saline | 31 (dosage: n/a). | | | |

Example 37

Gapped Oligomeric Compounds

Oligomeric compounds were prepared having a gapped motif with various gap and wing sizes. Tms were determined in 100 mM phosphate buffer, 0.1 mM EDTA, pH 7, at 260 nm using 4 μM of the modified oligomers listed below and 4 μM of either the complementary RNA TCAAGGCCAGTGCTAAGAGT (SEQ ID NO: 8) for $Tm^1$ or AGGCCAGTGCTAAG (SEQ ID NO: 7) for $Tm^2$.

| SEQ ID NO./ ISIS NO. | Composition (5' to 3') | $Tm^1$ (° C.) | Gapmer Design |
|---|---|---|---|
| 02/417999 | $^{Me}C_fT_fTAGCACTGGC^{Me}C_fT_f$ | 59.4 | 2-10-2 |
| 02/425858 | $^{Me}C_fT_fAGCACTGG^{Me}C_f^{Me}C_fT_f$ | 67.4 | 3-8-3 |
| 05/425859 | $T_f^{Me}C_fT_fTAGCACTGGC^{Me}C_fT_fT_f$ | 65.0 | 3-10-3 |
| 05/425860 | $T_f^{Me}C_fT_fAGCACTGG^{Me}C_f^{Me}C_fT_fT_f$ | 70.4 | 4-8-4 |
| 06/425861 | $^{Me}C_fT_f^{Me}C_fT_fAGCACTGG^{Me}C_f^{Me}C_fT_fT_f$ | 74.3 | 5-8-4 |

Each internucleoside linking group is a phosphorothioate and superscript Me indicates that the following C is a 5-methyl C. Subscripted nucleoside is defined below wherein Bx is a heterocyclic base:

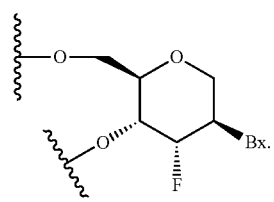

subscript f

Example 38

Hemimers Targeted to PTEN

In Vivo Study

Six week old Balb/c mice (Jackson Laboratory, Bar Harbor, Me.) were injected once with the gapped oligomeric compounds targeted to PTEN at a dose of 1.6, 5, 16 or 50 mg/kg. The mice were sacrificed 72 hours following last administration. Liver tissues were homogenized and mRNA levels were quantitated using real-time PCR as described herein for comparison to untreated control levels (% UTC). Estimated $ED_{50}$ concentrations for each oligomeric compound were calculated using Graphpad Prism as shown below. Tms were determined in 100 mM phosphate buffer, 0.1 mM EDTA, pH 7, at 260 nm using 4 μM of the modified oligomers listed below and 4 μM of either the complementary RNA TCAAGGCCAGTGCTAAGAGT (SEQ ID NO: 8) for $Tm^1$ or AGGCCAGTGCTAAG (SEQ ID NO: 7) for $Tm^2$.

| SEQ ID NO./ ISIS NO. | Composition (5' to 3') | $Tm^1$ | $Tm^2$ |
|---|---|---|---|
| 02/412471 | $^{Me}C_fT_fT_fAGCACTGGC^{Me}CT$ | 65.5 | 62.5 |
| 02/429495 | $^{Me}C_fT_fT_fAGCACTGGC^{Me}CT$ | 63.8 | 59.6 |

Each internucleoside linking group is a phosphorothioate and superscript Me indicates that the following C is a 5-methyl C. Subscripted nucleosides are defined below wherein Bx is a heterocyclic base:

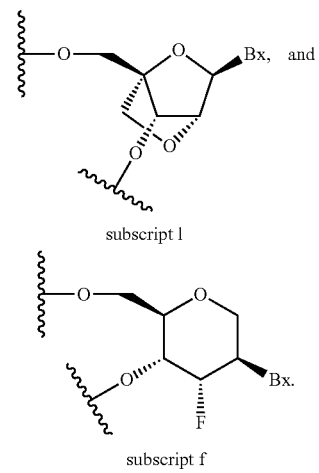

subscript l subscript f

| SEQ ID NO./ | % UTC at dosage | | | |
|---|---|---|---|---|
| ISIS NO. | 1.6 mg/kg | 5 mg/kg | 16 mg/kg | 50 mg/kg |
| 02/412471 | 85 | 51 | 20 | 23 |
| 02/429495 | 90 | 79 | 40 | 17 |
| Saline | % UTC = 100 | | | |

Liver transaminase levels, alanine aminotranferease (ALT) and aspartate aminotransferase (AST), in serum were also measured relative to saline injected mice. The approximate liver transaminase levels are listed in the table below.

| SEQ ID NO./ ISIS NO. | 1.6 mg/kg | 5 mg/kg | 16 mg/kg | 50 mg/kg |
|---|---|---|---|---|
| | AST (IU/L) at dosage | | | |
| 02/412471 | 67 | 67 | 69 | 4572 |
| 02/429495 | 95 | 54 | 77 | 58 |
| Saline | 68 (dosage: n/a) | | | |
| | ALT (IU/L) at dosage | | | |
| 02/412471 | 29 | 31 | 33 | 3419 |
| 02/429495 | 33 | 31 | 38 | 23 |
| Saline | 35 (dosage: n/a). | | | |

What is claimed is:

1. An oligomeric compound having from 8 to 40 linked monomeric subunits comprising:

at least one tetrahydropyran nucleoside analog having one of Formulas Ib or Ic:

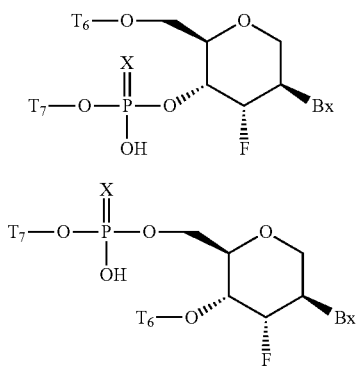

wherein independently for each tetrahydropyran nucleoside analog of said formula:

Bx is a heterocyclic base moiety;

X is O or S;

$T_6$ is H, a hydroxyl protecting group, a 5' or 3'-terminal group or an internucleoside linking group linking the tetrahydropyran nucleoside analog to at least one of said monomer subunits;

$T_7$ is at least one of said monomer subunits;

X is O or S; and at least one modified nucleoside wherein each of said at least one modified nucleoside is, independently, selected from a bicyclic nucleoside, a 2'-modified nucleoside, a 4'-thio modified nucleoside and a 4'-thio-2'-modified nucleoside;

wherein said oligomeric compound is hybridizable to at least a portion of a target nucleic acid.

2. The oligomeric compound of claim 1 comprising a plurality of the at least one modified nucleoside.

3. The oligomeric compound of claim 2 wherein each of the modified nucleosides is, independently, selected from bicyclic nucleosides and 2'-modified nucleosides.

4. The oligomeric compound of claim 3 wherein each of the 2'-modified nucleosides comprises a 2'-substituent group independently selected from 2'-F, 2'-OCH$_3$ and 2'-O(CH$_2$)$_2$—OCH$_3$.

5. The oligomeric compound of claim 3 wherein each of the modified nucleosides is, a bicyclic nucleoside.

6. The oligomeric compound of claim 2 wherein each of the modified nucleosides, independently, has one of Formulas Id or Ie:

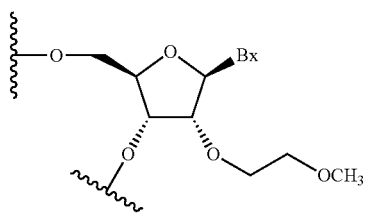

Ie

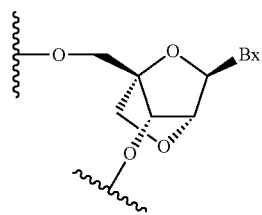

wherein each Bx is a heterocyclic base moiety.

7. The oligomeric compound of claim 1 comprising at least one 5' or 3'-terminal group.

8. The oligomeric compound of claim 7 wherein at least one of the 5' and 3'-terminal groups is a linked conjugate group.

9. The oligomeric compound of claim 1 wherein each of the monomer subunits that is not a tetrahydropyran nucleoside analog of said formula or a modified nucleoside is a β-D-2'-deoxyribonucleoside.

10. The oligomeric compound of claim 1 wherein each of the monomer subunits comprises a heterocyclic base moiety independently selected from uracil, thymine, cytosine, adenine or guanine.

11. The oligomeric compound of claim 10 wherein each cytosine heterocyclic base optionally includes a 5-methyl group.

12. The oligomeric compound of claim 1 wherein essentially all of the internucleoside linking groups linking the monomer subunits are phosphorothioate internucleoside linking groups.

13. The oligomeric compound of claim 1 wherein essentially all of the internucleoside linking groups linking the monomer subunits are phosphodiester internucleoside linking groups.

14. The oligomeric compound of claim 1 wherein each internucleoside linking group linking the monomer subunits is, independently, selected from a phosphorothioate or a phosphodiester internucleoside linking group.

15. The oligomeric compound of claim 1 wherein a least one internucleoside linking group between two monomer subunits is a phosphorothioate internucleoside linking group.

16. The oligomeric compound of claim 1 comprising at least one β-D-2'-deoxyribonucleoside that is linked to a tetrahydropyran nucleoside analog by a phosphorothioate internucleoside linking group.

17. The oligomeric compound of claim 1 comprising at least one contiguous region of from 2 to about 8 monomer subunits independently selected from tetrahydropyran nucleoside analogs of said formula and modified nucleosides.

18. The oligomeric compound of claim 17 further comprising at least one additional region of from 2 to about 8 contiguous monomer subunits independently selected from tetrahydropyran nucleoside analogs of said formula and modified nucleosides wherein the additional region is separated from the at least one region by at least one β-D-2'-deoxyribonucleoside.

19. The oligomeric compound of claim 17 comprising a 3' or 5'-hemimer wherein said at least one contiguous region of from 2 to 8 monomer subunits is positioned at either the 5' or 3'-end of the oligomeric compound and further comprising a second region of at least 6 β-D-2'-deoxyribonucleosides.

20. The oligomeric compound of claim 1 wherein said oligomeric compound comprises a motif selected from a gapped motif, a hemimer motif, a blockmer motif, a positionally modified motif and an alternating motif.

21. The oligomeric compound of claim 1 comprising from 10 to about 21 monomer subunits.

22. The oligomeric compound of claim 1 comprising from 12 to about 17 monomer subunits.

23. The oligomeric compound of claim 1 comprising from 13 to about 16 monomer subunits.

* * * * *